(12) United States Patent
Cournoyer et al.

(10) Patent No.: US 7,056,903 B2
(45) Date of Patent: Jun. 6, 2006

(54) CARBOXYLIC ACID DERIVATIVES AS IP ANTAGONISTS

(75) Inventors: Richard Leo Cournoyer, San Francisco, CA (US); Paul Francis Keitz, Redwood City, CA (US); Lee Edwin Lowrie, Jr., Santa Clara, CA (US); Alexander Victor Muehldorf, Sunnyvale, CA (US); Counde O'Yang, Sunnyvale, CA (US); Dennis Mitsugu Yasuda, Campbell, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/434,809

(22) Filed: May 9, 2003

(65) Prior Publication Data

US 2003/0220367 A1 Nov. 27, 2003

Related U.S. Application Data

(62) Division of application No. 09/810,436, filed on Mar. 14, 2001, now Pat. No. 6,693,098.

(60) Provisional application No. 60/247,129, filed on Nov. 10, 2000, provisional application No. 60/190,129, filed on Mar. 16, 2000.

(51) Int. Cl.
- *A61K 31/60* (2006.01)
- *A01N 37/36* (2006.01)
- *C07C 315/00* (2006.01)
- *C07C 229/00* (2006.01)
- *C07C 205/00* (2006.01)

(52) U.S. Cl. .................... 514/159; 514/163; 514/166; 562/430; 562/433; 562/434; 562/435; 562/437

(58) Field of Classification Search ............... 548/250; 562/465, 430, 433, 434, 437, 435; 514/159, 514/163, 166

See application file for complete search history.

(56) References Cited

U.S. PATENT DOCUMENTS

| | | | |
|---|---|---|---|
| 5,250,517 A | 10/1993 | Branca et al. | |
| 5,610,176 A | 3/1997 | Horwell et al. | |
| 5,981,755 A | 11/1999 | Horwell et al. | |
| 6,221,907 B1 | 4/2001 | Bernard et al. | |

OTHER PUBLICATIONS

Hcaplus 100:210433.*

* cited by examiner

*Primary Examiner*—James O. Wilson
*Assistant Examiner*—Binta Robinson
(74) *Attorney, Agent, or Firm*—Robert C. Hall

(57) ABSTRACT

This invention relates to compounds which are generally IP receptor antagonists and which are represented by Formula I:

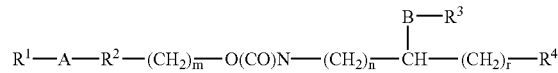

wherein:
- $R^1$, $R^2$, and $R^3$ are each independently in each occurrence aryl or heteroaryl;
- $R^4$ is —COOH or tetrazolyl;
- A, B, m, n, and r are as defined in the specification;
- or individual isomers, racemic or non-racemic mixtures of isomers, or pharmaceutically acceptable salts or solvates thereof. The invention further relates to pharmaceutical compositions containing such compounds, methods for their use as therapeutic agents, and processes for their preparation.

26 Claims, No Drawings

CARBOXYLIC ACID DERIVATIVES AS IP ANTAGONISTS

CROSS-REFERENCE TO RELATED INVENTIONS

This Application is a divisional of U.S. patent application Ser. No. 09/810,436 filed on Mar. 14, 2001 now U.S. Pat. No. 6,693,098. This application claims the benefit under Title 35 U.S.C. 119(e) of U.S. Provisional Applications Nos. 60/190,129 filed Mar. 16, 2000 and 60/247,129 filed Nov. 10, 2000, the disclosures of which are incorporated herein in their entirety.

FIELD OF THE INVENTION

This invention relates to carboxylic acid derivatives, and associated pharmaceutically acceptable salts and solvates thereof, associated pharmaceutical compositions, and methods for use as prostaglandin IP ($I_2$ or $PGI_2$) antagonists.

BACKGROUND OF THE INVENTION

Prostaglandins or prostanoids (PGs) are a group of bioactive compounds derived from membrane phospholipids and are formed from 20-carbon essential fatty acids containing three, four, or five double bonds, and a cyclopentane ring. They fall into several main classes designated by the letters D, E, F, G, H, or I, and they are distinguished by substitutions to the cyclopentane ring. The main classes are further subdivided by subscripts 1, 2, or 3, which reflect their fatty acid precursors. Thus, $PGI_2$ has a double ring structure, and the subscript 2 indicates that it is related to arachidonic acid.

$PGI_2$ (also known as prostacyclin) acts on platelets and blood vessels to inhibit aggregation and to cause vasodilation, and is thought to be important for vascular homeostasis. It has been suggested that $PGI_2$ may contribute to the antithrombogenic properties of the intact vascular wall. $PGI_2$ is also thought to be a physiological modulator of vascular tone that functions to oppose the actions of vasoconstrictors. The importance of these vascular actions is emphasized by the participation of $PGI_2$ in the hypotension associated with septic shock. Although prostaglandins do not appear to have direct effects on vascular permeability, $PGI_2$ markedly enhances edema formation and leukocyte infiltration by promoting blood flow in the inflamed region. Therefore, IP receptor antagonists may prevent conditions associated with excessive bleeding such as, but not limited to, hemophilia and hemorrhaging, may relieve hypotension related to septic shock, and may reduce edema formation.

Several in vivo analgesia studies in rodents suggest that $PGI_2$ plays a major role in the induction of hyperalgesia. Likewise, in vitro studies provide substantial evidence to suggest that "$PGI_2$-preferring" (IP) receptors act as important modulators of sensory neuron function (K. Bley et al, *Trends in Pharmacological Sciences* 1998, 19(4):141–147.). Since IP receptors in sensory neurons are coupled to activation of both adenylyl cyclase and phospholipase C, and hence, cAMP-dependent protein kinase and protein kinase C, these receptors can exert powerful effects on ion channel activity and thus neurotransmitter release. Evidence of a prominent role for IP receptors in inflammatory pain has been obtained from recent studies in transgenic mice lacking the IP receptor (T. Murata et al., *Nature* 1997, 388, 678–682).

In addition to being mediators of hyperalgesia, prostaglandins are known to be generated locally in the bladder in response to physiologic stimuli such as stretch of the detrusor smooth muscle, injuries of the vesical mucosa, and nerve stimulation (K. Anderson, *Pharmacological Reviews* 1993, 45(3), 253–308). $PGI_2$ is the major prostaglandin released from the human bladder. There are some suggestions that prostaglandins may be the link between detrusor muscle stretch produced by bladder filling and activation of C-fiber afferents by bladder distension. It has been proposed that prostaglandins may be involved in the pathophysiology of bladder disorders. Therefore, antagonists of prostaglandin IP receptors are expected to be useful in the treatment of such conditions.

Antagonists of IP receptors are also expected to find a utility in respiratory allergies wherein $PGI_2$ production in response to an allergen is present, or in respiratory conditions such as asthma.

Additional information relating to prostaglandins and their receptors is described in Goodman & Gillman's, *The Pharmacological Basis of Therapeutics*, ninth edition, McGraw-Hill, New York, 1996, Chapter 26, pages 601–616. Thus antagonists which can selectively treat the above mentioned conditions by acting on the IP receptor, are desirable.

DESCRIPTION OF THE RELATED ART

U.S. Pat. No. 5,250,517 assigned to F. Hoffmann-La Roche AG refers to certain N-hydroxyalkyl amino acid amide derivatives as inhibitors of renin for treating hypertension.

U.S. Pat. No. 5,610,176 and U.S. Pat. No. 5,981,755 assigned to Warner-Lambert refer to certain indole derivatives useful as tachykinin receptor antagonists.

EP published application EP 902018 assigned to F. Hoffmann-La Roche AG refers to certain 2-(arylphenyl)amino-imidazoline derivatives as IP antagonists.

PCT published application WO 97/19911 assigned to Thomae refers to certain amino acid derivatives as neuropeptide Y antagonists.

Japanese patent applications JP 06184086 and JP 06072985 refer to certain tetrazolylbiphenylmethylurea derivatives as angiotensin II antagonists.

German patent application DE 1934783 assigned to Farbenfabrik Bayer AG and French patent application FR 1554051 assigned to Ciba Ltd refer to the use of biphenylisopropoxycarbonyl derivatives as amino protecting reagents in the synthesis of peptides.

Bley et al., *Trends in Pharmacological Sciences* 1998, 19 (4), 141–147 refer to the role of IP prostanoid receptors in inflammatory pain.

Smith et al., *British Journal of Pharmacology* 1998, 124(3), 513–523 refer to characterization of prostanoid receptor-evoked responses in rat sensory neurons. Murata et al, *Nature* 1997, 388 (6643), 678–682 refer to altered pain perception and inflammatory response in mice lacking prostacyclin receptors.

Anderson et al., *Pharmacological Reviews* 1993, 45(3), 253–308 refer to Pharmacology of lower urinary tract smooth muscles and penile erectile tissues.

Coleman et al., *Pharmacological Review* 1994, 46(2), 205–229 refer to properties, distribution and structure of prostanoid receptors and their subtypes.

All publications, patents, and patent applications cited herein, whether supra or infra, are each hereby incorporated by reference in its entirety.

SUMMARY OF THE INVENTION

This invention relates to compounds comprising Formula I:

wherein:
- $R^1$, $R^2$, and $R^3$ are each independently in each occurrence optionally substituted aryl or optionally substituted heteroaryl;
- $R^4$ is —COOH or tetrazolyl;
- A is independently in each occurrence a single bond, —O(CH$_2$)$_p$—, —S(CH$_2$)$_p$—, —NR'(CH$_2$)$_p$—, —(CH$_2$)$_p$O—, —O(CH$_2$)$_p$O—, —(CH$_2$)$_p$O(CH$_2$)$_p$—, —(CH$_2$)$_n$CO(CH$_2$)$_n$—, —CON—, —NCO—, —(CH$_2$)$_p$—, —C=C—, or —C≡C—;
- R' is hydrogen or lower alkyl;
- B is independently in each occurrence —(CH$_2$)$_q$—, —CH$_2$O—, —CH$_2$S— or —CH$_2$N—;
- m, p, and q are each independently in each occurrence an integer from 1 to 3 inclusive;
- n and r are each independently in each occurrence an integer from 0 to 3 inclusive;
- or individual isomers, racemic or non-racemic mixtures of isomers, or pharmaceutically acceptable salts or solvates thereof.

In a preferred embodiment, $R^4$ is —COOH.

In a preferred embodiment, $R^4$ is —COOH, $R^1$ and $R^2$ are optionally substituted aryl; more preferably, $R^4$ is —COOH, $R^1$ and $R^2$ are phenyl optionally substituted with one or more substituents selected from lower alkyl, halo, hydroxyl, alkoxy, or cyano; and even more preferably $R^4$ is —COOH, $R^1$ and $R^2$ are phenyl optionally substituted with one or more substituents selected from lower alkyl, halo, hydroxyl, alkoxy, or cyano, and A is a single bond or —(CH$_2$)$_p$—.

In another preferred embodiment, $R^4$ is —COOH, $R^1$ and $R^2$ are phenyl optionally substituted with one or more substituents selected from lower alkyl, halo, hydroxyl, alkoxy, or cyano, $R^3$ is phenyl optionally substituted with one or more substituents selected from lower alkyl, halo, hydroxyl, alkoxy, or cyano, A is a single bond, m is 1, n and r are 0, and B is —CH$_2$—.

In another preferred embodiment, $R^4$ is —COOH, $R^1$ and $R^2$ are phenyl optionally substituted with one or more substituents selected from lower alkyl, halo, hydroxyl, alkoxy, or cyano, and A is —(CH$_2$)$_p$O—, —O(CH$_2$)$_p$—, or —(CH$_2$)$_p$O(CH$_2$)$_p$—; in a more preferred embodiment, $R^4$ is —COOH, $R^1$, $R^2$ and $R^3$ are phenyl optionally substituted with one or more substituents selected from lower alkyl, halo, hydroxyl, alkoxy, or cyano, A is —(CH$_2$)$_p$O—, —O(CH$_2$)$_p$—, or —(CH$_2$)$_p$O(CH$_2$)$_p$—, m is 1, n and r are 0, and B is —CH$_2$—.

In another preferred embodiment, $R^4$ is —COOH, $R^1$ is optionally substituted heteroaryl, and $R^2$ is optionally substituted aryl; more preferably, $R^4$ is —COOH, $R^1$ is optionally substituted heteroaryl, and $R^2$ is phenyl optionally substituted with one or more substituents selected from lower alkyl, halo, hydroxyl, alkoxy, or cyano; and even more preferably, $R^4$ is —COOH, $R^1$ is optionally substituted heteroaryl, $R^2$ is phenyl optionally substituted with one or more substituents selected from lower alkyl, halo, hydroxyl, alkoxy, or cyano, and A is a single bond.

In another preferred embodiment, $R^4$ is —COOH, $R^1$ is optionally substituted heteroaryl, $R^2$ is phenyl optionally substituted with one or more substituents selected from lower alkyl, halo, hydroxyl, alkoxy, or cyano, and A is —(CH$_2$)$_p$O— or —O(CH$_2$)$_p$—; more preferably, $R^4$ is —COOH, $R^1$ is optionally substituted indolyl, $R^2$ is phenyl optionally substituted with one or more substituents selected from lower alkyl, halo, hydroxyl, alkoxy, or cyano, and A is —O(CH$_2$)$_p$—, m is 1, n and r are 0, and B is —CH$_2$—.

In another preferred embodiment, $R^4$ is —COOH, $R^1$ and $R^2$ are optionally substituted heteroaryl; more preferably $R^4$ is —COOH, $R^1$ is optionally substituted heteroaryl, and $R^2$ is independently in each occurrence indolyl, indazolyl, benzoxazolyl, benzofuranyl, benzothiophenyl, benzimidazolyl, isoquinolinyl, or quinolinyl all optionally substituted; and even more preferably, $R^4$ is —COOH, $R^1$ is optionally substituted heteroaryl, $R^2$ is independently in each occurrence indolyl, indazolyl, benzoxazolyl, benzofuranyl, benzothiophenyl, benzimidazolyi, isoquinolinyl, or quinolinyl, all optionally substituted, and A is a single bond.

In another preferred embodiment, $R^4$ is —COOH, $R^1$ is optionally substituted heteroaryl, $R^2$ is independently in each occurrence indolyl, indazolyl, benzoxazolyl, benzofuranyl, benzothiophenyl, benzimidazolyl, isoquinolinyl, or quinolinyl, all optionally substituted, and A is —(CH$_2$)$_p$O— or —O(CH$_2$)$_p$—.

In another preferred embodiment, $R^4$ is -COOH, $R^1$ is optionally substituted aryl, and $R^2$ is optionally substituted heteroaryl; more preferably $R^4$ is —COOH, $R^1$ is phenyl optionally substituted with one or more substituents selected from lower alkyl, halo, hydroxyl, alkoxy, or cyano, and $R^2$ is independently in each occurrence indolyl, indazolyl, benzoxazolyl, benzofuranyl, benzothiophenyl, benzimidazolyl, isoquinolinyl, or quinolinyl, all optionally substituted; and more preferably $R^4$ is —COOH, $R^1$ is phenyl optionally substituted with one or more substituents selected from lower alkyl, halo, hydroxyl, alkoxy, or cyano, $R^2$ is independently in each occurrence indolyl, indazolyl, benzoxazolyl, benzofuranyl, benzothiophenyl, benzimidazolyl, isoquinolinyl, or quinolinyl, all optionally substituted, and A is a single bond or —(CH$_2$)$_p$—.

In another preferred embodiment, $R^4$ is —COOH, $R^1$ is phenyl optionally substituted with one or more substituents selected from lower alkyl, halo, hydroxyl, alkoxy, or cyano, $R^2$ is independently in each occurrence indolyl, indazolyl, benzoxazolyl, benzofuranyl, benzothiophenyl, benzimidazolyl, isoquinolinyl, or quinolinyl, all optionally substituted, and A is —(CH$_2$)$_p$O— or —O(CH$_2$)$_p$—; more preferably $R^4$ is —COOH, $R^1$ is phenyl optionally substituted with one or more substituents selected from lower alkyl, halo, hydroxyl, alkoxy, or cyano, $R^2$ is optionally substituted benzofuranyl, and A is —(CH$_2$)$_p$O— or —O(CH$_2$)$_p$—; even more preferably $R^4$ is —COOH, $R^1$ and $R^3$ are phenyl optionally substituted with one or more substituents selected from lower alkyl, halo, hydroxyl, alkoxy, or cyano, $R^2$ is optionally substituted benzofuranyl, A is —(CH$_2$)$_p$O— or —O(CH$_2$)$_p$—, m is 1, n and r are 0, and B is —CH$_2$—.

In another preferred embodiment, $R^4$ is —COOH, $R^1$ is phenyl optionally substituted with one or more substituents selected from lower alkyl, halo, hydroxyl, alkoxy, or cyano, $R^2$ is optionally substituted benzofuranyl, and A is a single bond or —(CH$_2$)$_p$—; more preferably $R^4$ is —COOH, $R^1$ and $R^3$ are phenyl optionally substituted with one or more substituents selected from lower alkyl, halo, hydroxyl, alkoxy, or cyano, $R^2$ is optionally substituted benzofuranyl, and A is a single bond, m is 1, n and r are 0, and B is —CH$_2$—.

In another preferred embodiment, $R^4$ is —COOH, $R^1$ is phenyl optionally substituted with one or more substituents selected from lower alkyl, halo, hydroxyl, alkoxy, or cyano, $R^2$ is optionally substituted benzoxazolyl, and A is a single bond or —$(CH_2)_p$—; more preferably $R^1$ and $R^3$ are phenyl optionally substituted with one or more substituents selected from lower alkyl, halo, hydroxyl, alkoxy, or cyano, $R^2$ is optionally substituted benzoxazolyl, A is a single bond, m is 1, n and r are 0, and B is —$CH_2$—.

In another preferred embodiment, $R^4$ is —COOH, $R^1$ is phenyl optionally substituted with one or more substituents selected from lower alkyl, halo, hydroxyl, alkoxy, or cyano, $R^2$ is optionally substituted benzoxazolyl, and A is —$(CH_2)_pO$— or —$O(CH_2)_p$—; more preferably $R^4$ is —COOH, $R^1$ and $R^3$ are phenyl optionally substituted with one or more substituents selected from lower alkyl, halo, hydroxyl, alkoxy, or cyano, $R^2$ is optionally substituted benzoxazolyl, A is —$(CH_2)_pO$— or —$O(CH_2)_p$—; m is 1, n and r are 0, and B is —$CH_2$—.

In another preferred embodiment, the compound is 2-(biphenyl-4-ylmethoxycarbonylamino)-3-phenyl-propionic acid; (R)-2-(4-phenoxymethyl-benzyloxycarbonylamino)-3-phenyl-propionic acid; (R)-2-(5-phenyl-benzofuran-2-ylmethoxycarbonylamino)-3-phenyl-propionic acid; (R)-2-(4-phenethyloxy-benzyloxycarbonylamino)-3-phenyl-propionic acid; (R)-2-(2-phenyl-benzofuran-5-ylmethoxycarbonylamino-3-phenyl propionic acid; (R)-2-(5-thiophen-3-yl-benzofuran-2-ylmethoxycarbonylamino)-3-phenyl-propionic acid; 2-[4-(1H-indol-4-yloxymethyl)-benzyloxycarbonylamino]-3-phenyl-propionic acid; (R)-2-(5-phenyl-benzofuran-3-ylmethoxycarbonylamino)-3-phenyl-propionic acid; 2-[4-(2-Fluoro-phenoxymethyl)-benzyloxycarbonylamino]-3-phenyl-propionic acid; 2-(3-fluoro-4-phenoxymethyl-benzyloxycarbonylamino)-3-phenyl-propionic acid; 2-[4-(3-fluoro-phenoxymethyl)-benzyloxycarbonylamino]-3-phenyl-propionic acid; (R)-2-[5-(4-fluoro-phenyl)-benzofuran-2-ylmethoxycarbonylamino]-3-phenyl-propionic acid; 2-(biphenyl-4-methoxycarbonyl)amino-3-(3-indolyl)propionic acid;3-(3-benzenesulfonylamino-phenyl)-2-(5-phenyl-benzofuran-2-ylmethoxycarbonylamino)-propionic acid; 3-(3-benzenesulfonylamino-phenyl)-2-(4-phenoxymethyl-benzyloxycarbonylamino)-propionic acid; 3-(3-benzenesulfonylamino-phenyl)-2-(biphenyl-4-ylmethoxycarbonylamino)-propionic acid; (S)-2-phenyl-2-(5-phenyl-1H-indol-2-ylmethoxycarbonylamino)-propionic acid; (R)-2-[5-(4-chloro-phenyl)-benzofuran-2-ylmethoxycarbonylamino]-3-phenyl-propionic acid; (R)-2-[5-(3-fluoro-phenyl)-benzofuran-2-ylmethoxycarbonylamino]-3-phenyl-propionic acid; (R)-2-[5-(4-methoxy-phenyl)-benzofuran-2-ylmethoxycarbonylamino]-3-phenyl-propionic acid; (R)-3-(4-fluoro-phenyl)-2-[5-(4-fluoro-phenyl)-benzofuran-2-ylmethoxycarbonylamino]-propionic acid; (R)-3-(4-fluoro-phenyl)-2-(5-phenyl-benzofuran-2-ylmethoxycarbonylamino)-propionic acid; (R)-2-[5-(4-methyl-phenyl)-benzofuran-2-ylmethoxycarbonylamino]-3-phenyl-propionic acid; (R)-2-(2-benzyl-benzofuran-5-ylmethoxycarbonylamino)-3-phenyl-propionic acid; (R)-3-phenyl-2-(5-phenyl-benzoxazol-2-ylmethoxycarbonylamino) propionic acid; (R)-3-phenyl-2-(2-phenyl-benzoxazol-5-ylmethoxycarbonylamino)-propionic acid; (R)-2-[5-(1H-indol-4-yl)-benzofuran-2-ylmethoxycarbonylamino]-3-phenyl-propionic acid; 2-[4-(1H-indol-4-ylmethoxy)-benzyloxycarbonylamino]-3-phenyl-propionic acid; 2-(4-benzyloxybenzylcarbonylamino)-3-phenyl-propionic acid; 2-[4-(1H-indol-5-ylmethoxy)-benzyloxycarbonylamino]-3-phenyl-propionic acid; (R)-2-(5-benzo[1,3]dioxol-5-yl-benzofuran-2-ylmethoxycarbonylamino)-3-phenyl-propionic acid; 2-[4-(1H-indol-4-yloxymethyl)-benzyloxycarbonylamino]-3-phenyl-propionic acid (R)-2-[5-(3-cyano-phenyl)-benzofuran-2-ylmethoxycarbonylamino]-3-phenyl-propionic acid; (R)-3-phenyl-2-(5-phenyl-2,3-dihydro-benzofuran-2-ylmethoxycarbonylamino)-propionic acid; (R)-3-(4-fluoro-phenyl)-2-(5-pyridin-3-yl-benzofuran-2-ylmethoxycarbonylamino)-propionic acid; (R)-2-[2-(4-fluoro-phenyl)-benzoxazol-5-ylmethoxycarbonylamino]-3-phenyl-propionic acid (R)-2-[5-(3-cyano-phenyl)-benzofuran-2-ylmethoxycarbonylamino]-3-(4-fluoro-phenyl)-propionic acid; (R)-2-[5-(3,5-difluoro-phenyl)-benzofuran-2-ylmethoxycarbonylamino]-3-phenyl-propionic acid; (R)-2-[5-(2-fluoro-phenyl)-benzofuran-2-ylmethoxycarbonylamino]-3-phenyl-propionic acid; (R)-2-[5-(2,3-difluoro-phenyl)-benzofuran-2-ylmethoxycarbonylamino]-3-phenyl-propionic acid; (R)-3-(4-fluoro-phenyl)-2-[5-(2-fluoro-phenyl)-benzofuran-2-ylmethoxycarbonylamino]-propionic acid; (R)-2-[5-(2-chloro-phenyl)-benzofuran-2-ylmethoxycarbonylamino]-3-(4-fluoro-phenyl)-propionic acid; (R)-2-(5-benzo[1,3]dioxol-5-yl-benzofuran-2-ylmethoxycarbonylamino)-3-(4-fluoro-phenyl)-propionic acid; (R)-3-(4-chloro-phenyl)-2-[5-(4-fluoro-phenyl)-benzofuran-2-ylmethoxycarbonylamino]-propionic acid; (R)-2-(5-benzo[1,3]dioxol-4-yl-benzofuran-2-ylmethoxycarbonylamino)-3-phenyl-propionic acid; (R)-2-[2-(3-cyano-phenyl)-benzoxazol-5-ylmethoxycarbonylamino]-3-(4-fluoro-phenyl-propionic acid; (R)-3-(4-bromo-phenyl)-2-[5-(4-fluoro-phenyl)-benzofuran-2-ylmethoxycarbonylamino]-propionic acid; (R)-3-(4-chloro-phenyl)-2-(5-phenyl-benzofuran-2-ylmethoxycarbonylamino)-propionic acid; (R)-3-(3-fluoro-phenyl)-2-[5-(4-fluoro-phenyl)-benzofuran-2-ylmethoxycarbonylamino]-propionic acid; (R)-3-(3-fluoro-phenyl)-2-(5-phenyl-benzofuran-2-ylmethoxycarbonylamino)-propionic acid; (R)-2-[5-(2,5-difluoro-phenyl)-benzofuran-2-ylmethoxycarbonylamino]-3-phenyl-propionic acid; (R)-2-[5-(3,4-difluoro-phenyl)-benzofuran-2-ylmethoxycarbonylamino]-3-phenyl-propionic acid; (R)-2-[5-(2,5-difluoro-phenyl)-benzofuran-2-ylmethoxycarbonylamino]-3-(4-fluoro-phenyl)-propinic acid; (R)-2-[5-(3,4-difluoro-phenyl)-benzofuran-2-ylmethoxycarbonylamino]-3-(4-fluoro-phenyl)-propionic acid; (R)-2-[5-(3,5-difluoro-phenyl)-benzofuran-2-ylmethoxycarbonylamino]-3-(4-fluoro-phenyl)-propionic acid; (R)-3-phenyl-2-(2-phenyl-quinolin-6-ylmethoxycarbonylamino)-propionic acid; (R)-2-[5-(1H-indol-5-yl)-benzofuran-2-ylmethoxycarbonylamino]-3-phenyl-propionic acid; (R)-2-[2-(1H-indol-4-yl)-benzoxazol-5-ylmethoxycarbonylamino]-3-phenyl-propionic acid; (R)-2-[2-(3,5-difluoro-phenyl)-benzoxazol-5-ylmethoxycarbonylamino]-3-phenyl-propionic acid; 2-(5-phenyl-benzofuran-2-ylmethoxycarbonylamino)-3-pyridin-4-yl-propionic acid; and 2-(5-phenyl-benzofuran-2-ylmethoxycarbonylamino)-3-pyridin-3-yl-propionic acid; or an individual isomer, racemic or non-racemic mixture of isomers, or a pharmaceutically acceptable salt or solvate thereof.

Another aspect of the invention relates to pharmaceutical compositions suitable for administration to a subject, comprising as an ingredient a therapeutically effective amount of at least one compound of Formula I, or individual isomers, racemic or non-racemic mixtures of isomers, or pharmaceutically acceptable salts or solvates thereof, in admixture with at least one pharmaceutically acceptable carrier; more preferably the at least one compound is suitable for administration to a subject having a disease state which is alleviated by treatment with an IP receptor modulator, and in an even more preferably wherein the at least one compound is suitable for administration to a subject having a disease state which is alleviated by treatment with an IP receptor antagonist.

An additional aspect of the invention relates to methods of treatment comprising administering to a subject in need of such treatment, a therapeutically effective amount of at least one compound of Formula I or individual isomers, racemic or non-racemic mixtures of isomers, or pharmaceutically acceptable salts or solvates thereof.

In a preferred embodiment, the invention further relates to methods of treatment comprising administering to a subject in need of such treatment, a therapeutically effective amount of a composition containing at least one compound of Formula I or individual isomers, racemic or non-racemic mixtures of isomers, or pharmaceutically acceptable salts or solvates thereof.

In a preferred embodiment, the invention further relates to methods for treating a subject having a disease state that is alleviated by treatment with an IP receptor antagonist, which comprises administering to such a subject a therapeutically effective amount of at least one compound of Formula I, or individual isomers, racemic or non-racemic mixtures of isomers, or pharmaceutically acceptable salts or solvates thereof.

In a preferred embodiment, the disease state is associated with the urinary tract, pain, inflammation, respiratory states, edema formation, or hypotensive vascular diseases that can be alleviated by treatment with an IP receptor antagonist.

In a preferred embodiment, the disease state is associated with the lower urinary tract; more preferably the disease state comprises bladder disorders associated with bladder outlet obstruction and urinary incontinence conditions such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, pelvic pain syndrome, prostatodynia, cystitis, or idiophatic bladder hypersensitivity.

In another preferred embodiment, the disease state is pain, more preferably the disease state comprises inflammatory pain, neuropathic pain, cancer pain, acute pain, chronic pain, surgical pain, dental pain, premenstrual pain, visceral pain, pain due to burns, migraine or cluster headaches, neuralgias, post traumatic injuries, pain associated with functional bowel disorders such as irritable bowel syndrome, hyperalgesia, or complex regional syndromes.

In another preferred embodiment, the disease state is inflammation; more preferably the disease state comprises inflammation from bacterial, fungal or viral infections, rheumatoid arthritis, osteoarthritis, surgery, bladder infection or idiopathic bladder inflammation, pelvic hypersensitivity, urethritis, prostatitis, prostatodynia or conjunctivitis.

In another embodiment, the disease state comprises respiratory states from allergies or asthma.

In another embodiment, the disease state comprises edema formation.

In another embodiment, the disease state comprises states associated with hypotensive vascular diseases, preferably the disease state comprises relief of hypotension associated with septic shock.

Another aspect of the invention relates to a process which comprises reacting a compound having a general formula

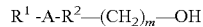

with a compound of general formula

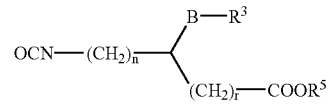

followed by hydrolysis to provide a compound of the general formula

wherein $R^5$ is $C_{1-4}$-alkyl, $R^4$ is COOH, and $R^1$, $R^2$, $R^3$, A, B, m, n, and r are as defined herein.

In yet another aspect, the invention relates to a process which comprises reacting a compound having a general formula

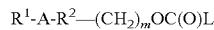

wherein L is a leaving group, with a compound of general formula

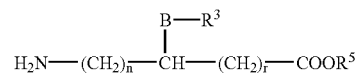

followed by hydrolysis to provide a compound of the general formula

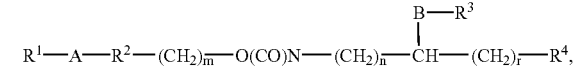

wherein $R^5$ is $C_{1-4}$-alkyl, $R^4$ is COOH, and $R^1$, $R^2$ $R^3$ A, B, m, n, and r are as defined herein.

In yet another aspect, the invention relates to a process which-comprises reacting a compound having a general formula

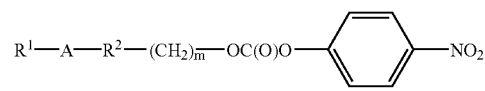

with a compound of general formula

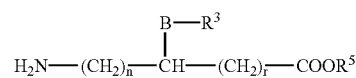

followed by hydrolysis to provide a compound of the general formula

$$R^1—A—R^2—(CH_2)_{\overline{m}}—O(CO)N—(CH_2)_{\overline{n}}—\overset{\overset{B—R^3}{|}}{CH}—(CH_2)_r—R^4,$$

wherein $R^5$ is $C_{1-4}$-alkyl, $R^4$ is COOH, and $R^1$, $R^2$, $R^3$, A, B, m, n, and r are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an" and "the" include plural referents unless the context clearly dictates otherwise.

"Alkyl" means the monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkylene" means the divalent linear or branched saturated hydrocarbon radical, consisting solely of carbon and hydrogen atoms, having from one to six carbons inclusive, unless otherwise indicated. Examples of alkylene radicals include, but are not limited to, methylene, ethylene, propylene, 2-methyl-propylene, butylene, 2-ethylbutylene, and the like.

"Alkoxy" means the radical —O—R, wherein R is a lower alkyl radical as defined herein. Examples of alkoxy radicals include, but are not limited to, methoxy, ethoxy, isopropoxy, and the like.

"Alkoxycarbonyl" means the radical R—O—C(O)—, wherein R is a lower alkyl radical as defined herein. Examples of alkoxycarbonyl radicals include, but are not limited to, methoxycarbonyl, ethoxycarbonyl, sec-butoxycarbonyl, and the like.

"Aryl" means the monovalent or divalent aromatic hydrocarbon radical consisting of one individual ring, or one or more fused rings in which at least one ring is aromatic in nature, which can optionally be substituted with one or more, preferably one or two substituents selected independently from hydroxy, cyano, lower alkyl, lower alkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, arylcarbonylamino, alkylaminocarbonyl, arylaminocarbonyl, alkylsulfonylamino, or arylsulfonylamino and/or trifluoromethyl unless otherwise indicated. Alternatively two adjacent atoms of the aryl ring may be substituted with a methylenedioxy or ethylenedioxy group. Examples of aryl radicals include, but are not limited to, phenyl, naphthyl, biphenyl, 1,3, -benzodioxolyl, 3-benzenesulfonylamino-phenyl, 1-phenyl-methanoyl-amino-phenyl; acetylaminophenyl, 3-nitrophenyl, tert-butyl phenyl, indanyl, 4-fluoro-phenyl, anthraquinolyl, and the like.

"Arylalkyl" means the radical R'R"-, wherein R' is an aryl radical as defined herein, and R" is an alkyl radical as defined herein. Examples of arylalkyl radicals include, but are not limited to, benzyl, phenylethyl, 3-phenylpropyl, and the like.

"Heteroaryl" means the monovalent or divalent aromatic carbocyclic radical having one or more rings incorporating one, two, or three heteroatoms within the ring (chosen from nitrogen, oxygen, or sulfur) which can optionally be substituted with one or more substituents selected from preferably one or two substituents selected independently from hydroxy, cyano, lower alkyl, lower alkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, arylcarbonylamino, alkylaminocarbonyl, arylaminocarbonyl, alkylsulfonylamino, or arylsulfonylamino and/or trifluoromethyl unless otherwise indicated. Examples of heteroaryl radicals include, but are not limited to, imidazolyl, oxazolyl, thiazolyl, pyrazinyl, pyridazinyl, pyrazinyl, thiophenyl, furanyl, pyrimidinyl, pyridinyl , quinolin-2,6-diyl, quinolinyl, isoquinolinyl, 1,3-benzodioxole, benzofuranyl, benzofuran-2, 5-diyl, benzofuran-3,5-diyl, 2,3-dihydrobenzofuran-2,5-diyl, benzothiophen-2,5-diyl, benzothiopyranyl, benzimidazol-2,5-diyl, benzoxazolyl-2,5-diyl, benzothiazolyl, benzopyranyl, indazolyl, indol-5-yl, indol-4-yl, indol-1-yl, indol-2,5-diyl, N-alkyl-indolyl, isoindolyl, quinolinyl, isoquinolinyl, naphtyridinyl, and the like.

"Halo" means the radical fluoro, bromo, chloro, and/or iodo.

"Amino" means the radical —NR'R", wherein R' and R" are hydrogen or a lower alkyl radical as defined herein. Examples of amino radicals include, but are not limited to —NH$_2$, methylamino, diethylamino(1-ethylethyl)amino, and the like.

"Alkylsulfonyl" means the radical —SO$_2$R, wherein R is a lower alkyl radical as defined herein. Examples of alkylsulfonyl radicals include, but are not limited to, methylsulfonyl, (1-ethylethyl)sulfonyl, and the like.

"Arylsulfonyl" means the radical —SO$_2$R, wherein R is an aryl radical as defined herein. Examples of arylsulfonyl radicals include, but are not limited to, phenylsulfonyl, naphthylsulfonyl, and the like.

"Alkylaminosulfonyl" means the radical —SO$_2$NHR, wherein R is a lower alkyl radical as defined herein. Examples of alkylaminosulfonyl radicals include, but are not limited to, methylaminosulfonyl, ethylaminosulfonyl, and the like.

"Arylaminosulfonyl" means the radical —SO$_2$NHR, wherein R is an aryl radical as defined herein. Examples of arylaminosulfonyl radicals include, but are not limited to, phenyl aminosulfonyl, naphthylaminosulfonyl, and the like.

"Alkylsulfonylamino" means the radical —NHSO$_2$R, wherein R is a lower alkyl radical as defined herein. Examples of alkylsulfonylamino radicals include, but are not limited to, methylsulfonylamino, propylsulfonylamino, and the like.

"Arylsulfonylamino" means the radical —NHSO$_2$R, wherein R is an aryl radical as defined herein. Examples of arylsulfonylamino radicals include, but are not limited to, phenylsulfonylamino, naphthylsulfonylamino, and the like.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotective reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters.

"Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are nonsuperimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956,12, 81; Cahn, *J. Chem. Educ.* 1964, 41,116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-lngold-Prelog rules.

"Atropic isomers" means the isomers owing their existence to restricted rotation caused by hindrance of rotation of large groups about a central bond.

"Substantially pure" means at least about 90 mole percent, more preferably at least about 95 mole percent, and most preferably at least about 98 mole percent of the desired enantiomer or stereoisomer is present compared to other possible configurations.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, (4-hydroxybenzoyl) benzoic acid, camphorsulfonic acid, p-chlorobenzenesulfonic acid, cinnamic acid, citric acid, cylcopentanepropionic acid, ethanesulfonic acid, 1,2-ethanedisulfonic acid, fumaric acid, glucoheptonic acid, gluconic acid, glutamic acid, glycolic acid, hexanoic acid, heptanoic-acid, hydroxynaphtoic acid, 2-hydroxyethanesulfonic acid, lactic acid, lauryl sulfuric acid, maleic acid, malic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-naphthalenesulfonic acid, oxalic acid, 3-phenyl-propionic acid, propionic acid, pyruvic acid, salicylic acid, stearic acid, succinic acid, tartaric acid, tertiary butylacetic acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, dicyclohexylamine, ethanolamine, N-methylglucamine, triethanolamine, tromethamine, t-butylamine and the like. Acceptable inorganic bases include aluminum hydroxide, calcium hydroxide, potassium hydroxide, sodium carbonate and sodium hydroxide.

The preferred pharmaceutically acceptable salts are the salts formed from sodium, potassium, lithium, t-butylamine, or dicyclohexylamine.

It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve easy of formulation, or provide site-specific delivery of the compound. Reference to a compound herein includes prodrug forms of a compound.

"Subject" means mammals and non-mammals. Mammals means any member of the Mammalia class including, but not limited to humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors. "Pharmacological effect" as used herein encompasses effects produced in the subject that achieve the intended purpose of a therapy. A pharmacological effect means that the indications of the subject being treated are prevented, alleviated, or reduced.

"Disease state" means any disease, condition, symptom, or indication.

"Treating" or "treatment" of a disease state includes:
 (1) preventing the disease state, i.e. causing the clinical symptoms of the disease state not to develop in a subject that may be exposed to or predisposed to the disease state, but does not yet experience or display symptoms of the disease state.
 (2) inhibiting the disease state, i.e., arresting the development of the disease state or its clinical symptoms, or
 (3) relieving the disease state, ie., causing temporary or permanent regression of the disease state or its clinical symptoms.

"Modulator" means a molecule, such as a compound, that interacts with a target. The interactions include, but are not limited to, agonist, antagonist, and the like, as defined herein.

"Antagonist" means a molecule such as a compound, a drug, an enzyme inhibitor, or a hormone, that diminishes or prevents the action of another molecule or receptor site.

"Trauma" means any wound or injury. Trauma can produce, for example, acute and/or chronic pain, inflammatory pain, and neuropathic pain.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W. B. Saunders Company, Philadelphia, Pa.). The goal of treatment of pain is to reduce the degree of severity of pain perceived by a treatment subject.

"Neuropathic pain" means the pain resulting from functional disturbances and /or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Hyperalgesia" means the pain that results from an excessive sensitiveness or sensitivity.

"Allodynia" means the pain that results from a non-noxious stimulus to the skin. Examples of allodynia include, but are not limited to, cold allodynia, tactile allodynia, and the like.

"Complex regional pain syndromes" means the pain that includes, but is not limited to, reflex sympathetic dystrophy, causalgia, sympathetically maintained pain, and the like.

"Causalgia" means the burning pain, often accompanied by trophic skin changes, due to injury of a peripheral nerve.

"Nociception" means the pain sense. "Nociceptor" means the structure that mediates nociception. Nociception may be the result of a physical stimulus, such as, mechanical, electrical, thermal, or a chemical stimulus. Most nociceptors are in either the skin or the viscera walls.

"Analgesia" means the relief of pain without the loss of consciousness. An "analgesic" is an agent or drug useful for relieving pain, again without the loss of consciousness.

"Disorders of the urinary tract" or "uropathy" used interchangeably with "symptoms of the urinary tract" means the pathologic changes in the urinary tract. Examples of urinary tract disorders include, but are not limited to, bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, pelvic pain syndrome, prostatodynia, cystitis, and idiophatic bladder hypersensitivity, and the like.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy (BPH), urethral stricture disease, tumors and the like. It is usually symptomatically manifested as obstructive (low flow rates, difficulty in initiating urination, and the like), and irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to pelvic pain, interstitial (cell) cystitis, prostadynia, prostatis, vulvadynia, urethritis, orchidalgia, and the like. It is symptomatically manifested as pain, inflammation or discomfort referred to the pelvic region, and usually includes symptoms of overactive bladder.

Throughout the application the following abbreviations are used with the following meanings:

| | |
|---|---|
| AcOH | Acetic acid |
| AIBN | Azodiisobutyronitrile |
| Alk | Alkyl |
| 9-BBN | 9-Borabicyclo[3.3.1]nonane |
| DMAP | 4-Dimethylaminopyridine |
| DMF | N,N-Dimethylformamide |
| DMSO | Dimethylsulfoxide |
| EtOAc | Ethyl acetate |
| Hal | Halo |
| MeOH | Methanol |
| NBS | N-Bromosuccinimide |
| TBS | tert-Butyldimethylsilyl |
| TFA | Trifluoroacetic acid |
| THF | Tetrahydrofuran |

Nomenclature

In general, the nomenclature used in this Application is based on AUTONOM™ v.4.0, a Beilstein Institute computerized system for the generation of IUPAC systematic nomenclature.

For example, a compound of Formula I wherein $R^1$, $R^2$, and $R^3$ are phenyl, $R^4$ is —COOH, A is —OCH$_2$—, B is —CH$_2$—, m and n are 1, and r is 0 is named 2-(4-phenoxymethyl-benzyloxycarbonylamino)-3-phenyl-propionic acid.

Preferred Compounds

Among compounds of the present invention set forth in the Summary of the Invention, certain compounds of Formula I, or individual isomers, racemic or non-racemic mixtures of isomers, or pharmaceutically acceptable salts or solvates thereof are preferred.

$R^1$ is independently in each occurrence preferably optionally substituted aryl or optionally substituted heteroaryl, and even more preferably optionally substituted phenyl or optionally substituted indolyl.

$R^2$ is independently in each occurrence preferably optionally substituted aryl or optionally substituted heteroaryl, more preferably optionally substituted phenyl or optionally substituted heteroaryl, and even more preferably optionally substituted indolyl, optionally substituted benzofuranyl or optionally substituted benzoxazolyl.

$R^3$ is independently in each occurrence preferably optionally substituted aryl or optionally substituted heteroaryl, more preferably optionally substituted phenyl or optionally substituted indolyl or pyridyl, and even more preferably optionally substituted phenyl.

$R^4$ is —COOH or tetrazolyl, more preferably —COOH.
m, p and q are preferably 1 to 3; and more preferably 1.
n and r are preferably 0 to 3, and more preferably 0.

A is independently in each occurrence a single bond, —O(CH$_2$)$_p$—, —S(CH$_2$)$_p$—, —NR'(CH$_2$)$_p$—, —(CH$_2$)$_p$O—, —O(CH$_2$)$_p$O—, —(CH$_2$)$_p$O(CH$_2$)$_p$—, —(CH$_2$)$_n$CO(CH$_2$)$_n$—, —CON—, —NCO—; —(CH$_2$)$_p$—, —C=C—, or —C≡C—; more preferably a single bond, —(CH$_2$)$_p$—, —O(CH$_2$)$_p$—, —(CH$_2$)$_p$O—, or —(CH$_2$)$_p$O(CH$_2$)$_p$—, and even more preferably —O(CH$_2$)$_p$—, —(CH$_2$)$_p$O— or a single bond.

B is independently in each occurrence —(CH$_2$)$_q$—, —CH$_2$O—, —CH$_2$S— or —CH$_2$N—; more preferably —(CH$_2$)$_q$—, and even more preferably —CH$_2$—.

Other preferred compounds of the present invention include the pharmaceutically acceptable salts of the compounds of the present invention wherein the pharmaceutically acceptable salts are formed from an alkali metal, or an amine; more preferably the salts are formed from sodium, potassium, lithium, t-butylamine or dicyclohexylamine.

Exemplary particularly preferred compounds include: 2-(biphenyl-4-ylmethoxycarbonylamino)-3-phenyl-propionic acid; (R)-2-(4-phenoxymethyl-benzyloxycarbonylamino)-3-phenyl-propionic acid; (R)-2-(5-phenyl-benzofuran-2-ylmethoxycarbonylamino)-3-phenyl-propionic acid; (R)-2-(4-phenethyloxy-benzyloxycarbonylamino)-3-phenyl-propionic acid; (R)-2-(2-phenyl-benzofuran-5-ylmethoxycarbonylamino)-3-phenyl propionic acid; (R)-2-(5-thiophen-3-yl-benzofuran-2-ylmethoxycarbonylamino)-3-phenyl-propionic acid; 2-[4-(1H-indol-4-yloxymethyl)-benzyloxycarbonylamino]-3-phenyl-propionic acid; (R)-2-(5-phenyl-benzofuran-3-ylmethoxycarbonylamino)-3-phenyl-propionic acid; 2-[4-(2-Fluoro-phenoxymethyl)-benzyloxycarbonylamino]-3-phenyl-propionic acid; 2-(3-fluoro-4-phenoxymethyl-benzyloxycarbonylamino)-3-phenyl-propionic acid; 2-[4-(3-fluoro-phenoxymethyl)-benzyloxycarbonylamino]-3-phenyl-propionic acid; (R)-2-[5-(4-fluoro-phenyl)-benzofuran-2-ylmethoxycarbonylamine]-3-phenyl-propionic acid; 2-(biphenyl-4-methoxycarbonyl)amino-3-(3-indolyl)propionic acid; 3-(3-benzenesulfonylamino-phenyl)-2-(5-phenyl-benzofuran-2-ylmethoxycarbonylamino)-propionic acid; 3-(3-benzenesulfonylamino-phenyl)-2-(4-phenoxymethyl-benzyloxycarbonylamino)-propionic acid; 3-(3-benzenesulfonylamino-phenyl)-2-(biphenyl-4-ylmethoxycarbonylamino)-propionic acid; (S)-2-phenyl-2-(5-phenyl-1H-indol-2-ylmethoxycarbonylamino)-propionic acid; (R)-2-[5-(4-chloro-phenyl)-benzofuran-2-ylmethoxycarbonylamino]-3-phenyl-propionic acid; (R)-2-[5-(3-fluoro-phenyl)-benzofuran-2-ylmethoxycarbonylamino]-3-phenyl-propionic acid; (R)-2-[5-(4-methoxy-phenyl)-benzofuran-2-ylmethoxycarbonylamino]-3-phenyl-propionic acid; (R)-3-(4-fluoro-phenyl)-2-[5-(4-fluoro-phenyl)-benzofuran-2-ylmethoxycarbonylamino]-propionic acid; (R)-3-(4-fluoro-phenyl)-2-(5-phenyl-benzofuran-2-ylmethoxycarbonylamino)-propionic acid; (R)-2-[5-(4-methyl-phenyl)-benzofuran-2-ylmethoxycarbonylamino]-3-phenyl-propionic acid; (R)-2-(2-benzyl-benzofuran-5-ylmethoxycarbonylamino)-3-phenyl-propionic acid; (R)-3-phenyl-2-(5-phenyl-benzoxazol-2-ylmethoxycarbonylamino) propionic acid; (R)-3-phenyl-2-(2-phenyl-benzoxazol-5-ylmethoxycarbonylamino)-propionic acid; (R)-2-[5-(1H-indol-4-yl)-benzofuran-2-ylmethoxycarbonylamino]-3-phenyl-propionic acid; 2-[4-

(1H-indol-4-ylmethoxy)-benzyloxycarbonylamino]-3-phenyl-propionic acid; 2-(4-benzyloxybenzylcarbonylamino)-3-phenyl-propionic acid; 2-[4-(1H-indol-5-ylmethoxy)-benzyloxycarbonylamino]-3-phenyl-propionic acid; (R)-2-(5-benzo[1,3]dioxol-5-yl-benzofuran-2-ylmethoxycarbonylamino)-3-phenyl-propionic acid; 2-[4-(1H-indol-4-yloxymethyl)-benzyloxycarbonylamino]-3-phenyl-propionic acid (R)-2-[5-(3-cyano-phenyl)-benzofuran-2-ylmethoxycarbonylamino]-3-phenyl-propionic acid; (R)-3-phenyl-2-(5-phenyl-2,3-dihydro-benzofuran-2-ylmethoxycarbonylamino)-propionic acid; (R)-3-(4-fluoro-phenyl)-2-(5-pyridin-3-yl-benzofuran-2-ylmethoxycarbonylamino)-propionic acid; (R)-2-[2-(4-fluoro-phenyl)-benzoxazol-5-ylmethoxycarbonylamino]-3-phenyl-propionic acid; (R)-2-[5-(3-cyano-phenyl)-benzofuran-2-ylmethoxycarbonylamino]-3-(4-fluoro-phenyl)-propionic acid;

(R)-2-[5-(3,5-difluoro-phenyl)-benzofuran-2-ylmethoxycarbonylamino]-3-phenyl-propionic acid; (R)-2-[5-(2-fluoro-phenyl)-benzofuran-2-ylmethoxycarbonylamino]-3-phenyl-propionic acid; (R)-2-[5-(2,3-difluoro-phenyl)-benzofuran-2-ylmethoxycarbonylamino]-3-phenyl-propionic acid; (R)-3-(4-fluoro-phenyl)-2-[5-(2-fluoro-phenyl)-benzofuran-2-ylmethoxycarbonylamino]-propionic acid; (R)-2-[5-(2-chloro-phenyl)-benzofuran-2-ylmethoxycarbonylamino]-3-(4-fluoro-phenyl)-propionic acid; (R)-2-(5-benzo[1,3]dioxol-5-yl-benzofuran-2-ylmethoxycarbonylamino)-3-(4-fluoro-phenyl)-propionic acid; (R)-3-(4-chloro-phenyl)-2-[5-(4-fluoro-phenyl)-benzofuran-2-ylmethoxycarbonylamino]-propionic acid; (R)-2-(5-benzo[1,3]dioxol-4-yl-benzofuran-2-ylmethoxycarbonylamino)-3-phenyl-propionic acid; (R)-2-[2-(3-cyano-phenyl)-benzoxazol-5-ylmethoxycarbonylamino]-3-(4-fluoro-phenyl)-propionic acid; (R)-3-(4-bromo-phenyl)-2-[5-(4-fluoro-phenyl)-benzofuran-2-ylmethoxycarbonylamino]-propionic acid; (R)-3-(4-chloro-phenyl)-2-(5-phenyl-benzofuran-2-ylmethoxycarbonylamino)-propionic acid; (R)-3-(3-fluoro-phenyl)-2-[5-(4-fluoro-phenyl)-benzofuran-2-ylmethoxycarbonylamino]-propionic acid; (R)-3-(3-fluoro-phenyl)-2-(5-phenyl-benzofuran-2-ylmethoxycarbonylamino)-propionic acid; (R)-2-[5-(2,5-difluoro-phenyl)-benzofuran-2-ylmethoxycarbonylamino]-3-phenyl-propionic acid; (R)-2-[5-(3,4-difluoro-phenyl)-benzofuran-2-ylmethoxycarbonylamino]-3-phenyl-propionic acid; (R)-2-[5-(2,5-difluoro-phenyl)-benzofuran-2-ylmethoxycarbonylamino]-3-(4-fluoro-phenyl)-propionic acid; (R)-2-[5-(3,4-difluoro-phenyl)-benzofuran-2-ylmethoxycarbonylamino]-3-(4-fluoro-phenyl)-propionic acid; (R)-2-[5-(3,5-difluoro-phenyl)-benzofuran-2-ylmethoxycarbonylamino]-3-(4-fluoro-phenyl)-propionic acid; (R)-3-phenyl-2-(2-phenyl-quinolin-6-ylmethoxycarbonylamino)-propionic acid; (R)-2-[5-(1H-indol-5-yl)-benzofuran-2-ylmethoxycarbonylamino]-3-phenyl-propionic acid; (R)-2-[2-(1H-indol-4-yl)-benzoxazol-5-ylmethoxycarbonylamino]-3-phenyl-propionic acid; (R)-2-[2-(3,5-difluoro-phenyl)-benzoxazol-5-ylmethoxycarbonylamino]-3-phenyl-propionic acid; 2-(5-phenyl-benzofuran-2-ylmethoxycarbonylamino)-3-pyridin-4-yl-propionic acid; and 2-(5-phenyl-benzofuran-2-ylmethoxycarbonylamino)-3-pyridin-3-yl-propionic acid, or individual isomers, racemic or non-racemic mixtures of isomers, or pharmaceutically acceptable salts or solvates thereof.

GENERAL SYNTHETIC REACTION SCHEMES

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and Organic Reactions, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about –78° C. to about 150° C., more preferably from about 0° C. to about 125° C.

In general, the compounds of Formula I can be prepared by the process of the following Reaction Schemes.

Scheme 1

Scheme 1 describes a method of preparing a compound of Formula I, wherein A is —O(CH$_2$)—, m is 1, n and r are 0, B is —CH$_2$—, and R$^1$, R$^2$, and R$^3$ are aryl, preferably phenyl, X is halo, Alk is alkyl, and R is a phenyl ring substituent as defined in the Summary of the Invention.

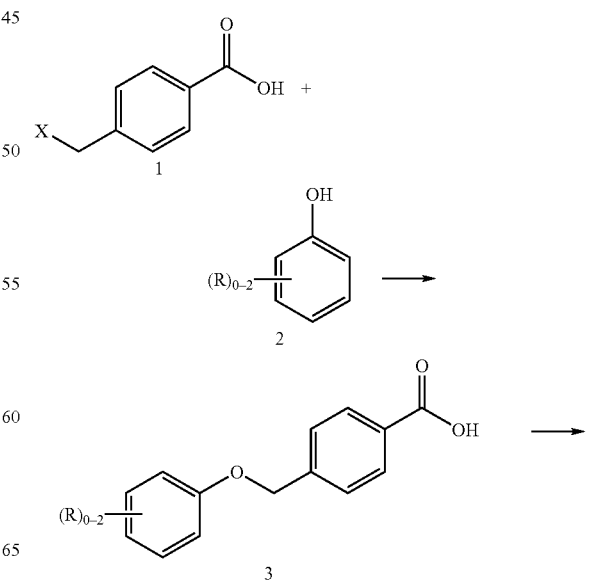

-continued

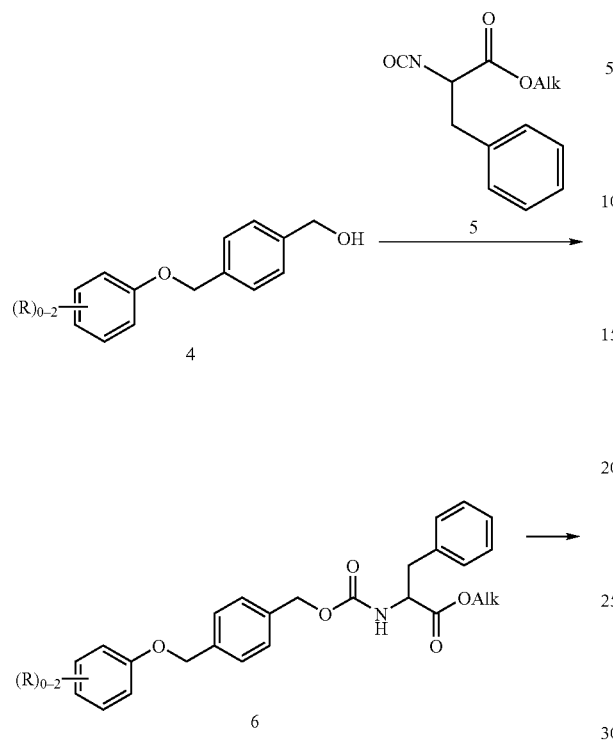

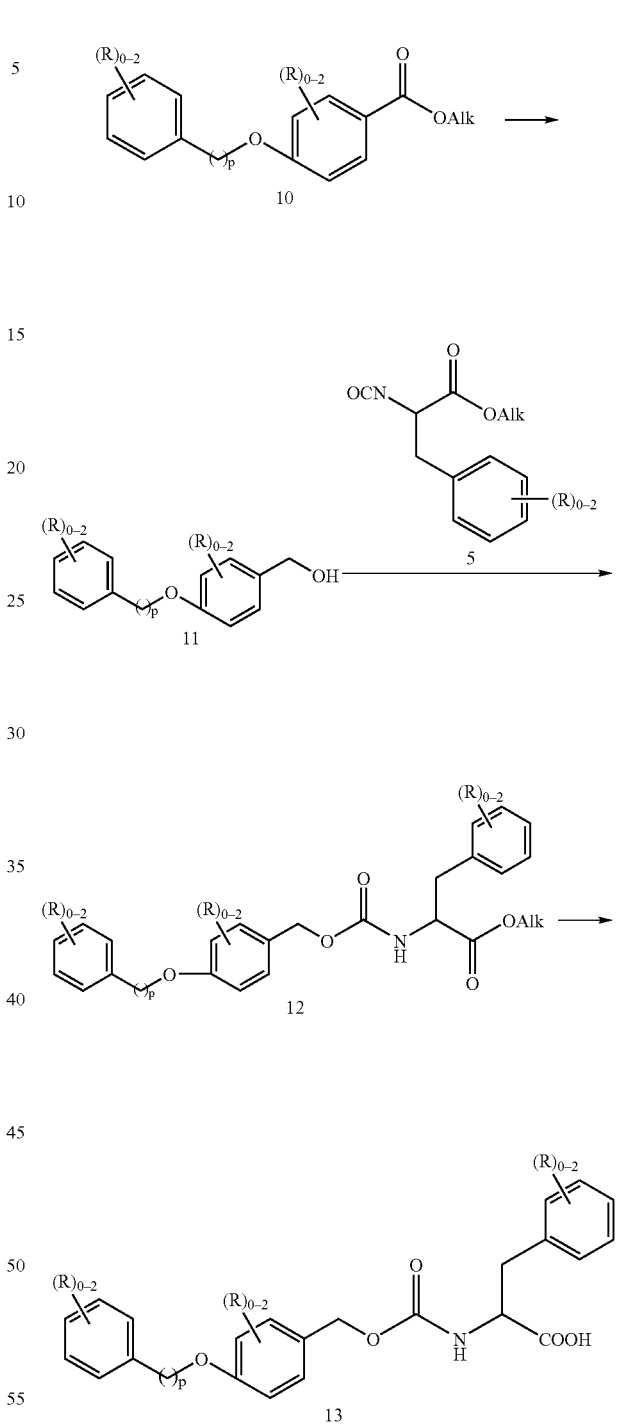

Scheme 2

Scheme 2 describes a method of preparing a compound of Formula I, wherein A is —(CH$_2$)$_p$O—, m is 1, n and r are 0, B is —CH$_2$—, R$^1$, R$^2$ and R$^3$ are aryl, preferably phenyl, Alk is alkyl, and R is a phenyl ring substituent as defined in the Summary of the Invention.

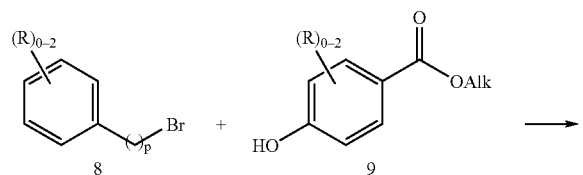

Scheme 3

Scheme 3 describes a method of preparing a compound of Formula I, wherein A is a single bond, m is 1, n and r are 0, B is —CH$_2$—, R$^1$ and R$^3$ are aryl, preferably phenyl, R$^2$ is heteroaryl, Alk is alkyl, and R is a phenyl ring substituent as defined in the Summary of the Invention.

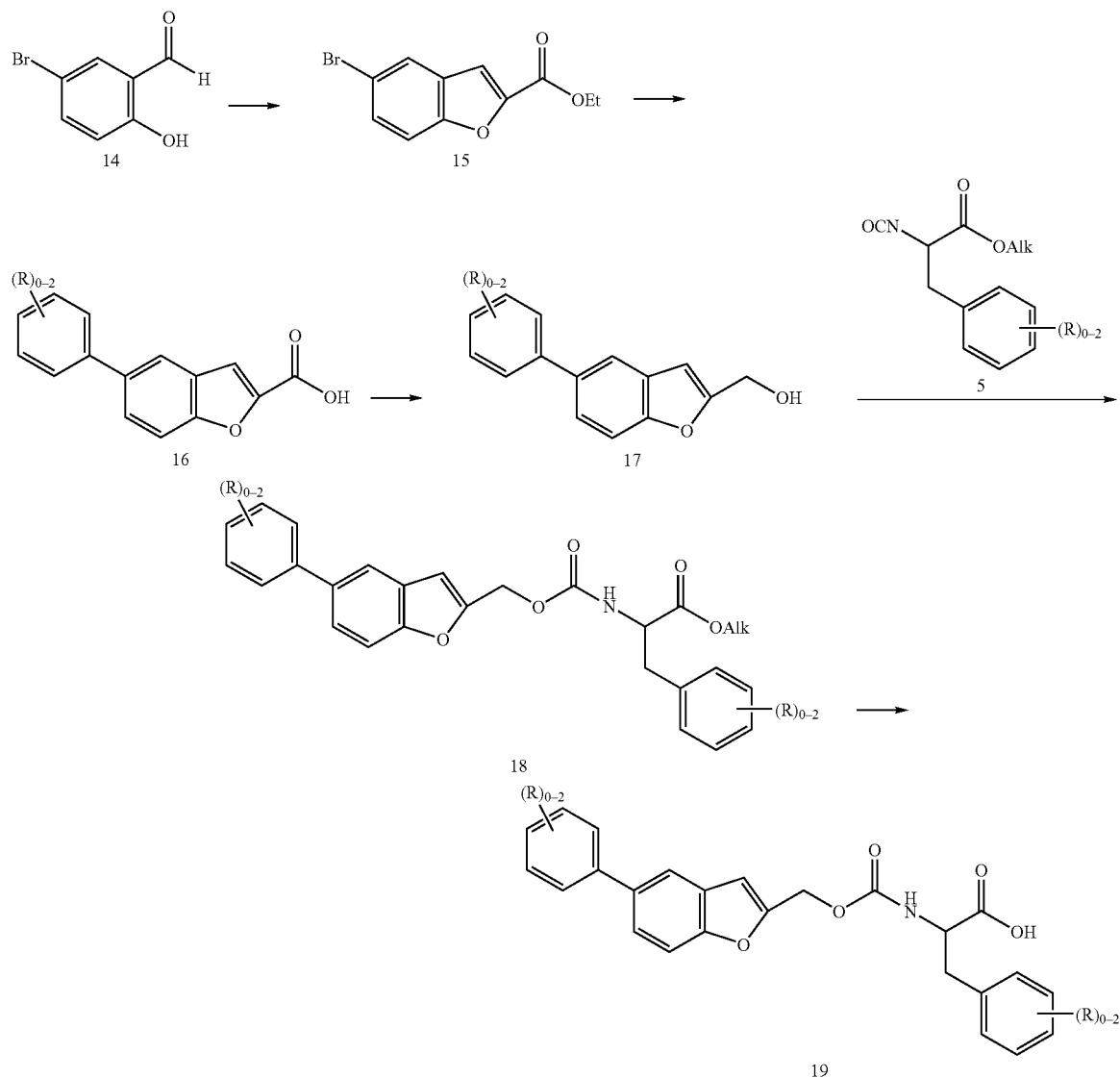
Alternatively, compound 17 can be synthesized as shown in the following scheme:
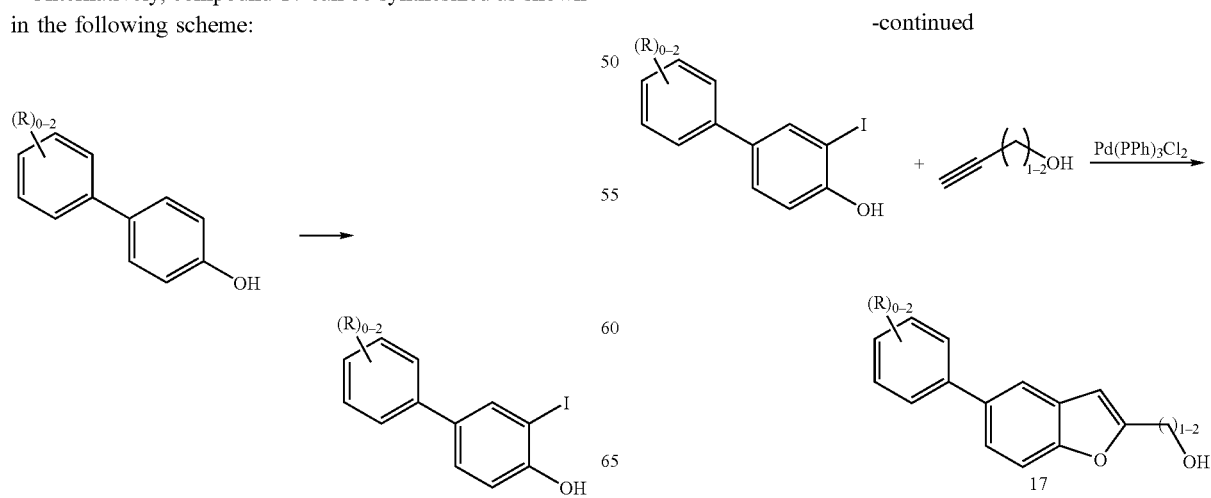

Scheme 4

Scheme 4 describes a method of preparing a compound of Formula I, wherein A is a single bond, m is 1, n and r are 0, B is —CH$_2$—, R$^1$ and R$^2$ are heteroaryl, R$^3$ is aryl, preferably phenyl, Alk is alkyl, and R is a phenyl ring substituent as defined in the Summary of the Invention.

amount of a suitable base, for example potassium hydroxide, potassium carbonate, sodium carbonate, preferably potassium hydroxide in a suitable solvent preferably dimethyl sulfoxide (DMSO), and further reduction with, for example, lithium aluminum hydride or borohydride in a suitable inert ether solvent such as tetrahydrofuran (THF), diethylether or dimethoxyethane.

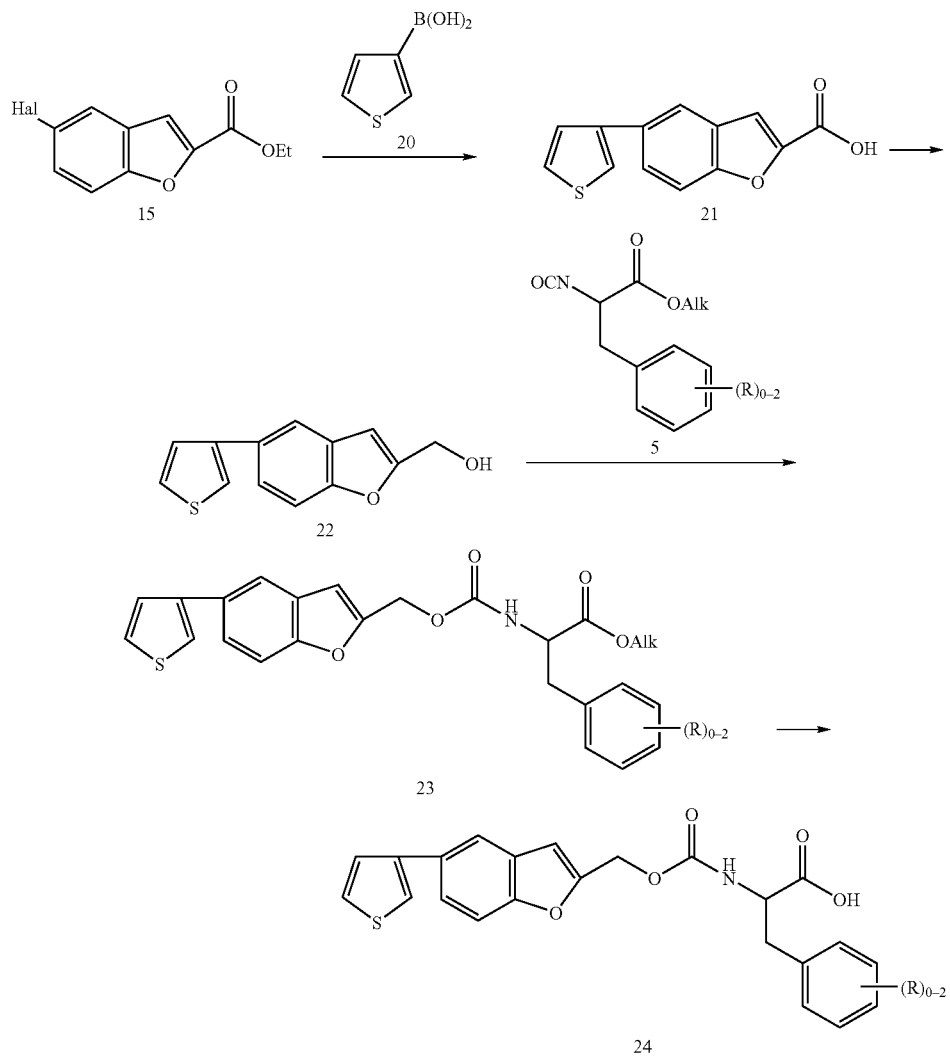

Generally as set forth in reaction Schemes 1, 2, 3, and 4, the preparation of alcohols of formulae 4, 11, 17, and 22 can be effected with 2-isocyanato-3-phenyl-propionate 5 (prepared according to the method described by Nowick et al, *J. Org. Chem.* 1996, 61, 3929) in the presence of a base for example triethylamine or 4-dimethylaminopyridine (DMAP). Hydrolysis of the respective resulting esters of formulae 6, 12, 18, and 23 can be effected with an alkali hydroxide such as sodium, lithium or potassium in a lower alkanol solution to prepare acids of formulae 7, 13, 19 and 24 respectively.

Compounds of formulae 4 and 11 of Schemes 1 and 2 can be prepared by alkylation of phenols of formulae 2 and 9 with haloalkylbenzoic acid, preferably chloroalkylbenzoic acid or bromoalkylbenzoic acid, in the presence of an excess Compounds of formulae 17 and 22 of Schemes 3 and 4 can be prepared from a halobenzofuran carboxylate, preferably bromobenzofuran carboxylate 15 with benzeneboronic acid and thiopheneboronic acid respectively in the presence of a catalyst preferably tetrakis-triphenylphosphine-palladium and a base such as sodium carbonate or potassium carbonate, and further reduction of the acids with, for example, lithium aluminum hydride or borohydride in a suitable solvent such as THF, diethyl ether or 1,2-dimethoxyethane. Aryl halides coupling to boronic acids have been described in the chemical literature, for example *Synth. Commun.*, 1981, 11 513, and *Chem. Rev.*, 1995, 95, 257.

Alternatively, compound 17 can be prepared from a certain 4-biphenol, that after iodination into the 3-iodo substituent following the procedure described in *J. Org. Chem.,* 1990, 55, 5287, and followed by a condensation with the terminal acetylene of an acetylenic alcohol such as prop-2-yn-1-ol or but-3-yn-1-ol in the presence of bis-(triphenylphosphine)palladium (II)chloride, copper iodide and a base such as tetramethylguanidine in a suitable solvent such as DMF following the procedure in *Tetrahedron Letters,* 1997, 38, 2311.

Exemplary preparations of Schemes 1, 2, 3 and 4 are given in Examples 1, 2, 3, and 4 respectively. Alternate preparations of compound 17 can be found in Example 3.

Scheme 5

Scheme 5 describes a method of preparing a compound of Formula I, wherein A is a single bond or —(CH$_2$)$_p$—, m is 1, n and r are 0, B is —CH$_2$—, R$^1$ and R$^3$ are aryl, preferably phenyl, R$^2$ is a heteroaryl, such as benzofuranyl, Alk is alkyl, and R is a phenyl ring substituent as defined in the Summary of the Invention.

the procedure described in C. W. Holzapfel et al. *Tetrahedron* 1995, 51, 8555. An ester of formula 27 can be prepared according to the procedure of D. Francelli et al., *Tetrahedron Letters,* 1997, 38, 237 by condensation of the iodohydrobenzoate of formula 26 with phenylacetylene or phenylalkylacetylene in the presence of bis-(triphenylphosphine)-palladium(II)chloride in a suitable solvent. A propionic acid of formula 29 can be prepared by reduction of a methyl ester of formula 27 with lithium aluminum hydride or borohydride, followed by acylation with 2-isocyanato-3-phenylpropionate 5, and hydrolysis according to the procedures in the aforementioned schemes.

Exemplary preparations of Scheme 5 are given in Example 5.

Scheme 6

Scheme 6 describes a method of preparing a compound of Formula I, wherein A is a single bond, m is 1 to 3, n and r are 0, B is —CH$_2$—, R$^1$, R$^2$ and R$^3$ are aryl, preferably phenyl,

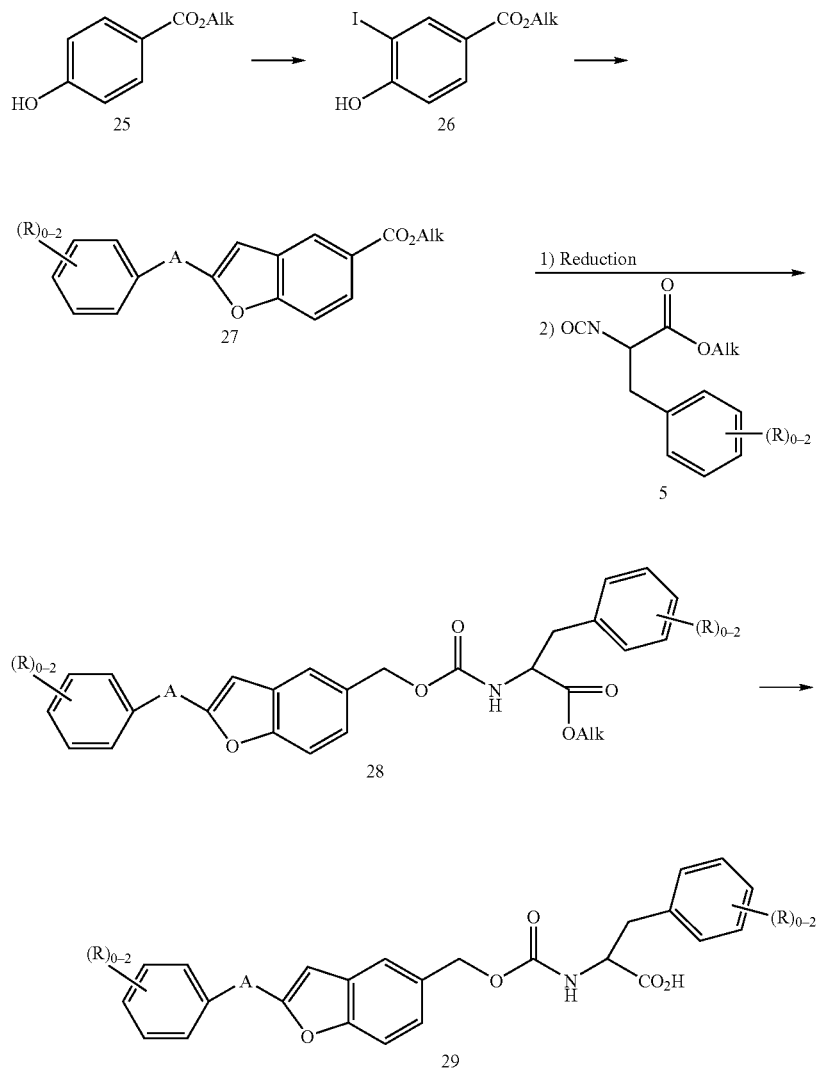

Generally as set forth in reaction Scheme 5, 3-iodo-4-hydrobenzoate of formula 26 can be prepared according to Alk is alkyl, and R is a phenyl ring substituent as defined in the Summary of the Invention.

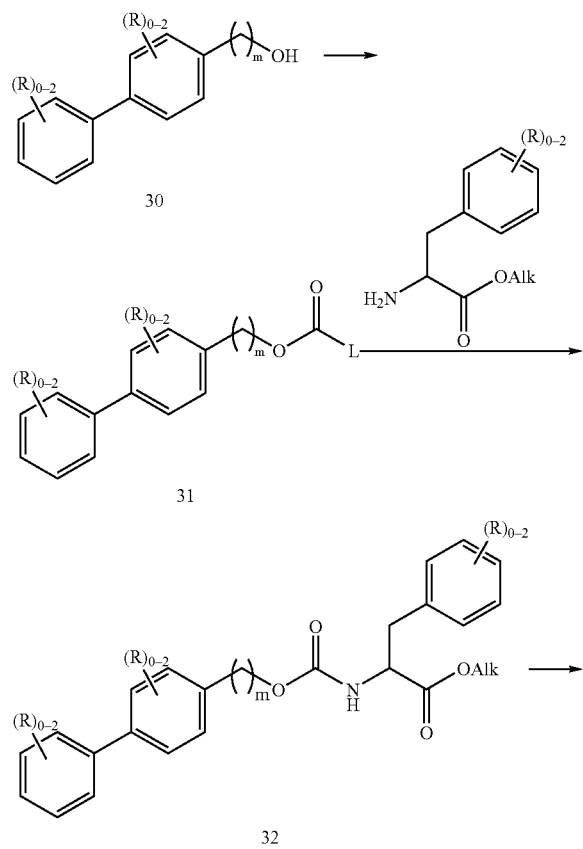

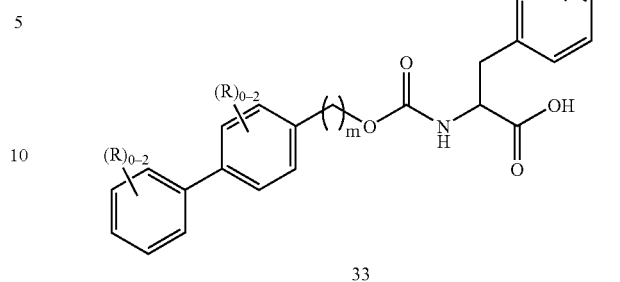

-continued

Generally as set for in reaction Scheme 6, biphenyl-4-methyl formate of formula 31 wherein L is a leaving group, for example chloro, can be prepared when biphenylmethanol 30 is treated with phosgene in an inert chlorinated solvent such as chloroform or methylene chloride. Acylation of the choloroformate can be effected with phenylalanine ester in the presence of a base such as sodium or potassium bicarbonate in a suitable solvent, for example methylene chloride, and then hydrolyzed to prepare an acid of formula 33. Hydrolysis can be effected following the aforementioned procedures.

Exemplary preparation of Scheme 6 are given in Example 6.

Scheme 7

Scheme 7 describes a method of preparing a compound of Formula I, wherein A is a single bond, m is 1, n and r are 0, B is —CH$_2$—, $R^1$ and $R^2$ are aryl, R' is hydrogen or alkyl, $R^3$ is a heteroaryl, Alk is alkyl, and R is a phenyl ring substituent as defined in the Summary of the Invention.

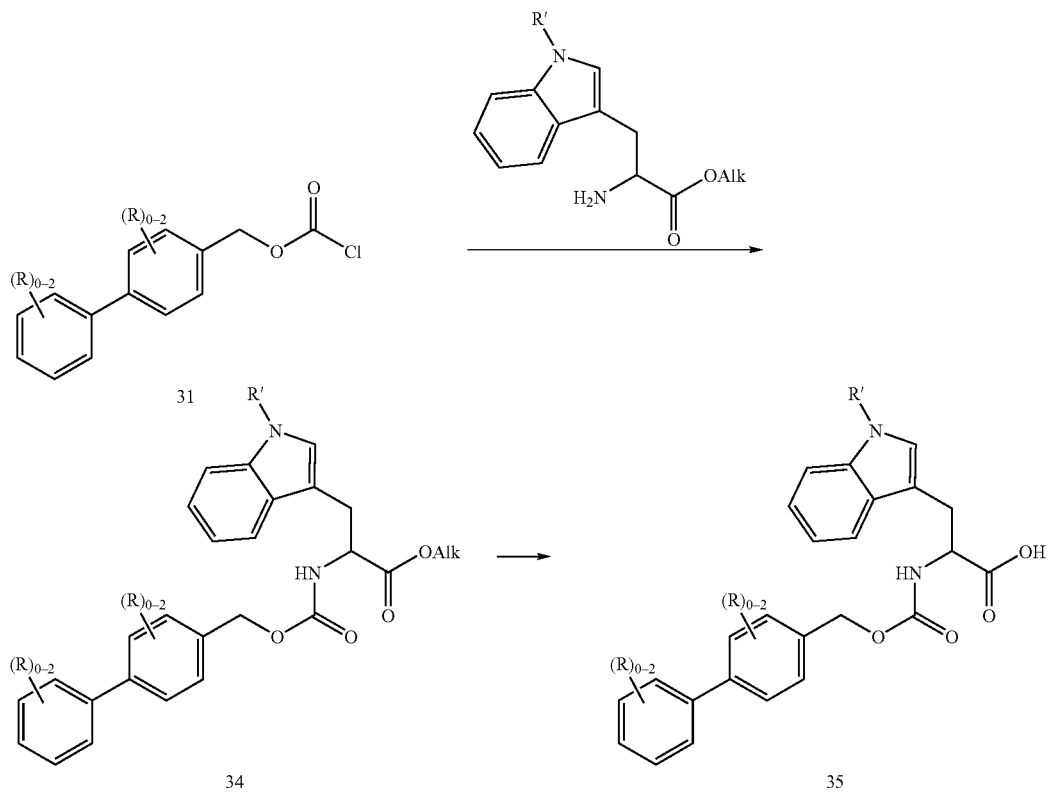

Generally the reaction Scheme 7 follows the same procedures as Scheme 6, but the acylation is effected substituting phenylalanine ester hydrochloride with optionally substituted tryptophan ester hydrochloride in a suitable solvent such as methylene chloride.

Exemplary preparations of Scheme 7 are given in Example 6.

Scheme 8

Scheme 8 describes an alternative method of preparing a compound of Formula I, wherein A is —O(CH$_2$)—, m is 1, n and r are 0, B is —CH$_2$—, R$^1$ is aryl or heteroaryl, R$^2$ and R$^3$ are phenyl, Alk is alkyl, and R is a phenyl ring substituent as defined in the Summary of the Invention.

Generally as set forth in Scheme 8, a methyl ester of formula 37 can be prepared by reaction of a chloromethylbenzyl alcohol of formula 36 with the isocyanate of formula 5 following the procedures of the precedent schemes. Esters of formula 38 (R$^1$=phenyl) and 39 (R$^1$=indolyl) can be prepared by alkylation with p-fluorophenol or indolol respectively in the presence of a base such as sodium, potassium or cesium carbonate, preferably cesium carbonate in a suitable solvent such as DMSO or methylene chloride. Hydrolysis following the precedent procedures can be carried out in preparing the respective acids of formulas 40 (R$^1$=phenyl) and 41 (R$^1$=indolyl).

Exemplary preparations of Scheme 8 are given in Example 7.

Scheme 9

Scheme 9 describes a method of preparing a compound of Formula I, wherein A is a single bond, m is 1, n and r are 0, B is —CH$_2$—, R$^1$ and R$^3$ are aryl, preferably phenyl, R$^2$ is a heteroaryl such as indolyl, Alk is alkyl, and R is a phenyl ring substituent as defined in the Summary of the Invention.

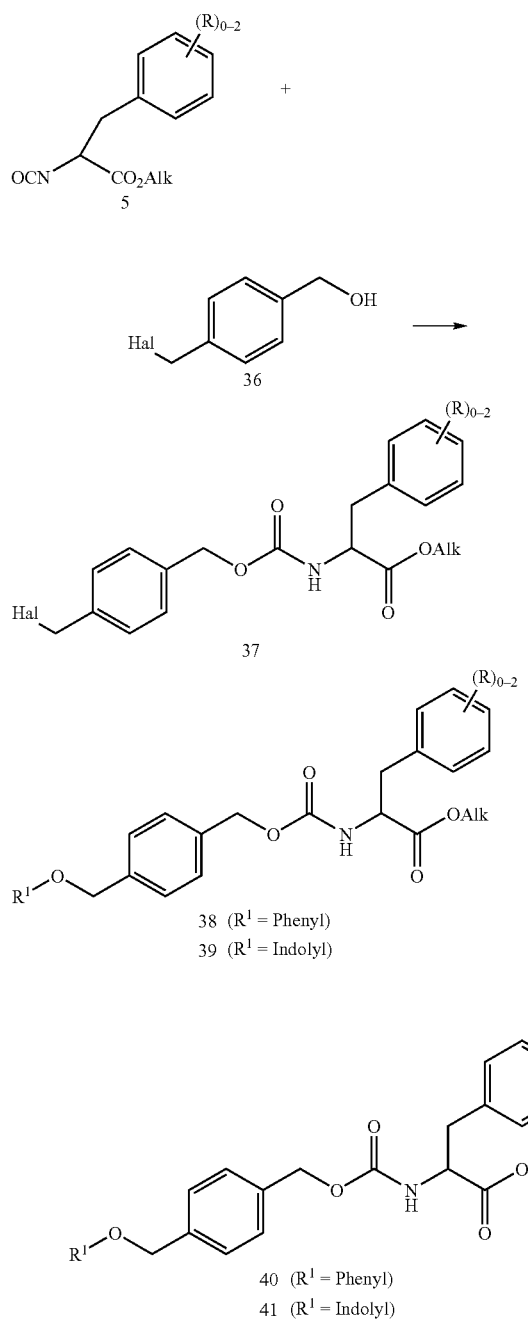

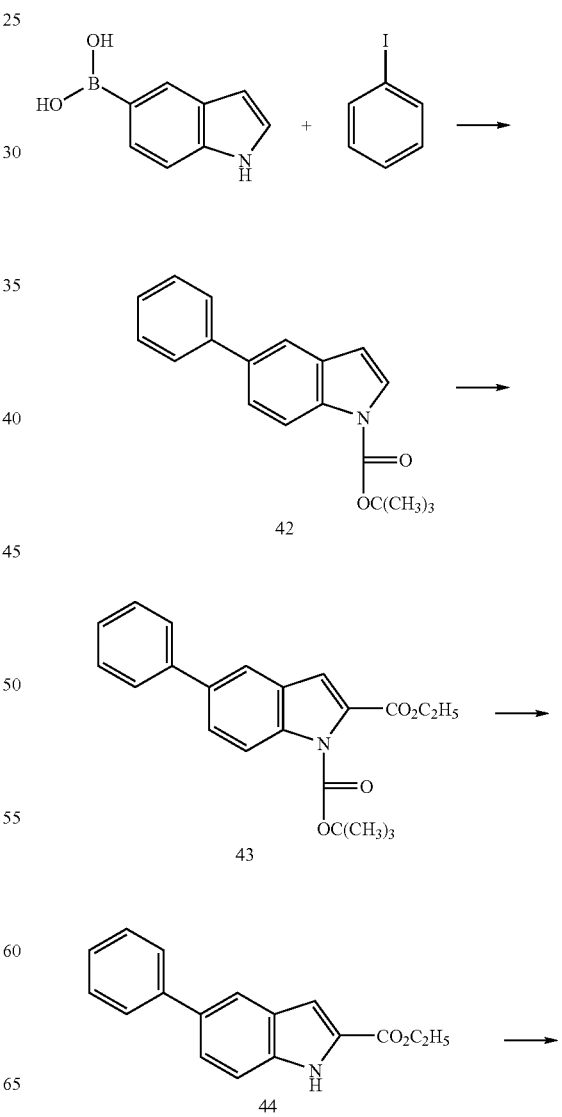

-continued

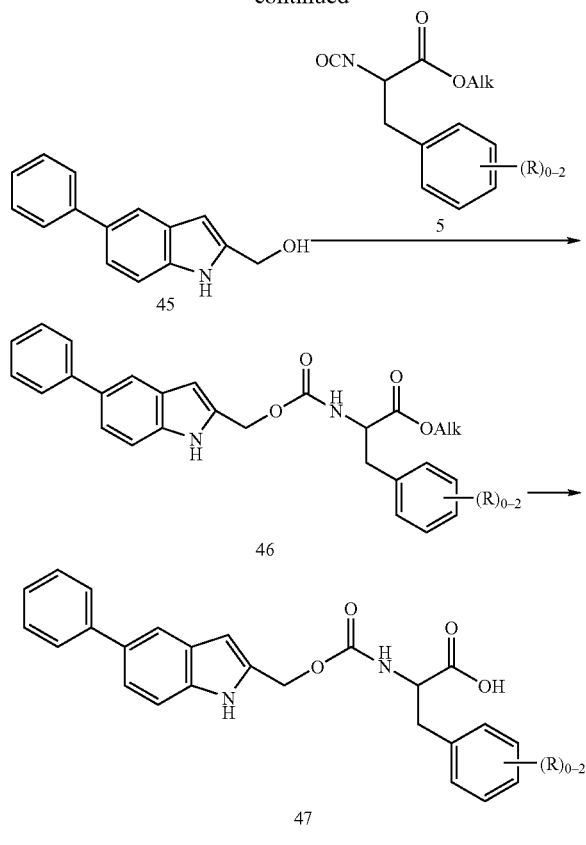

45

46

47

Generally as set forth in Scheme 9, 5-phenyl-1H-indole 42 can be prepared following the procedure described by Y. Yang et al, *Heterocycles*, 1992, 34, 1 169, from indoleboronic acid in the presence of a catalyst such as tetrakis-(triphenylphosphine)-palladium and a base such as sodium or potassium carbonate in a suitable solvent such as dioxane. The phenylindolecarboxylic acid ester 44 can be prepared after protection of the amino group with a suitable protecting group as described herein, preferably t-butoxycarbonyl, deprotonation with a strong base such as t-butyllithium, carboxylation and removal of the nitrogen protective group. Removal of the nitrogen protective group can be effected by means as described herein. A detailed description of the techniques applicable to protective groups and their removal can be found in T. W. Greene, *Protective Groups in Organic Synthesis*, Wiley and Sons, New York, 1991. For example a method of deprotection when the protective group is N-t-butoxycarbonyl can be carried out with trifluoroacetic acid or hydrochloric acid in a suitable solvent or a mixture of suitable inert organic solvents. 2-(5-Phenyl-indol-2-yl-methoxycarbonylamino)-3-phenyl- propionic acid 47 can be prepared after reduction, acylation and hydrolysis of the compound of formula 44 following the procedures of the precedent schemes.

Exemplary preparations of Scheme 9 are given in Example 8.

Scheme 10

Scheme 10 describes a method of preparing a compound of Formula I, wherein A is a single bond, m is 1, n and r are 0, B is —CH$_2$—, R$^1$ and R$^3$ are aryl, preferably phenyl, and R$^2$ is a heteroaryl, such as benzoxazol-2-yl, as defined in the Summary of the Invention.

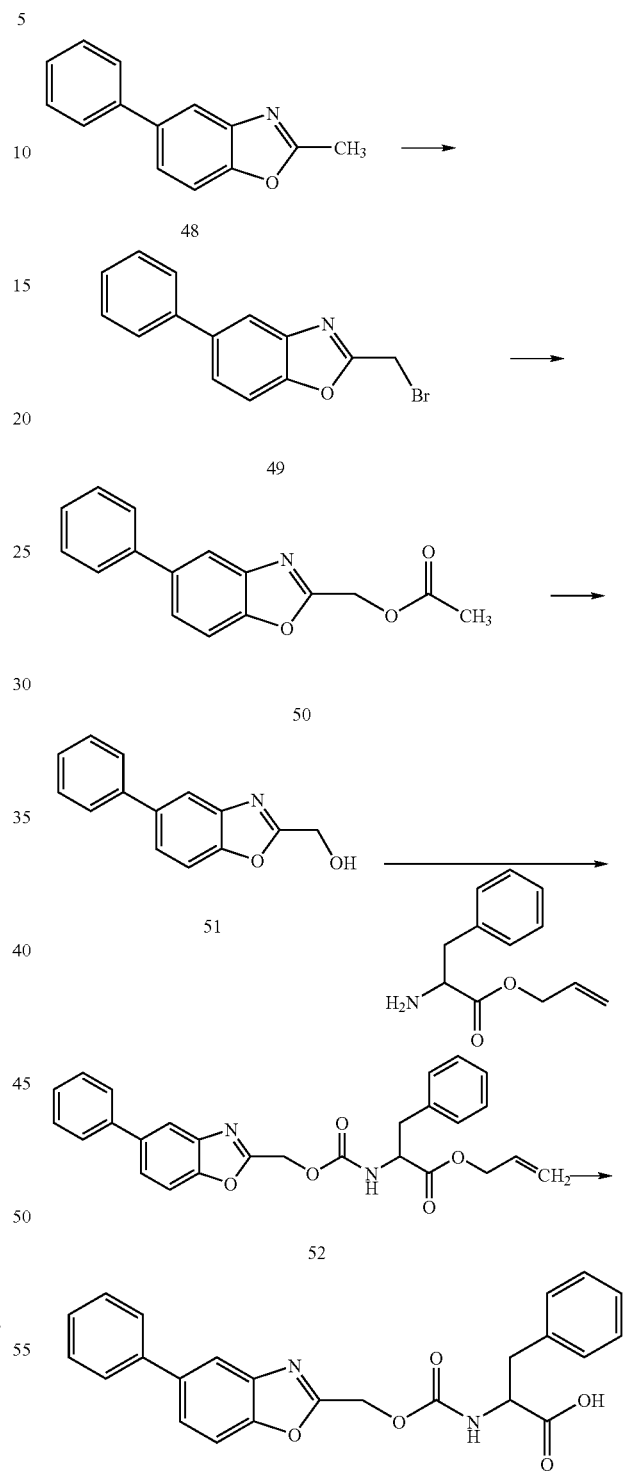

48

49

50

51

52

53

Generally as set forth in Scheme 10, 2-methyl-5-phenylbenzoxazole 48 can undergo a radical bromination in the presence of for example azodiisobutyronitrile (AIBN) or benzoyl peroxide, preferably AIBN, and N-bromosuccinimide in a suitable solvent such as carbon tetrachloride to yield a corresponding bromomethyl derivative of formula 49. Replacement of the bromide with an acetate can be effected with an acetate such as cesium acetate in an inert solvent such as dimethylformamide. Removal of the acetate in a compound of formula 50 can be effected with a base such as sodium or potassium carbonate preferably potassium carbonate in a suitable solvent such as methanol to yield an alcohol of formula 51. An allyl ester of formula 52 can be prepared by reaction with carbonyidiimidazole in a suitable solvent such as methylene chloride, and further addition of the tosic salt of phenylalanine allyl ester (prepared according to the procedure of Waldman and Kunz, *Liebigs Ann. Chem.*, 1983, 1712) in the presence of a base such as triethylamine in a suitable solvent such as methylene chloride. An acid of formula 53 can be prepared by deprotection in ethanol in the presence of a suitable catalyst such as tris(triphenylphosphine)-rhodium chloride at approximately 80° C.

Exemplary preparations of Scheme 10 are given in Example 9.

Scheme 11

Scheme 11 describes a method of preparing a compound of Formula I, wherein A is a single bond, m is 1, n and r are 0, B is —$CH_2$—, $R^1$ and $R^3$ are aryl, preferably phenyl, $R^2$ is a heteroaryl, such as benzoxazol-5-yl, Alk is alkyl, and R is a phenyl ring substituent as defined in the Summary of the Invention.

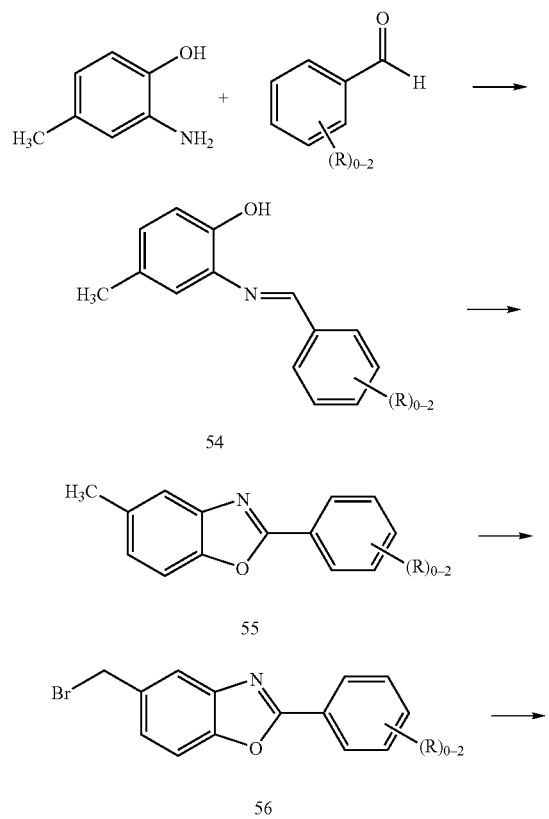

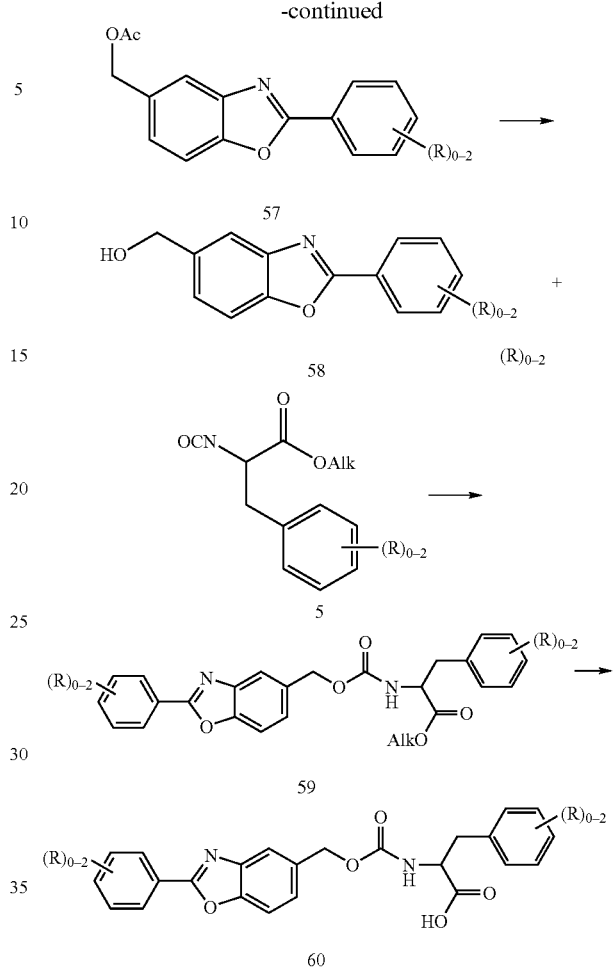

Generally as set forth in Scheme 11, 2-benzylideneamino-4-methylphenol 54 can be prepared following the procedure described by A. W. Baker, *J. Am. Chem. Soc.*, 1959, 81, 1524, from 2-amino-p-cresol and benzaldehyde in a suitable solvent such as methanol. 5-Methyl-2-phenylbenzoxazole 55 can be prepared following the procedure described by R. Varma et al., *J. Heterocyclic Chem.*, 1998, 35, 1539 by cyclization of 2-benzylideneamino-4-methylphenol 54 with manganese (III) acetate dihydrate in a suitable inert solvent such as benzene or toluene, preferably toluene. Radical bromination of the methyl group can be effected by means described in Scheme 10 in the presence of azodiisobutyronitrile (AIBN) or benzoyl peroxide, preferably AIBN, and N-bromosuccinimide in a suitable solvent such as carbon tetrachloride to yield 5-bromomethyl-2-phenylbenzoxazole 56. Replacement of the bromide derivative of formula 56 can be effected with an acetate such as potassium or cesium acetate, preferably cesium acetate in an inert solvent such as dimethylformamide, followed by hydrolysis to yield the alcohol of formula 58. Acylation of the alcohol of general formula 58 with 2-isocyanato-3-phenyl-propionate 5, followed by hydrolysis according to the procedures in the aforementioned schemes can give (R)-2-(2-phenylbenzoxazol-5-ylmethoxycarbonylamino)-3-phenyl propionic acid 60.

Exemplary preparations of Scheme 11 are given in Example 10.

Scheme 12

Scheme 12 describes a method of preparing a compound of Formula I, wherein A is a single bond, m is 1, n and r are 0, B is —CH$_2$—, R$^1$ and R$^3$ are pyridyl, and R$^2$ is (2-hydroxymethyl)benzofuran-5-yl as defined in the Summary of the Invention.

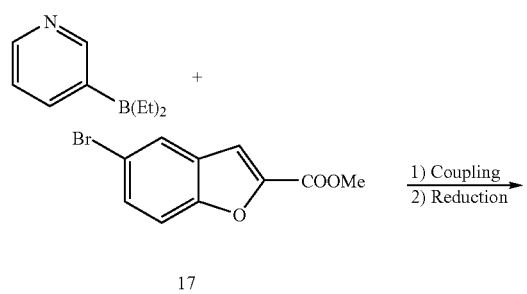

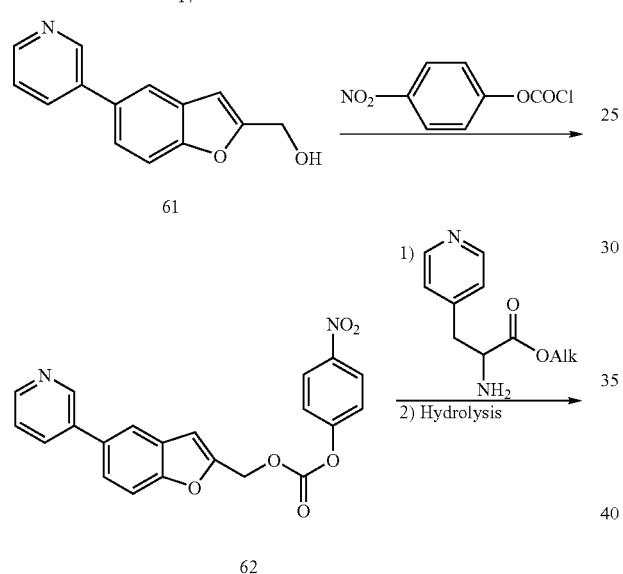

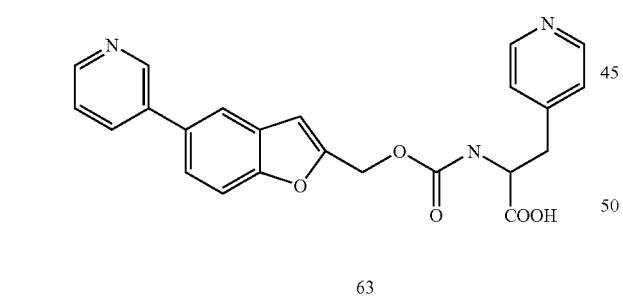

Generally as set forth in Scheme 12, (5-pyridin-3-yl-benzofuran-2-yl)-methanol 61 can be prepared following the procedure of Scheme 3 for compound 17 but replacing benzeneboronic acid with diethyl 3-pyridyl borane. Acylation with 4-nitrophenyl chloroformate in an halogenated solvent such as dichloromethane can give 5-pyridin-3-yl-benzofuran-2-ylmethyl p-nitrophenyl carbonate 62, which when treated with 2-amino-3-pyridin-4-yl-propionic acid methyl ester (method for the synthesis is described in the chemical literature, for example *J. Org. Chem.,*1958, 23, 575) and DMAP in a suitable inert solvent such as DMF, followed by hydrolysis can give 3-pyridin-4-yl-2-(5-pyridin-3-yl-benzofuran-2-ylmethoxycarbonylamino)-propionic acid 63.

Exemplary preparations of Scheme 12 are given in Example 11.

Scheme 13

Scheme 13 describes a method of preparing a compound of Formula I, wherein A is a single bond, m is 1, n and r are 0, B is —CH$_2$—, R$^1$ and R$^3$ are aryl, preferably phenyl, Alk is alkyl, and R$^2$ is 2,3-dihydro-benzofuranol-5-yl as defined in the Summary of the Invention.

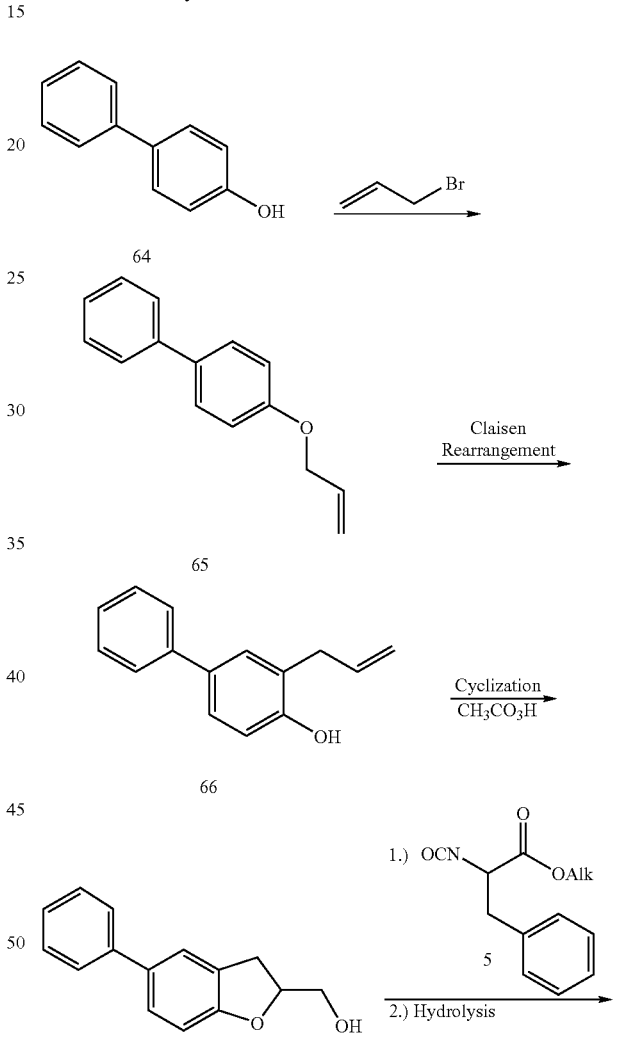

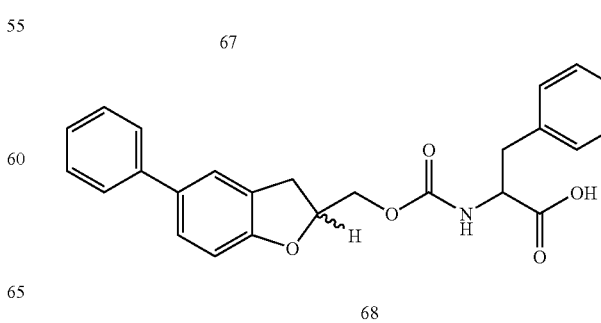

Generally as set forth in Scheme 13, allyl bromide can react with 4-phenylphenol 64 to give the allyl ether 65 that under basic conditions can undergo Claisen rearrangement to prepare an allyl alcohol 66. Treatment with peracetic acid can effect cyclization to the 2,3-dihydro-benzofuran-2-yl alcohol 67. Following the procedure of Schemes 1 to 5 treatment with 2-isocyan.ato-3-phenyl-propionate 5, and hydrolysis can give the acid of formula 68.

Exemplary preparations of Scheme 13 are given in Example 12.

Scheme 14

Scheme 14 describes a method of preparing a compound of Formula I, wherein A is a —O(CH$_2$)$_2$—, m is 1, n and r are 0, B is —CH$_2$, R$^1$, R$^2$, and R$^3$ are aryl, preferably phenyl, and Alk is alkyl as defined in the Summary of the Invention.

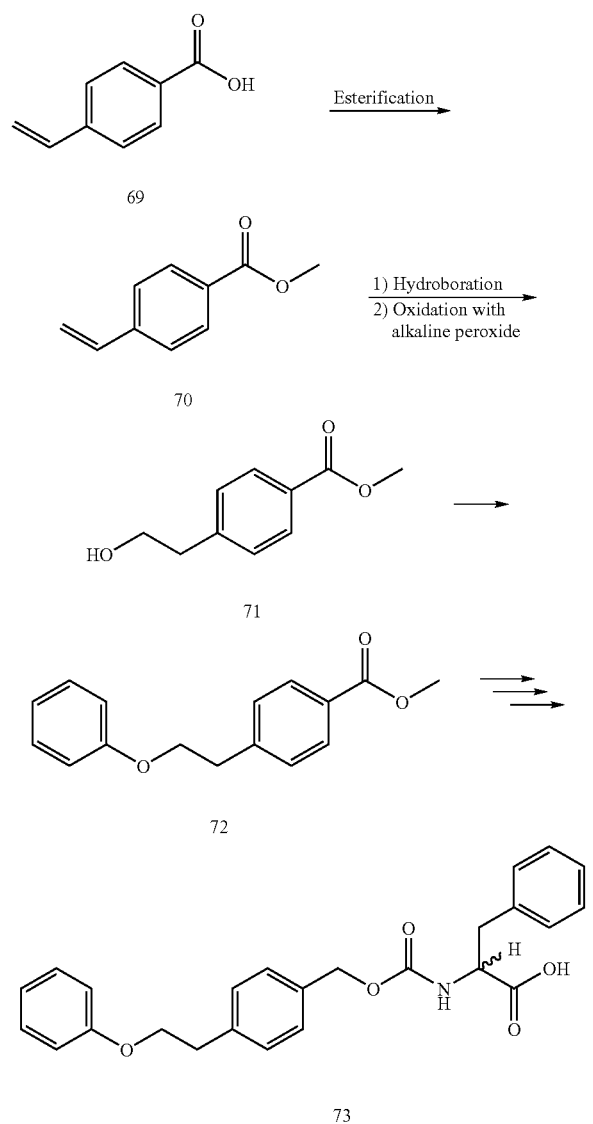

Generally as set forth in Scheme 14, 4-vinylbenzoic acid 69 can be esterified following the procedure in *Liebigs Ann. Chem.*, 1988, 559–563, in methanol with thionylchloride. The vinyl benzoate 70 can be hydroborated with 9-BBN or BH$_3$, preferably 9-BBN, followed by oxidation with an alkaline peroxide in an inert solvent, preferably tetrahydrofuran, to yield the alcohol of Formula 71. Conversion into the phenyl ether 72 can be effected with addition of phenol in the presence of diethyl azodicarboxylate and triphenyl phosphine, in an inert solvent such as tetrahydrofuran, following a procedure in Synthesis, 1981,1, or in *J. Chem. Soc. Perkin Trans.* 1981, 1, 2328. Reduction of the benzoate of formula 72, condensation with an isocyanate of Formula 5, and hydrolysis as in the previous schemes can give the compound of Formula 73.

General Utility

The IP receptor antagonists such as those described in this invention preferably possess anti-inflammatory and/or analgesic properties in vivo. Accordingly, preferred compounds are useful as anti-inflammatory and/or analgesic agents in mammals, especially humans. They find utility in pain conditions from a wide variety of causes, including but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Preferred compounds also find utility in inflammatory conditions from a variety of causes, including but not limited to bacterial, fungal or viral infections, rheumatoid arthritis, osteoarthritis, surgery, bladder infection or idiopathic bladder inflammation, over-use, old age, or nutritional deficiencies, prostatitis, and conjunctivitis.

Preferred compounds also find utility in bladder disorders associated with bladder outlet obstruction and urinary incontinence conditions such as bladder outlet obstruction, urinary incontinence, reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, pelvic pain syndrome, prostatodynia, cystitis, and idiophatic bladder hypersensitivity.

Preferred compounds also find utility in the treatment of hypotensive vascular diseases such as hypotension associated with septic shock.

In addition, preferred compounds also find utility in the treatment of respiratory diseases such as allergies and asthma.

These and other therapeutic uses are described, for example, in *Goodman & Gilman's, The Pharmacological Basis of Therapeutics*, ninth edition, McGraw-Hill, New York, 1996, Chapter 26:601–616; and Coleman, R. A., *Pharmacological Reviews*, 1994, 46, 205–229.

Testing

The binding affinity of these compounds to the intended target may be measured with the in vitro Human Platelet IP receptor binding Assay as described in more detail in Example 23. The anti-inflammatory/analgesic activity of the compounds of this invention may be assayed by in vivo assays such as the Rat Carrageenan Paw Assay, the Rat Complete Freund's Adjuvant-Induced Assay, and the Carbaprostacyclin Induced Writhing Test as described in more detail in Examples 24, 25, and 29 respectively. The inhibition of bladder contractions of this invention may be assayed by in vivo assays such as Inhibition of Bladder Contractions Induced by Isovolumetric Bladder Distension in Rats and Inhibition of Volume-Induced Contractions in Rats, as described in more detail in Examples 26 and 27 respectively. Activity in the inhibition of the septic shock may be assayed by in vivo assays such as the Rat Reversal of Endotoxin-Induced Hypotension Assay, as described in more detail in Example 28.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease. In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds,-allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

The compounds of the present invention can be formulated in transdermal or subcutaneous drug delivery devices. These delivery systems are advantageous when sustained release of the compound is necessary and when patient compliance with a treatment regimen is crucial. Compounds in a transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 16–22.

EXAMPLES

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures, etc.), but some experimental error and deviation should, of course, be allowed for as well as due to differences such as, for example, in calibration, rounding of numbers, and the like.

Example 1

(R)-2-(4-Phenoxymethyl-benzyloxycarbonylamino)-3-phenyl-propionic acid 7

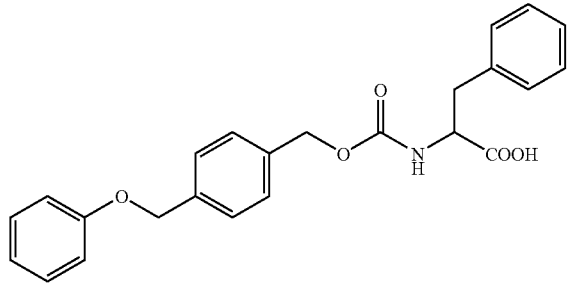

In accordance with the general Scheme 1, the following is the preparation of a compound of Formula I, wherein each of $R^1$, $R^2$, and $R^3$ is phenyl, A is —$OCH_2$—, B is —$CH_2$—, m is 1, and n and r are 0.

Step 1:

4-Phenoxymethylbenzoic acid 3.

Phenol 2 (4.706 g, 50.0 mmol) and KOH (6.172 g, 110 mmol) were combined in dimethyl sulfoxide (DMSO) (250 ml). 4-Chloromethylbenzoic acid 1 (8.530 g, 50.0 mmol) was added. The mixture was stirred at room temperature overnight. The mixture was then poured into $H_2O$ and acidified with concentrated HCl. The solution was then extracted and concentrated to give a solid. The solid was dissolved in an aqueous sodium bicarbonate solution, then washed with ethyl acetate. The aqueous mixture was then acidified with dilute HCl forming a precipitate which was filtered and dried to give about 3.7 g of 4-phenoxymethyl-benzoic acid 3.

Step 2:

4-Phenoxymethylphenylmethanol 4.

4-Phenoxymethylbenzoic acid 3 (3.424 g, 15.0 mmol) was dissolved in tetrahydrofuran (THF) (50 ml) and cooled to 0° C. A solution of borane in THF (33 ml, 33.0 mmol) was added dropwise at 0° C. The solution was then allowed to warm to room temperature and stir overnight. The mixture was then quenched with water, aqueous NaOH was added, and stirred for 30 min. The solution was then acidified with dilute HCl and extracted. The extracts were dried, concentrated, and purified by chromatography to give about 2.9 g of crystalline 4-phenoxymethylphenylmethanol 4.

Step 3:

(R)-2-(4-Phenoxymethyl-benzyloxycarbonylamino)-3-phenyl-propionic acid methyl ester 6.

(R)-Phenylalanine methyl ester hydrochloride (6.5 g, 30 mmol) was dissolved in methylene chloride and cooled to 0° C. Phosgene (2M in toluene, 21.0 ml, 42.0 mmol) was added followed by pyridine (9.0 ml, 111 mmol). The mixture was allowed to warm to room temperature and was stirred for three hours. The mixture was then poured into dilute HCl. The layers were separated. The organic extracts were washed, dried, and concentrated to give about 5.8 g of a clear oil of (R)-2-isocyanato-3-phenyl-propionic acid methyl ester 5.

4-Phenoxymethylphenylmethanol 4 (0.857 g, 4.0 mmol), (R)-2-isocyanato-3-phenyl-propionic acid methyl ester 5 (1.026 g, 5.0 mmol) and 4-dimethylaminopyridine (DMAP) (10 mg) were combined, heated until molten, and stirred for 20 min. Upon cooling, the residue was purified by chromatography to give about 1.6 g of (R)-2-(4-phenoxymethyl-benzyloxycarbonylamino)-3-phenyl-propionic acid methyl ester 6.

Step 4:

(R)-2-(4-Phenoxymethyl-benzyloxycarbonylamino)-3-phenyl-propionic acid 7.

(R)-2-(4-Phenoxymethyl-benzyloxycarbonylamino)-3-phenyl-propionic acid methyl ester 6 (1.605 g, 3.83 mmol) was dissolved in methanol (40ml) at room temperature. A solution of LiOH (177 mgs, 4.21 mmol) in 15ml of $H_2O$ was then added and the mixture was stirred overnight. The mixture was diluted with $H_2O$ (50 ml). The methanol was then removed in vacuo. The aqueous residue was acidified with 4.5N HCl forming a precipitate that was filtered and dried. Recrystallization gave about 1.2 g of (R)-2-(4-phenoxymethyl-benzyloxycarbonylamino)-3-phenyl-propionic acid 7, mp. 115.9–116.70C.

Similarly replacing phenol 2 with the appropriate substituted phenols in Step 1 gave the following compounds:

2-[4-(2-methoxy-phenoxymethyl)-benzyloxycarbonylamino]-3-phenyl propionic acid, 74 mp. 92.6–93.5° C., 2-[4-(2-fluoro-phenoxymethyl)-benzyloxycarbonylamino]-3-phenyl-propionic acid, 75 mp. 114.0–117.0° C.;

2-[4-(3-fluoro-phenoxymethyl)-benzyloxycarbonylamino]-3-phenyl-propionic acid, 76 mp. 107.9–110.0° C.;

(R)-2-[4-(3-methanesulfonylamino-phenoxymethyl)-benzyloxycarbonylamino]-3-phenyl-propionic acid, 77 mp. 161.9–164.9° C.;

(R)-2-[4-(3-benzenesulfonylamino-phenoxymethyl)-benzyloxycarbonylamino]-3-phenyl-propionic acid, 78 mp. 96.6–98.6° C.;

(R)-2-[4-(3-acetylamino-phenoxymethyl)-benzyloxycarbonylamino]-3-phenyl-propionic acid, 79 mp. 190.3–193.5° C.;

(R)-2-[4-(3-nitro-phenoxymethyl)-benzyloxycarbonylamino]-3-phenyl-propionic acid, 80 mp. 160.8–161.7° C.; and (R)-3-phenyl-2-(4-{3-[(1-phenyl-methanoyl)-amino]-phenoxymethyl }-benzyloxycarbonylamino)-propionic acid, 81 mp. 161.9–163.7° C.

Similarly replacing phenol 2 in Step 1 with thiophenol gave 3-phenyl-2-(4-phenylsulfanylmethyl-benzyloxycarbonylamino)-propionic acid, 183 mp. 113.3–114.1° C.

Similarly replacing 4-chloromethylbenzoic acid 1 in Step 1 with 3-fluoro-4-bromomethylbenzoic acid (prepared from 3-fluoro-4-methyl-benzoic acid by bromination with AIBN and N-bromosuccinimide in carbon tetrachloride, as described in the procedure in *J. Med. Chem.*, 1992, 35, 877–885, gave 2-(3-fluoro-4-phenoxymethyl-benzyloxycarbonylamino)-3-phenyl-propionic acid, 82 mp. 104.2–104.7° C.

Similarly replacing (R)-2-isocyanato-3-phenyl-propionic acid methyl ester 5 in

Step 3 with appropriate isocyanato propionic acid derivatives, the following compounds can be prepared:

(R)-2-isocyanato-3-(3-benzenesulfonylamino-phenyl)-propionic acid methyl ester gave 3-(3-benzenesulfonylamino-phenyl)-2-(4-phenoxymethyl-benzyloxycarbonylamino)-propionic acid, 83 mp. 129.7–130.3° C.; and (R)-2-isocyanato-3-(1-methyl-1H-indol-3-yl)-propionic acid methyl ester gave (R)-3-(1-methyl-1H-indol-3-yl)-2-(4-phenoxymethyl-benzyloxycarbonylamino)-propionic acid, 170 mp. 79.9–82.6° C.

Example 2

(R)-2-(4-Phenethyloxybenzyloxy-carbonylamino)-3-phenyl-propionic acid 13

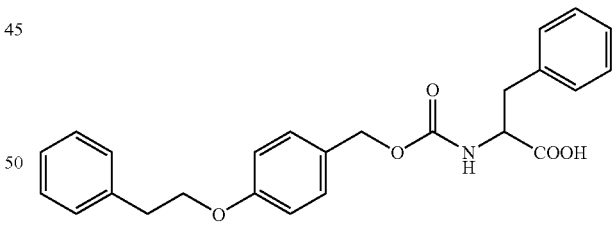

In accordance with the general Scheme 2, the following is the preparation of a compound of Formula I, wherein each of $R^1$, $R^2$, and $R^3$ is phenyl, A is —$(CH_2)_2O$—, B is —$CH_2$—, m is 1, and n and r are 0.

Step 1:

4-Phenethyloxybenzoic acid methyl ester 10.

NaH (60%) (4.400 g, 120.0 mmol) was added to freshly distilled THF chilled to 0° C., followed by 4-hydroxybenzoic acid methyl ester 9 (15.215g, 100.0 mmol). After $H_2$ evolution ceased, dimethylformamide (DMF) (20ml) was added clearing the cloudy solution. followed by phenethyl bromide 8 (16.39ml, 120.0 mmol), and the mixture was stirred at 80° C. for 24 hours. Upon cooling, the mixture was poured into H₂O and extracted. The organic extracts were combined, washed, dried, and evaporated. The residue was purified by chromatography to give about 7.6 g of 4-phenethyloxybenzoic acid methyl ester 10.

Step 2:

(4-Phenethyloxyphenyl)methanol 11.

4-Phenethyloxybenzoic acid methyl ester 10 (7.66 g, 29.89 mmol) was dissolved in diethyl ether and chilled to 0° C. LiAlH₄ was slowly added and allowed to stir at 0° C. for 3 hours. The mixture was quenched with H₂O. After addition of 3N NaOH the mixture was allowed to stir for 30 min. The mixture was then acidified with 4.5N HCl, extracted, dried, and concentrated in vacuo to give about 6.7g of a crystalline (4-phenethyloxyphenyl)methanol 11.

Step3:

(R)-2-(4-Phenethyloxybenzyloxycarbonylamino)-3-phenyl-propionic acid methyl ester 12.

(4-Phenethyloxyphenyl)methanol 11(1.141 g, 5.0 mmol), (R)-2-isocyanato-3-phenyl-propionic acid methyl ester 5 (1.036 g, 5.0 mmol) and DMAP (10 mg) were combined and heated until molten and stirred for 20 min. Upon cooling the residue was purified by chromatography to give about 2.1 g of (R)-2-(4-phenethyloxybenzyloxycarbonylamino)-3-phenyl-propionic acid methyl ester 12.

Step 4:

(R)-2-(4-Phenethyloxybenzyloxcarbonylamino)-3-phenyl-propionic acid 13.

(R)-2-(4-Phenethyloxybenzyloxy-carbon ylamino)-3-phenyl -propionic acid methyl ester 12 (2.106 g, 4.85 mmol) was dissolved in methanol (75ml) at room temperature. A solution of LiOH (244 mgs, 5.83 mmol) in 20 ml of H₂O was then added and the mixture was stirred overnight. The mixture was diluted with H₂O (100 ml). The methanol was then removed in vacuo. The aqueous residue was washed with diethyl ether and acidified with 4.5N HCl. The aqueous mixture was then extracted with dichloromethane, dried, and concentrated in vacuo. The residue was dissolved in hot diethyl ether. A slight excess of t-butylamine was added. The mixture was again heated to boiling then allowed to stand forming crystals. Upon cooling the crystals were filtered and dried to give about 1.9 g of the t-butylamine salt of (R)-2-(4-phenethyloxybenzyloxy-carbonylamino)-3-phenyl-propionic acid 13 mp.

Similarly following Steps 3 and 4, and replacing 4-(phenethyloxy-phenyl)methanol 11 with other appropriate arylalkoxyphenylmethanol, gave the following compounds:

2-(4-benzyloxybenzylcarbonylamino)-3-phenyl-propionic acid 84, mp. 118.3–119.9° C.;

2-[4-(4-fluoro-benzyloxy)-benzyloxycarbonylamino]-3-phenyl-propionic acid, 85 mp. 134.0–138.0° C.;

2-(4-phenethyloxy-benzyloxycarbonylamino)-3-phenyl-propionic acid 86, mp. 96.9–97.4° C.; and (R)-3-phenyl-2-[4-(3-phenyl-propoxy)-benzyloxycarbonylamino]-propionic acid 87, mp. 105.6–106.5° C.

Similarly following steps 3 and 4, and replacing (4-phenethyloxyphenyl)methanol with N-(4-hydroxymethyl-phenyl)-benzamide (prepared by adding benzoyl chloride to 4-aminobenzyl alcohol in pyridine and stirring for 4 hrs at room temperature), gave 2-(4-benzoylamino-benzyloxycarbonylamino)-3-phenyl-propionic acid 181, mp. 196.9–198.1° C.

Similarly replacing phenethyl bromide 8 in Step 1 with the appropriate bromides gave the following compounds:

6-bromomethyl-1H-indole gave 2-{2-hydroxy-2-[4-(1H-indol-4-ylmethoxy)-phenyl]-ethanoylamino}-3-phenyl-propionic acid 88, mp. 178–181° C.; and (2-bromoethoxy)-benzene gave (R)-2-[4-(2-phenoxy-ethoxy)-benzyloxycarbonylamino]-3-phenyl-propionic acid 89, mp. 130.0–131.3° C.;

Similarly replacing phenethyl bromide 8 in Step 1 with benzylbromide, and replacing 4-hydroxybenzoic acid methyl ester 9 in Step 1 with 4-hydroxymethylbenzoic acid methyl ester gave 2-(4-benzyloxymethyl-benzyloxycarbonylamino)-3-phenyl-propionic acid 90, mp. 78.3–79.9° C.

Example 3

(R)-2-(5-Phenyl-benzofuran-2-ylmethoxycarbonylamino)-3-phenyl-propionic acid 19

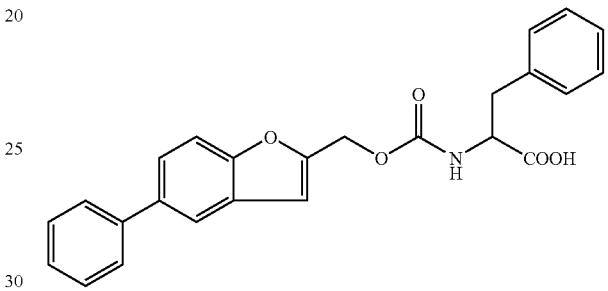

In accordance with the general Scheme 3, the following is the preparation of a compound of Formula I, wherein each of R¹ is phenyl, R² is benzofuranyl, and R³is phenyl, A is a single bond, B is —CH₂—, m is 1, and n and r are 0.

Step 1:

Ethyl 5-bromo-benzofuran-2-carboxylate 15.

A mixture of 5-bromosalicylaldehyde 14 (10 g, 50 mmole), diethyl bromomalonate (13.1 g, 55 mmole), potassium carbonate (6.9 g, 50 mmole), and 2-butanone (80 ml) was stirred at 90° C. for 16 hrs. The solvent was removed under reduced pressure at 45° C., and the residue was acidified with 1M HCl, extracted, washed, dried, and evaporated. The residue was purified by chromatography to give about 3.6 g of ethyl 5-bromo-benzofuran-2-carboxylate 15, mp. 59–60° C.

Step 2:

5-Phenyl-benzofuran-2-carboxylic acid 16.

A mixture of ethyl 5-bromo-benzofuran-2-carboxylate 15 (2.5 g, 9.3 mmole), benzeneboronic acid (1.25 g, 10.2 mmole), tetrakis(triphenylphosphine)palladium (0) (118 mg), sodium carbonate (3.25 g, 30.6 mmole) in water (25 ml), and dioxane (25 ml) was stirred under an argon atmosphere and heated to 100° C. for 16 hrs. The white heterogeneous mass was acidified with 1M HCl, extracted, washed, dried, and evaporated, to give about 2.2 g of 5-phenyl-benzofuran-2-carboxylic acid 16, mp. 218–220° C.

Step 3:

2-Hydroxymethyl-5-phenyl-benzofuran 17.

A solution of 5-phenyl-benzofuran-2-carboxylic acid 16 (2.1 g, 8.8 mmole) dissolved in THF (50 ml) was cooled to 5° C. in an ice bath, and LiAlH₄ (0.67 g, 17.6 mmole) was added portionwise and stirred at room temperature for 1.5 hrs. The excess reagent was decomposed with an addition of 1M HCl, and the acidified mixture was extracted with ethyl acetate, washed, dried, and evaporated. The residue was purified by chromatography to give about 1.22 g of 2-hydroxymethyl-5-phenyl-benzofuran 17, mp. 134–135° C.

Step 4:

(R)-2-(5-Phenyl-benzofuran-2-ylmethoxycarbonylamino)-3-phenylpropionic acid methyl ester 18.

A mixture of 2-hydroxymethyl-5-phenyl-benzofuran 17 (1.20 g, 5.85 mmole), (R)-2-isocyanato-3-phenyl-propionic acid methyl ester 5 (1.2 g, 5.9 mmole), triethylamine (1.7 ml), and THF (30 ml) was heated to 50° C. under a nitrogen atmosphere for 6 hrs. The solvent was removed under reduced pressure and the residue was purified by chromatography giving about 1.6 g of (R)-2-(phenyl-benzofuran-2-ylmethoxycarbonylamino)-3-phenyl-propionic acid methyl ester 18, mp. 85–86° C.

Step 5:

(R)-2-(5-Phenyl-benzofuran-2-ylmethoxycarbonylamino)-3-phenyl-propionic acid 19.

A solution of (R)-2-(5-phenyl-benzofuran-2-ylmethoxycarbonylamino)-3-phenyl-propionic acid methyl ester 18 (1.39 g, 3.24 mmole) in methanol (30 ml) was treated with a solution of lithium hydroxide monohydrate (149 mg, 3.56 mmole) in water (2 ml) and heated to 50° C. for 3 hrs. It was then cooled to room temperature, acidified with 1M HCl, extracted with ethyl acetate, separated, washed, dried, and evaporated. The residue was crystallized to give about 1.13 g of (R)-2-(5-phenyl-benzofuran-2-ylmethoxycarbonylamino)-3-phenyl-propionic acid 19, mp. 154–156° C.

Similarly substituting benzeneboronic acid in Step 2 with the appropriate substituted benzeneboronic acids gave the following compounds:

(R)-2-[5-(4-fluoro-phenyl)-benzofuran-2-ylmethoxycarbonylamino]-3-phenyl-propionic acid 91, mp. (for 0.5 H$_2$O) 129.5–131.5° C.;

(R)-2-[5-(4-methoxy-phenyl)-benzofuran-2-ylmethoxycarbonylamino]-3-phenyl-propionic acid 92 mp. (for 1 H$_2$O) 132–156.1° C.;

(R)-2-[5-(3-fluoro-phenyl)-benzofuran-2-ylmethoxycarbonylamino]-3-phenyl-prbpionic acid 93, mp. (for 0.5 H$_2$O) 110.4–119° C.;

(R)-2-[5-(4-chloro-phenyl)-benzofuran-2-ylmethoxycarbonylamino]-3-phenyl-propionic acid 94, mp. (for 0.2 H$_2$O) 129.5–144° C.;

(R)-2-[5-(4-methyl-phenyl)-benzofuran-2-ylmethoxycarbonylamino]-3-phenyl-propionic acid 95, mp. (for 0.2 H$_2$O) 151–154° C.;

(R)-2-[5-(3-cyano-phenyl)-benzofuran-2-ylmethoxycarbonylamino]-3-phenyl-propionic acid 96, mp. (for 0.2 H$_2$O) 64–68.5° C.;

(R)-2-(5-benzo[1,3]dioxol-5-yl-benzofuran-2-yl-methoxycarbonylamino)-3-phenyl-propionic acid 97, mp. (for 0.66 H$_2$O) 125–131° C.;

(R)-2-[5-(2-fluoro-phenyl)-benzofuran-2-ylmethoxycarbonylamino]-3-phenyl-propionic acid 98, mp. (0.5 H$_2$O) 97.1–100.8° C.;

(R)-2-[5-(3,5-difluoro-phenyl)-benzofuran-2-ylmethoxycarbonylamino]-3-phenyl-propionic acid 99, mp. 163–167° C.;

(R)-2-[5-(2,3-difluoro-phenyl)-benzofuran-2-ylmethoxycarbonylamino]-3-phenyl-propionic acid 100, mp. 159–160° C.;

(R)-2-(5-benzo[1,3]dioxol-4-yl-benzofuran-2-yl-methoxycarbonylamino)-3-phenyl-propionic acid 102, mp. 191–192° C.;

(R)-2-[5-(2,5-difluoro-phenyl)-benzofuran-2-ylmethoxycarbonylamino]-3-phenyl-propionic acid 103, mp. 89.4–92.6° C.; and (R)-2-[5-(3,4-Difluoro-phenyl)-benzofuran-2-ylmethoxycarbonylamino]-3-phenyl-propionic acid 104, mp. 98.9–101.7° C.

Similarly substituting (R)-2-isocyanato-3-phenyl-proplionic acid methyl ester 5 in Step 4 with the appropriate isocyanato derivatives gave the following compounds:

(R)-3-(4-fluoro-phenyl)-2-(5-phenylbenzofuran-2-yl-methoxycarbonylamino)-propionic acid. 105, mp. (for 0.3 H$_2$O) 131.5–135° C.;

(R)-3-(4-chloro-phenyl)-2-(5-phenyl-benzofuran-2-yl-methoxycarbonylamino)-propionic acid 106, mp. 151–157° C.;

(R)-3-(4-bromo-phenyl)-2-(5-phenyl-benzofuran-2-yl-methoxycarbonylamino)-propionic acid 107, mp. 136–140° C.;

3-(3-Benzenesulfonylamino-phenyl)-2-(5-phenyl-benzofuran-2-ylmethoxycarbonylamino)-propionic acid 171, mp. 105–108° C.;

(R)-3-(3-fluoro-phenyl)-2-(5-phenyl-benzofuran-2-yl-methoxycarbonylamino)-propionic acid 108, mp. 141.4–142.3° C.;

3-phenyl-3-(5-phenyl-benzofuran-2-ylmethoxycarbonylamino)-propionic acid, 109, mp. 168.0–169.8° C.; and 4-phenyl-3-(5-phenyl-benzofuran-2-ylmethoxycarbonylamino)-butyric acid 110, mp. 168.0–169.8° C. (The isocyanato derivative used in this preparation can be prepared from the amino ester synthesized according to the procedure in *J. Med. Chem.* 1994, 37 (20), 3247 starting from benzyl 3-keto-4-phenylbutyrate).

Similarly substituting benzeneboronic acid in Step 2 with other substituted benzeneboronic acids, and substituting (R)-2-isocyanato-3-phenyl-propionic acid methyl ester 5 in Step 4 with the appropriate isocyanato derivatives gave the following compounds:

(R)-3-(4-fluoro-phenyl)-2-[5-(4-fluorophenyl)-benzofuran-2-ylmethoxycarbonylamino]-propionic acid 111, mp. (for 1 H$_2$O) 158–162° C.;

(R)-2-[5-(3-cyano-phenyl)-benzofuran-2-ylmethoxycarbonylamino]-3-(4-fluoro-phenyl)-propionic acid 112, mp. (0.2 H$_2$O) 84–87.5° C.;

(S)-3-(4-fluoro-phenyl)-2-[5-(4-fluoro-phenyl)-benzofuran-2-ylmethoxycarbonylamino]-propionic acid 113, mp. 148.3–157.0° C.;

(R)-3-(4-fluoro-phenyl)-2-[5-(2-fluoro-phenyl)-benzofuran-2-ylmethoxycarbonylamino]-propionic acid 114, mp. 105.2–110.2° C.;

(R)-2-[5-(2-chloro-phenyl)-benzofuran-2-ylmethoxycarbonylamino]-3-(4-fluoro-phenyl)-propionic acid 115, mp. 86.7–100.1° C.;

(R)-2-(5-benzo[1,3]dioxol-5-yl-benzofuran-2-yl-methoxycarbonylamino)-3-(4-fluoro-phenyl)-propionic acid 116, mp. 132–134.5° C.;

(R)-2-[5-(4-tert-butyl-phenyl)-benzofuran-2-ylmethoxycarbonylamino]-3-(4-fluoro-phenyl)-propionic acid 117, mp. 114.3–124.6° C.;

(R)-3-(4-chloro-phenyl)-2-[5-(4-fluoro-phenyl)-benzofuran-2-ylmethoxycarbonylamino]-propionic acid 118, mp. 130–154.5° C.;

(R)-3-(4-bromo-phenyl)-2-[5-(4-fluoro-phenyl)-benzofuran-2-ylmethoxycarbonylamino]-propionic acid 119, mp. 150.6–160° C.;

(R)-3-(3-fluoro-phenyl)-2-[5-(4-fluoro-phenyl)-benzofuran-2-ylmethoxycarbonylamino]-propionic acid 120, mp. 81.7–82.9° C.;

(R)-2-[5-(2,5-difluoro-phenyl)-benzofuran-2-ylmethoxycarbonylamino]-3-(4-fluoro-phenyl)-propionic acid 121, mp. 98–101° C.;

(R)-2-[5-(3,4-difluoro-phenyl)-benzofuran-2-ylmethoxycarbonylamino]-3-(4-fluoro-phenyl)-propionic acid 122, mp. 97–99.1° C.;

2-[5-(3,5-dichloro-phenyl)-benzofuran-2-ylmethoxycarbonylamino]-3-(4-fluoro-phenyl)-propionic acid 177, mp. 101.1–103.2° C.; and (R)-2-[5-(3,5-difluoro-phenyl)-benzofuran-2-ylmethoxycarbonylamino]-3-(4-fluoro-phenyl)-propionic acid 123, mp. 174–175° C.

Similarly replacing 2-hydroxmethyl-5-phenyl-benzofuran 17 in Step 4 with the appropriate methanol derivatives gave the following compounds:

[5-(4-methoxy-phenyl)-furan-3-yl]-methanol gave 2-[5-(4-methoxy-phenyl)-furan-3-ylmethoxycarbonylamino]-3-phenyl-propionic acid 126, Calculated for C22H21NO6: C66.83; H 5.35; N 3.54. Found:C 66.69; H 5.33; N 3.73;

(5-p-tolyl-furan-3-yl)-methanol gave 3-phenyl-2-(5-p-tolyl-furan-3-ylmethoxycarbonylamino)-propionic acid 127, mp. 67.7–68.2° C.;

2-hydroxethyl-5-phenyl-benzofuran (prepared as described below) gave (S)-3-phenyl-2-[2-(5-phenyl-benzofuran-2-yl)-ethoxycarbonylamino]-propionic acid 128, mp. 170.9–171.9° C.;

2-phenyl-1H-benzoimidazol-5-ylmethanol, (as described in EP 260744) gave (R)-3-Phenyl-2-(2-phenyl-1H-benzoimidazol-5-ylmethoxycarbonylamino)-propionic acid 129, mp.165–215° C.;

1-methyl-1H-benzoimidazol-5-yl-methanol, (prepared by reduction of the corresponding acid as described in DE 2641060) gave (R)-2-(1-Methyl-2-phenyl-1H-benzoimidazol-5-ylmethoxycarbonylamino)-3-phenyl-propionic acid 130, mp. 176–177° C.;

(2-phenyl-quinolin-7-yl)-methanol (prepared from the bromide as described in Bioorg. Med. Chem. Lett., 1998, 8, 1243, after conversion to the acetate with cesium acetate followed by hydrolization with sodium hydroxide), gave (R)-3-phenyl-2-(2-phenyl-quinolin-6-ylmethoxycarbonylamino)-propionic acid 131, mp. 190–191° C.;

(2-phenyl-3H-indol-6-yl)-methanol prepared by reduction of the acid as described in Tetrahedron Letters, 1997, 38, 2707 gave (R)-3-phenyl-2-(2-phenyl-1H-indol-5-ylmethoxycarbonylamino)-propionic acid 132, mp. 176–177° C.;

[4-((E)-styryl)-phenyl]-methanol gave 3-phenyl-2-[4-((E)-styryl)-benzyloxycarbonylamino]-propionic acid 133, mp. 165.0–168.5° C.;

5-benzyl-2-hydroxymethylbenzofu ran gave (R)-2-(5-benzyl-benzofuran-2-ylmethoxycarbonylamino)-3-phenyl-propionic acid 134, mp. 159.4–160.1° C.; and (R)-2-(5-benzyl-benzofuran-2-ylmethoxycarbonylamino)-3-(4-fluoro-phenyl)-propionic acid 135, mp. 177.3–133.9° C.;

3-hydroxymethyl-6-phenyl-benzofuran (prepared as described below) gave 2-(5-Phenyl-benzofuran-3-ylmethoxycarbonylamino)-3-phenyl-propionic acid 172, mp 177.6–178.6° C., and 5-benzoyl-2-hydroxymethylbenzofuran gave (R)-3-phenyl-2-[5-(1-phenyl-methanoyl)-benzofuran-2-ylmethoxycarbonylamino]-propionic acid 136, mp. 136.3–138.6° C.

Alternative synthesis of compounds of Formula 17

Preparation of 2-hydroxyethyl-5-phenyl-benzofuran

A mixture of 2.00g(6.75 mmol) of 4-hydroxy-3-iodobiphenyl, 2.36g (33.7 mmol) of 3-butyn-1-ol, 64 mg(0.34 mmol), 237 mg (0.34 mmol) of dichlorobis-(triphenylphosphine) palladium(ll), and 7.78 g (67.5 mmol) of tetramethylguanidine in 40 mL DMF was allowed to stir under an atmosphere of nitrogen at ambient temperature for 18 hrs. The reaction mixture was evaporated under high vacuum to remove the DMF. The residue was chromatographed on silica using 4% EtOAc in hexane as eluent. This afforded 1.15 g of 2-hydroxethyl-5-phenyl-benzofuran:

Similarly 3-iodo-4-hydroxy-diphenylmethane, prepared from 4-benzyl-phenol according to the procedure in J. Org. Chem. 1981, 46 (22), 4535 and propargyl alcohol gave 5-benzyl-2-hydroxymethylbenzofuran, and 4-hydroxy-3-iodobenzophenone, prepared from 4-hydroxy-benzophenone according to the procedure in J. Org. Chem. 1999, 64 (20),7312, and propargyl alcohol gave 5-benzoyl-2-hydroxymethylbenzofuran.

Preparation of 3-hydroxymethyl-6-phenyl-benzofuran

A solution of 3-phenylphenol (5.0 g, 29.4 mmol), sodium iodide (4.40 g, 29.4 mmol) and sodium hydroxide (1.17 g, 29.4 mmol) under an atmosphere of nitrogen was cooled to 0°–5°. A solution of sodium hypochlorite (42 g of a 5.25% solution, ~29.4 mmol) was added dropwise during 1¼ hrs. After addition the mixture was allowed to stir in the cold for an additional 1 hr. The reaction was quenched by the addition of 32 ml of 10% $Na_2S_2O$ solution, then acidified with 2N HCl solution.

The oil which separated was taken up in methylene chloride (~50 ml), washed with brine, and dried over $MgSO_4$. Evaporation of the solvent afforded 7.98 g of crude material which was chromatographed on silica and eluted with $CH_2Cl_2$:hexane (1:2). This afforded 1.91 g (22%) of 3-hydroxy-4-iodobiphenyl as a white solid.

A solution of 3-hydroxy-4-iodobiphenyl (1.91 g, 6.45 mmol), 3-O-bis(TBS)propynol (2.20 g, 7.75 mmol), LiCl (273 mg, 6.45 mmol), sodium carbonate (3.41 g, 32.25 mmol) and $Pd(OAc)_2$ (73 mg, 0.32 mmol) in 20 ml DMF was evacuated and flushed with argon 3 times, then heated in an oil bath at 1000 for 5½ hrs.

The reaction mixture was cooled to room temp, poured into water (50 mL) and hexanes (50 mL). The mixture was filtered to remove the insolubles. The hexane layer was separated, washed with brine, and dried over $MgSO_4$. The solvent was evaporated and the residue chromatographed on silica and eluted with 10% $CH_2Cl_2$ in hexane. This afforded 1.39 g (47%) of 2-TBS-3-(TBSoxymethyl)-6-phenylbenzofuran as a pale yellow oil.

The above bis-protected benzofuran (1.38 g, 3.0 mmol), potassium fluoride dihydrate (602 mg, 6.4 mmol) and benzyltrimethylammonium chloride (764 mg, 3.3 mmol) were combined in acetonitrile (25 ml) and heated at reflux under an atmosphere of nitrogen for 4 hrs. The reaction mixture was evaporated and the residue chromatographed on silica and eluted with EtOAc:hexane (1:2). This afforded 402 mg (58%) of 3-hydroxymethyl-6-phenylbenzofuran as a white solid.

Example 4

(R)-2-(5-Thiophen-3-yl-benzofuran-2-ylmethoxycarbonylamino)-3-phenyl-propionic acid 24.

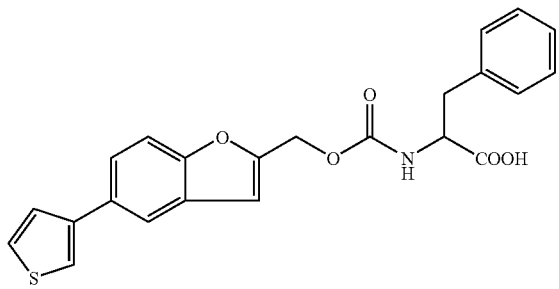

In accordance with the general Scheme 4, the following is the preparation of a compound of Formula I, wherein each of $R^1$ is thiophenyl, $R^2$ is benzofuranyl, and $R^3$ is phenyl, A is a single bond, B is —$CH_2$—, m is 1, and n and r are 0.

Step 1:

5-Thiophen-3-yl-benzofuran-2-carboxylic acid 21.

A mixture of ethyl 5-bromobenzofuran-2-carboxylate 15 (1.0 g, 3.7 mmole), 3-thiopheneboronic acid (0.52 g, 4.1 mmole), tetrakis(triphenylphosphine)palladium (0) (47 mg), sodium carbonate (1.30 g, 12.3 mmole) in water (10 ml), and dioxane (10 ml) was stirred under an atmosphere of argon and heated to 100° C. for 24 hrs. The mixture was cooled, acidified with 1M HCl, extracted with ethyl acetate, washed with water, dried, and evaporated, to give about 0.88 g of 5-thiophen-3-yl-benzofuran-2-carboxylic acid 21, mp. 215–220° C.

Step 2:

2-Hydoxymethyl-5-thiophen-3-yl-benzofuran 22.

A solution of 5-thiophen-3-yl-benzofuran-2-carboxylic acid 21 (0.84 g, 3.4 mmole) dissolved in THF (30 ml) was cooled to 5° C., LiAlH$_4$ (0.26 g, 6.9 mmole) was added portionwise. The solution was then stirred at ambient temperature for 2 hrs. After addition of 1M HCl, the mixture was extracted, washed, dried, evaporated, and the residue was purified by chromatography to give about 0.368 g of 2-hydroxymethyl-5-thiophen-3-yl-benzofuran 22, mp. 122–124° C.

Step 3:

(R)-2-(5-Thiophen-3-yl-benzofuran-2-ylmethoxycarbonylamino)-3-phenyl-propionic acid methyl ester 23.

A mixture of 2-hydroxymethyl-5-thiophen-3-yl-benzofuran 22 (0.31 g, 1.35 mmole), (R)-2-isocyanato-3-phenyl-propionic acid methyl ester 5 (0.33 g, 1.6 mmole), triethylamine (0.43 ml), and THF (25 ml) was heated to 50° C. under a nitrogen atmosphere for 14 hrs. The solvent was removed under reduced pressure and the residue was purified by chromatography giving about 0.28 g of (R)-2-(5-thiophen-3-yl-benzofuran-2-ylmethoxycarbonylamino)-3-phenylpropionic acid methyl ester 23, mp. 105–106° C.

Step 4:

(R)-2-(5-Thiophen-3-yl-benzofuran-2-ylmethoxycarbonylamino)-3-phenyl-propionic acid 24.

A solution of (R)-2-(5-thiophen-3-yl-benzofuran-2-ylmethoxycarbonylamino)-3-phenyl-propionic acid methyl ester 23 (0.23 g, 0.54 mmole) in methanol (10 ml) was treated with a solution of lithium hydroxide monohydrate (25 mg, 0.59 mmole) in water (1 ml) and heated to 50° C. for 4 hrs, cooled, acidified with 1M HCl, evaporated, partitioned between ethyl acetate and 1M HCl, separated, washed, dried, and evaporated. The residue was crystallized giving about 0.15 g of (R)-2-(5-thiophen-3-yl-benzofuran-2-ylmethoxycarbonylamino)-3-phenylpropionic acid 24, mp. 169–170° C.

Similarly substituting thiopheneboronic acid in Step 1 with appropriate heteroarylboronic acids the following compounds were prepared:

indole-4-boronic acid gave (R)-2-[5-(1H-indol-4-yl)-benzofuran-2-ylmethoxycarbonylamino]-3-phenyl-propionic acid 137, mp. 100–106° C. (as dicyclohexylamine salt);

indole-5-boronic acid gave (R)-2-[5-(1H-indol-5-yl)-benzofuran-2-ylmethoxycarbonylamino]-3-phenyl-propionic acid 138, mp. 90–95° C.;

pyridine-4-boronic acid gave 3-phenyl-2-(5-pyridin-4-yl-benzofuran-2-ylmethoxycarbonylamino)-propionic acid 174, mp. 119–121° C.;

pyrimidine-5-boronic acid (prepared following the procedure in *Chem. Scripia*, 1986, 26, 305) gave 3-phenyl-2-(5-pyrimidin-5-yl-benzofuran-2-ylmethoxycarbonylamino)-propionic acid 175, mp. 192–192.5° C.

Similarly substituting thiopheneboronic acid in Step 1 with diethyl 3-pyridinyl borane gave the following compounds:

(R)-3-phenyl-2-(5-pyridin-3-yl-benzofuran-2-ylmethoxycarbonylamino)-propionic acid 124, mp. 143–145.7° C.; and (R)-3-(4-fluoro-phenyl)-2-(5-pyridin-3-yl-benzofuran-2-ylmethoxycarbonylamino)-propionic acid 125, mp. (0.6 H$_2$O) 176.9–178.4° C.

Example 5

(R)-3-Phenyl-2-(2-phenyl-benzofuran-5-ylmethoxycarbonylamino)-propionic acid 29

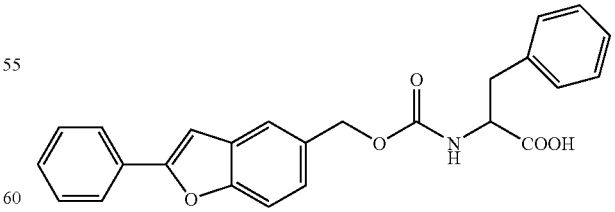

In accordance with the general Scheme 5, the following is the preparation of a compound of Formula I, wherein each of $R^1$ and $R^3$ are phenyl, $R^2$ is benzofuranyl, A is a single bond or —$(CH_2)_p$—, B is —$CH_2$—, m is 1, and n and r are 0.

Step 1:

2-Phenyl-benzofuran-5-carboxylic acid methyl ester 27.

A mixture of methyl 3-iodo-4-hydroxybenzoate 26 (1 g, 3.6 mmol), phenylacetylene (2 ml, 18 mmol), tetramethylguanidine (4.5 ml, 36 mmol), copper(I)iodide (34 mg, 1.8 mmol), bis(triphenylphosphine)palladium (II)chloride (130 mg, 1.8 mmol) and DMF (20 ml) was stirred at room temperature overnight. The reaction mixture was poured into water, extracted, washed and dried. After evaporation of the solvent, the residue was purified by chromatography to give about 0.9 g of 2-phenyl-benzofuran-5-carboxylic acid methyl ester 27.

Step 2:

(R)-3-Phenyl-2-(2-phenyl-benzofuran-5-ylmethoxycarbonylamino)-propionic acid methyl ester 28.

To a solution of 2-phenyl-benzofuran-5-carboxylic acid methyl ester 27 (0.7 g, 2.8 mmol) in THF (15 ml) was added dropwise a solution of lithium aluminum hydride (1M in THF) (3.6 ml, 3.6 mmol) at 0° C. After the addition, the reaction mixture was allowed to warm to room temperature and stirred for 2 hrs. The mixture was cooled to 0° C., diluted with ether and sodium sulfate decahydrate was added. After filtration the solids were washed with ether, and the organic layer was washed and dried. Evaporation of the solvent and purification by chromatography yielded (2-phenyl-benzofuran-5-yl)-methanol (0.55 g). A mixture of (2-phenyl-benzofuran-5-yl)-methanol (0.5 g, 2.23 mmol), (R)-2-isocyanato-3-phenyl-propionic acid methyl ester 5 (0.55 g, 2.68 mmol), triethylamine (0.74 ml, 5.35 mmol) and THF (15 ml) was heated at 50° C. for 6 hrs. Additional (R) 2-isocyanato-3-phenyl-propionic acid methyl ester 5 (0.15 g) was added, and the mixture was stirred at 50° C. overnight. The solvent was evaporated and the residue was partitioned between ethyl acetate and water. After extraction and evaporation of the solvent, the residue was purified by chromatography to give about 0.76 g of (R)-3-phenyl-2-(2-phenyl-benzofuran-5-ylmethoxycarbonylamino)-propionic acid methyl ester 28.

Step 3:

(R) 3-Phenyl-2-(2-phenyl-benzofuran-5-ylmethoxycarbonylamino)-propionic acid 29.

To a solution of (R)-3-phenyl-2-(2-phenyl-benzofuran-5-ylmethoxy-carbonylamino)-propionic acid methyl ester 28(0.7 g, 1.63 mmol) in THF (15 ml) and methanol (15 ml) was added a solution of lithium hydroxide (1N) in water (2 ml, 2 mmol). The reaction mixture was heated at 50° C. for 6 hrs then left at room temperature overnight. The solvent was evaporated and water (20 ml) was added. The mixture was acidified with 1N HCl and ethyl acetate was added. The solid obtained after precipitation and evaporation of the solvent was purified by recrystallization to give about 0.35 g of (R)-3-phenyl-2-(2-phenyl-benzofuran-5-ylmethoxycarbonylamino)-propionic acid 29, mp. 172.8–173.5° C.

Similarly substituting phenylacetylene in Step 1 with 3-phenyl-1-propyne and following the procedure of Steps 1, 2 and 3, the following compounds were prepared:

(R)-2-(2-benzyl-benzofuran-5-ylmethoxycarbonylamino)-3-phenyl-propionic acid 139 mp. 108.8–110.5° C.; and (R)-3-(4-fluoro-phenyl)-2-[2-(4-fluoro-phenyl)-benzofuran-5-ylmethoxycarbonylamino]-propionic acid 140, mp. 201.0–204.0° C.

Example 6

2-(Biphenyl-4-ylmethoxycarbonylamino)-3-phenyl-propionic acid 33

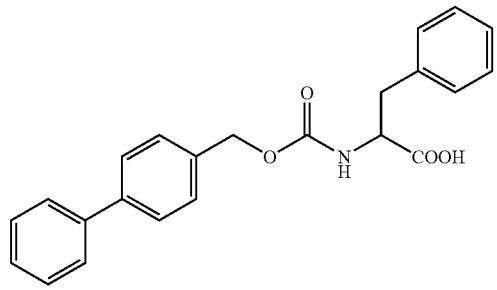

In accordance with the general Scheme 6, the following is the preparation of a compound of Formula I, wherein each of $R^1$, $R^2$ and $R^3$ are phenyl, A is a single bond, B is —$CH_2$—, m is 1, and n and r are 0.

Step 1:

Biphenyl-4-methyl chloroformate 31.

Biphenyl-4-methanol 30 (1.82 g, 10 mmol) was dissolved in 25 ml $CH_2Cl_2$, and phosgene (20% in toluene, 8 ml) was added at room temperature. The solution was allowed to stand at room temperature for 96 hrs, and the volatiles were evaporated. The crude product was purified by chromatography to yield about 1.51 g of biphenyl-4-methyl chloroformate 31.

Step 2:

2-(Biphenyl-4-ylmethoxycarbonylamino)-3-phenyl-propionic acid methyl ester 32.

Phenylalanine methyl ester hydrochloride (880 mg, 4.2 mmol) was suspended in 20 ml $CH_2Cl_2$. A solution of 2 g $K_2CO_3$ in 20 ml $H_2O$ was added. The chloroformate 31 (1.0 g, 4 mmol) was added, and the biphasic mixture was stirred for 30 minutes at room temperature It was then poured into ether, and the organic layer was evaporated and chromatographed. The product was recrystallized to yield about 1.3 g of 2-(biphenyl-4-ylmethoxycarbonylamino)-3-phenyl-propionic acid methyl ester 32.

Step 3:

2-(Biphenyl-4-ylmethoxycarbonylamino)-3-phenyl-propionic acid 33.

The ester 32 (1.30 g, 3.4 mmol) was dissolved in 25 ml methanol, then treated with 200 mg LiOH in 5 ml water. After 30 minutes at 50° C., the mixture was poured into excess water, made acidic with dilute HCl, and extracted. Recrystallization yielded about 1.12 g of 2-(biphenyl-4-ylmethoxycarbonylamino)-3-phenyl-propionic acid 33, mp. 141.7–142.2° C.

Similarly by replacing biphenyl-4-methanol in Step 1 with the appropriate substituted biphenyl-4-alcohols and/or replacing phenyl alanine ester hydrochloride in Step 2 with substituted phenyl alanine ester hydrochloride the following compounds can be prepared:

3-(3-benzenesulfonylamino-phenyl)-2-(biphenyl-4-ylmethoxycarbonylamino)-propionic acid 141, m/e 529, 345 (100%);

3-(4-fluoro-phenyl)-2-(4'-hydroxy-biphenyl-4-yl-methoxycarbonylamino)-propionic acid 142, mp. 65–74° C.; and 2-(3-biphenyl-4-yl-propoxycarbonylamino)-3-phenyl-propionic acid 143, mp. 139.1–139.9° C.

Similarly by replacing biphenyl-4-methanol with (4-phenylethynyl-phenyl)-methanol gave 3-phenyl-2-(4-phenyl-ethynyl-benzyloxycarbonylamino)-propionic acid 182, mp. 172.1–173.4° C.

Similarly substituting phenylalanine methyl ester hydrochloride in Step 2 with tryptophan methyl ester hydrochloride the following compound of Formula I, wherein each of $R^1$, and $R^2$ are phenyl and $R^3$ is 3-indolyl; A is a single bond; B is $CH_2$; m and n are 1; and r is 0, were prepared:

2-(biphenyl-4-methoxycarbonyl)amino-3-(3-indolyl)propionic acid 144, mp. 180.1–180.6° C.; (R)-2-(biphenyl-4-ylmethoxycarbonylamino)-3-(1-methyl-1H-indol-3-yl)-propionic acid 145, mp. 156.7–157.2° C.;

2-(biphenyl-4-ylmethoxycarbonylamino)-3-(1-propyl-1Hindol-3-yl)-propionic acid 146, mp. 136–138.3° C.;

2-(biphenyl-4-ylmethoxycarbonylamino)-3-(1-ethyl-1Hindol-3-yl)-propionic acid 147, mp. 136.8–138.5° C.; and 2-(biphenyl-4-ylmethoxycarbonylamino)-3-(1-isopropyl-1H-indol-3-yl)-propionic acid 148, mp. 143.1–144.8° C.

Similarly replacing phenylalanine methyl ester hydrochloride in Step 2 with appropriate 2-amino-3-heteroaryl propionic ester hydrochloride derivatives gave the following compounds:

2-amino-(2-methyl-1-oxo-1,2-dihydro-isoquinolin-4-yl)-propionic ester gave (R)-2-(biphenyl-4-ylmethoxycarbonylamino)-3-(2-methyl-1-oxo-1,2-dihydro-isoquinolin-4-yl)-propionic acid 149, mp. 215–217° C.;

2-amino-(1H-benzoimidazol-2-yl)-propionic ester gave (R)-3-(1H-benzoimidazol-2-yl)-2-(biphenyl-4-ylmethoxycarbonylamino)-propionic acid 150, mp. 243–245° C.

(R)-2-amino-3-phenylamino-propionic acid methyl ester gave 2-(biphenyl-4-ylmethoxycarbonylamino)-3-phenylamino-propionic acid 179; mp. 143–146° C.; and (R)-2-amino-3-(4-methoxyphenylamino-propionic acid methyl ester gave 2-(biphenyl-4-ylmethoxycarbonylamino)-3-(4-methoxy-phenylamino)-propionic acid, 180, mp 152.6–154.8° C.

Example 7

2-[4-(4-Fluoro-phenoxymethyl)benzyloxycarbonyl]amino-3-phenyl-propionic acid 40.

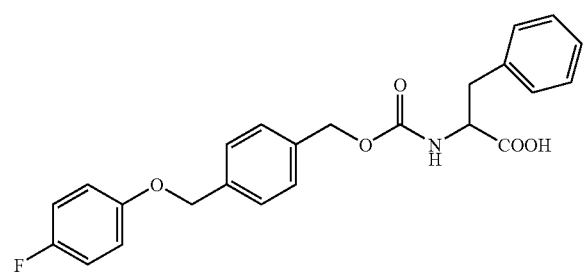

In accordance with the general Scheme 8, the following is the preparation of a compound of Formula I, wherein each of $R^1$ is phenyl or 3-indolyl, $R^2$ and $R^3$ are phenyl, A is a single bond; B is —$CH_2$—; m is 1; and n and r are 0.

Step 1:

4-Chloromethylbenzyl alcohol 36.

4-Chloromethylbenzoic acid (20 mmol) was dissolved in 20 ml THF, then 30 ml borane/THF were added. The mixture was stirred for 16 hrs at room temperature, and then quenched with excess methanol. Evaporation yielded about 2.5 g 4-chloromethylbenzyl alcohol 36.

Step 2:

2-(4-Chloromethylbenzylloxycarbonyl)amino-3-phenylpropionic acid methyl ester 37.

4-Chloromethylbenzyl alcohol 36. (790 mg, 5 mmol) and phenylalanine methyl ester isocyanate 5 (1.13 g, 5.5 mmol) were combined with 2 mg 4-dimethylaminopyridine. The mixture was melted and maintained at 110° C. for 2 minutes. Chromatography gave about 1.165 g of 2-(4-chloromethyl-benzyloxy-carbonyl)amino-3-phenyl-propionic acid methyl ester 37.

Step 3:

2-(4-(4-Fluorophenoxy)methylbenzyloxycarbonyl)amino-3-phenyl-propionic acid methyl ester 38.

p-Fluorophenol (75 mg, 0.7 mmol) was dissolved in DMSO along with 181 mg (0.5 mmol) 2-(4-chloromethyl-benzyloxycarbonyl)amino-3-phenyl-propionic acid methyl ester 37. Cesium carbonate (300 mg) was added, and the suspension was stirred at room temperature for 2 hours. The reaction mixture was partitioned between ether and dilute aqueous HCl. The organic phase was dried, evaporated and chromatographed to give about 121 mg of 2-[4-(4-fluorophenoxy methyl) benzyloxycarbonylamino]-3-phenyl-propionic acid methyl ester 38.

Step 4:

2-[4-(4-Fluoro-phenoxymethyl)benzyloxycarbonylamino]-3-phenyl-propionic acid 40.

2-[4-(4-Fluoro-phenoxymethyl)benzyloxycarbonyl] amino-3-phenyl-propionic acid methyl ester 38 (115 mg) was dissolved in 10 ml methanol, then treated with 1.1 equiv LiOH in water. After 2 hrs at 60° C., the mixture was poured into water, acidified with HCl, and extracted The organic phase was dried, evaporated and recrystallized to yield about 74 mg of 2-[4-(4-fluorophenoxymethyl) benzyloxycarbonyl]amino-3-phenyl-propionic acid 40, mp. 111.8–113.4° C.

Similarly substituting p-fluorophenol with other substituted phenols or indolols, and following the procedure of Steps 2 to 5, the following compounds were prepared:

2-[4-(1H-indol-4-yloxymethyl)-benzyloxycarbonylamino]-3-phenyl-propionic acid 41, mp. 105.9–108.5° C.;

2-[4-(1H-indol-5-ylmethoxy)-benzyloxycarbonylamino]-3-phenyl-propionic acid 151, EIMS m/e 467, 236;

(R)-3-phenyl-2-[4-(quinolin-5-yloxymethyl)-benzyloxycarbonylamino]-propionic acid 152, mp. 189.4–189.8° C.;

(R)-2-(4-indol-1-ylmethyl-benzyloxycarbonylamino)-3-phenyl-propionic acid 153, mp. 122–125° C.;

2-[4-(3-methoxy-phenoxymethyl)-benzyloxycarbonylamino]-3-phenyl-propionic acid 154, mp. (0,55 $H_2O$) 62.5–64.8° C.;

2-[4-(4-chloro-phenoxymethyl)-benzyloxycarbonylamino]-3-phenyl-propionic acid 155, mp. 122.0–123.1° C.; and 2-[4-(1H-indol-4-yloxymethyl)-benzyloxycarbonylamino]-3-phenyl-propionic acid 156, mp. 106.8–108.2° C.

Example 8

(R)-2-(5-Phenyl-indol-2-ylmethoxycarbonylamino)-3-phenyl-propionic acid 47:

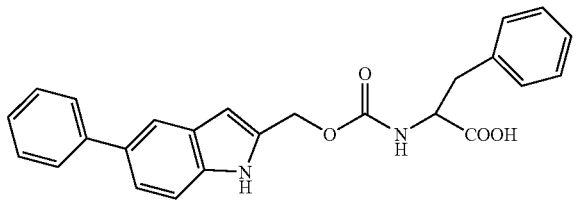

In accordance with the general Scheme 9, the following is the preparation of a compound of Formula I, wherein each of $R^1$ and $R^3$ are phenyl, $R^2$ is indolyl, A is a single bond, B is —$CH_2$—, m is 1, and n and r are 0.

Step 1:

5-Phenyl-1H-indole-1-carboxylic acid tert-butyl ester 42.

A mixture of indole-5-boronic acid (2.0 g, 12.4 mmole); iodobenzene (2.48 g, 12.2 mmole), tetrakis(triphenylphosphine) palladium (0) (288 mg, 0.25 mmole), sodium carbonate (4.34 g, 40.9 mmole) in water (20 ml), and dioxane (20 ml) was stirred under an argon atmosphere and heated to 100° C. for 5 hrs, cooled to room temperature, acidified with 1M HCl, extracted, washed, dried, and evaporated. The residue was purified by chromatography to give about 1.6 g of 5-phenyl-1H-indole, mp. 72–74° C.

A mixture of 5-phenyl-1H-indole (1.56 g, 8.1 mmole), di-tert-butyl dicarbonate (2.12 g, 9.73 mmole), and 4-dimethylaminopyridine (0.10 g, 0.81 mmole) in acetonitrile (15 ml) was stirred for 2 hrs. at room temperature under an atmosphere of nitrogen. The solution was poured into ethyl acetate, washed, dried, and evaporated. The residue was purified by chromatography to give about 1.8 g of 5-phenyl-1H-indole-1-carboxylic acid tert-butyl ester 42, mp. 105–106° C.

Step 2:

5-Phenyl-1H-indole-1-carboxylic acid tert-butyl ester-2-carboxylic acid ethyl ester 43.

A solution of 5-phenyl-1H-indole-1-carboxylic acid tert-butyl ester (1.56 g, 5.32 mmole) in dry THF (18 ml) was placed under a nitrogen atmosphere and cooled to –78° C., treated dropwise with 1.6 M tert-butyllithium in pentane (4.0 ml, 6.38 mmole), and stirred for 2.5 hrs. Ethyl chloroformate (0.69 g, 6.38 mmole) was added, and stirred for 40 minutes. The reaction mixture was then changed to an ice bath, stirred for an additional 45 minutes, and quenched with saturated $NH_4Cl$ solution. The solution was then extracted with ethyl acetate, washed, dried, and evaporated. The residue was purified by chromatography to give about 1.04 g of 5-phenyl-1H-indole-1-carboxylic acid tert-butyl ester-2-carboxylic acid ethyl ester 43.

Step 3:

5-Phenyl-1H-indole-2-carboxylic acid ethyl ester 44.

A solution of 5-phenyl-1H-indole-1-carboxylic acid tert-butyl ester-2-carboxylic acid ethyl ester 43 (1.0 g, 2.74 mmole) in dichloromethane (10 ml) was treated with trifluoroacetic acid (10 ml), and stirred at room temperature for 1 hr. Evaporation of the solvent gave about 0.72 g of 5-phenyl-1H-indole-2-carboxylic acid ethyl ester 44, mp. 173–174° C.

Step 4:

(5-Phenyl-indol-2-yl)-methanol 45.

1M Lithium aluminum hydride in THF was added to a cooled solution of 5-phenyl-1H-indole-2-carboxylic acid ethyl ester 44 (0.375 g, 1.41 mmole) in dry THF (5 ml). After 2 hrs at room temperature, the excess reagent was decomposed with water, acidified with 1M HCl, extracted, washed, dried, and evaporated to give about 0.285 g of (5-phenyl-indol-2-yl)-methanol 45, mp. 115–116° C.

Step 5

(R)-2-(5-Phenyl-indol-2-ylmethoxycarbonylamino)-3-phenyl-propionic acid methyl ester 46.

A mixture of (5-phenyl-indol-2-yl)-methanol 45 (0.259 g, 1.16 mmole), (R)-2-isocyanato-3-phenyl-propionic acid methyl ester 5 (0.286 g, 1.39 mmole), in triethylamine (0.37 ml), and THF (10 ml) was heated to 50° C. under a nitrogen atmosphere for 22 hrs. The solvent was evaporated and the residue was purified by chromatography to give about 0.220 g of (R)-2-(5-phenyl-indol-2-ylmethoxycarbonylamino)-3-phenyl-propionic acid methyl ester 46, mp. 142–143° C.

Step 6:

(R)-2-(5-Phenyl-indol-2-ylmethoxycarbonylamino)-3-phenyl-propionic acid 47.

A solution of (R)-2-(5-phenyl-indol-2-ylmethoxycarbonylamino)-3-phenyl-propionic acid methyl ester 46 (0.195 g, 0.455mmole) in methanol (20 ml) was treated with a solution of lithium hydroxide monohydrate (23 mg, 0.55 mmole) in water (1 ml) and heated to 50° C. for 7 hrs, cooled to room temperature, acidified, evaporated, extracted with EtOAc, washed, dried, and evaporated. The residue was purified by chromatography to give about 46 mg of (R)-2-(5-phenyl-indol-2-ylmethoxycarbonylamino)-3-phenyl-propionic acid 47, mp. 168–174°.

Example 9

(R)-3-phenyl-2-(5-phenyl-benzoxazol-2-ylmethoxycarbonylamino) propionic acid 53.

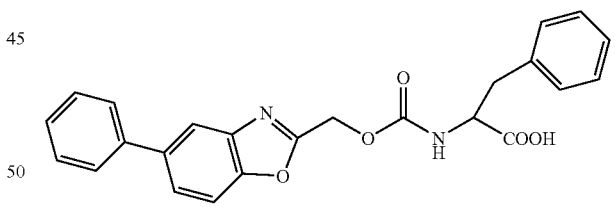

In accordance with the general Scheme 10 the following is the preparation of a compound of Formula I, wherein each of $R^1$ and $R^3$ are phenyl, $R^2$ is benzoxazolyl; A is a single bond; B is —$CH_2$—; m is 1, and n and r are 0.

Step 1:

2-Bromomethyl-5-phenyl-benzoxazole 49.

2-Methyl-5-phenyl-benzoxazole 48 (1.05 g, 5.0 mmol), N-bromosuccinimide (89 mg, 5.0 mmol) and azodiisobutyronitrile (AIBN) (41 mg, 0.25 mmol) in 10 ml of $CCl_4$ was heated to reflux. After 5 hrs an additional 50 mg AIBN were added and the mixture was refluxed overnight. The mixture was diluted, washed with water, dried and concentrated. The crude product was chromatographed to give about 465 mg 2-bromomethyl-5-phenyl-benzoxazole 49.

Step 2:

Acetic acid 5-phenyl-benzoxazol-2-ylmethyl ester 50.

A mixture of 2-bromomethyl-5-phenyl-benzoxazole 49 (440 mg, 1.53 mmol) and cesium acetate (585 mg, 3.06 mmol) in 5 ml DMF was stirred overnight at room temperature. The reaction mixture was diluted with ethyl acetate, washed with brine, dried, filtered and concentrated to yield acetic acid 5-phenyl-benzoxazole-2-ylmethyl ester 50.

Step 3:

(5-Phenyl-benzoxazol-2-yl)methanol 51.

Acetic acid (5-phenyl-benzoxazol-2-yl)methyl ester 50 (409 mg, 1.53 mmol) was dissolved in 10 ml of methanol. Finely ground $K_2CO_3$ (53 mg, 0.38 mmol) was added. After 3 hrs, the mixture was concentrated then diluted with water and extracted with ethyl acetate. The extracts were washed with brine, dried, filtered and concentrated to yield about 251 mg of (5-phenyl-benzoxazole-2-yl)methanol 51.

Step 4:

(R)-3-phenyl-2-(5-phenyl-benzoxazol-2-ylmethoxycarbonylamino) propionic acid allyl ester 52.

(5-Phenyl-benzoxazole-2-yl)methanol 51 (437 mg, 1.94mmol) and carbonyidiimidazole (393 mg, 2.43 mmol) in 7 ml of dry $CH_2Cl_2$ were stirred at room temperature for 3 hrs. The tosic acid salt of (R)-phenylalanine allyl ester(767 mg, 1.94 mmol) was added followed by 0.42 ml of triethylamine (301 mg, 2.98 mmol). The mixture was stirred overnight. The mixture was diluted and washed with 1M HCl solution then with brine. After drying, the organic phase was filtered and concentrated. The crude product was chromatographed to give about 711 mg of (R)-3-phenyl-2-(5-phenyl-benzoxazol-2-ylmethoxycarbonylamino) propionic acid allyl ester 52.

Step 5:

(R)-3-phenyl-2-(5-phenyl-benzoxazol-2-ylmethoxycarbonylamino) propionate 53.

(R)-3-Phenyl-2-(5-phenyl-benzoxazol-2-ylmethoxycarbonylamino)propionic acid allyl ester 52 and $(Ph_3P)_3RhCl$ in 10 ml of 9:1 ethanol/water was heated to 80° C. for 3 hrs. The mixture was cooled and filtered. The filtrate was concentrated, diluted with ethyl acetate, washed, dried, filtered and concentrated. The crude product was chromatographed to give 365 mg of still impure product which was rechromatographed to give 241 mg of product. This was dissolved in 2 ml tert-butyl methyl ether to which 1 ml of dicyclohexylamine was added. The resultant salt was recrystallized from ethyl acetate to give about 208 mg of (R)-3-phenyl-2-(5-phenyl-benzoxazol-2-ylmethoxycarbonylamino) propionic acid 53 mp. 150.9–152.7° C., as dicyclohexylammonium salt.

Example 10

(R)-2-(2-Phenylbenzoxazol-5-ylmethoxycarbonylamino)-3-phenyl propionic acid 60

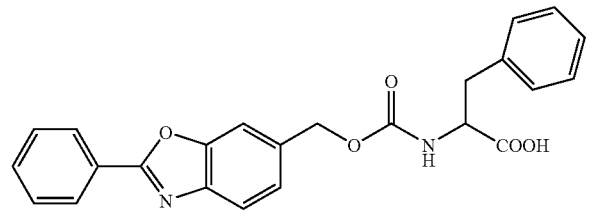

Step 1:

2-Benzylideneamino-4-methylphenol 54.

A solution of 2-amino-p-cresol (1.23 g, 10 mmol) and benzaldehyde (1.06 g, 10 mmol) in methanol (10 ml) was heated at reflux for 2 hrs then cooled in an ice bath. The product was filtered off, washed with a little cold methanol and dried to yield 1.35 g of 2-benzylideneamino-4-methylphenol 54.

Step 2:

5-Methyl-2-phenylbenzoxazole 55.

A mixture of 2-benzylideneamino-4-methylphenol 54 (1.34g, 6.3 mmol) and manganese (III) acetate dihydrate (3.4 g, 12.7 mmol) in toluene (65 ml) was heated at reflux under an atmosphere of $N_2$ for 1 hr and cooled to room temperature. The mixture was filtered to remove the insoluble manganese salts. The filtrate was evaporated under reduced pressure. The residue was taken up in methylene chloride and purified by filtration to yield 1.23 g 5-methyl-2-phenylbenzoxazole 55.

Step 3:

5-Bromomethyl-2-phenylbenzoxazole 56.

5-methyl-2-phenylbenzoxazole 55 (1.23 g, 5.8 mmol) and NBS (1.17 g, 6.5 mmol) were dissolved in carbon tetrachloride (20 ml). The mixture was evacuated and flushed with argon. AIBN (ca. 5 mg) was added and the mixture heated at reflux and irradiated with a sun lamp for 3 hrs. The solvent was evaporated under reduced pressure and the residue purified by chromatography to yield 1.18 g of 5-bromomethyl-2-phenylbenzoxazole 56.

Step 4:

Acetic acid 2-phenylbenzoxazol-5-ylmethyl ester 57.

5-Bromomethyl-2-phenylbenzoxazole 56 (1.0 g, 3.4 mmol) and cesium acetate (1.33 g, 6.94 mmol) were stirred together in DMF(25 ml) under an atmosphere of $N_2$ overnight. The DMF was evaporated under high vacuum and the residue partitioned between ethyl acetate (100 ml) and water (100 ml). The ethyl acetate layer was separated then washed and dried. Evaporation of the solvent yielded 920 mg of acetic acid 2-phenylbenzoxazol-5-ylmethyl ester 57.

Step 5:

2-(Phenylbenzoxazol-5-yl) methanol 58.

Acetic acid 2-phenylbenzoxazol-5-ylmethyl ester 57 (920 mg, 3.4 mmol) and potassium carbonate (100 mg ) were stirred in methanol (50 ml) and water (5 ml) under an atmosphere of $N_2$ for 3 hrs. The solvent was evaporated under reduced pressure to yield a residue which was recrystallized to give 619 mg of 2-(phenylbenzoxazol-5-yl)methanol 58.

Step 6:

(R)-2-(2-Phenylbenzoxazol-5-ylmethoxycarbonylamino)-3-phenylpropionic acid methyl ester 59.

A mixture of 2-(phenylbenzoxazol-5-yl)methanol 58 (215 mg, 0.95 mmol), (R)-2-isocyanato-3-phenylpropionic acid methyl ester 5(196 mg, 0.95 mmol), DMAP (12 mg, 0.095 mmol) and toluene (12 ml) was heated at reflux under an atmosphere of $N_2$ for 3 hrs. The solvent was removed under reduced pressure and the residue purified by chromatography to yield 381 mg of (R)-2-(2-Phenylbenzoxazol-5-ylmethoxycarbonylamino)-3-phenylpropionic acid methyl ester 59.

Step 7:

(R)-2-(2-Phenylbenzoxazol-5-ylmethoxycarbonylamino)-3-phenyl propionic acid 60.

A solution (R)-2-(2-phenylbenzoxazol-5-ylmethoxycarbonylamino)-3-phenylpropionic acid methyl ester 59 (374 mg, 0.8 mmol) in dioxane (8 ml) was treated with a solution of lithium hydroxide hydrate (55 mg, 1.3 mmol) in water (4 mL) under an atmosphere of $N_2$ and stirred for 3 hrs at room temperature. The mixture was acidified with 1N HCl, then extracted with ethyl acetate (25 ml). The ethyl acetate extract was washed, and dried. Evaporation of the solvent afforded the product which was recrystallized to yield 220 mg (60%) of (R)-2-(2-phenylbenzoxazol-5-ylmethoxycarbonylamino)-3-phenyl propionic acid 60, mp. 220.0–221.4° C.

Similarly the following compounds of Formula I, wherein $R^2$ is benzoxazol-5yl, were prepared:

(R)-3-(4-fluoro-phenyl)-2-[2-(4-fluoro-phenyl)-benzoxazol-5-ylmethoxycarbonylamino ]-propionic acid 157, mp. 197.1–198.7° C.;

(R)-2-[2-(4-fluoro-phenyl)-benzoxazol-5-ylmethoxycarbonylamino]-3-phenyl-propionic acid 158, mp. 208.2–208.5° C.;

(R)-2-[2-(3-cyano-phenyl)-benzoxazol-5-ylmethoxycarbonylamino]-3-(4-fluoro-phenyl)-propionic acid, 159, mp. 208.5–209.2° C.;

(R)-2-[2-(3,5-difluoro-phenyl)-benzoxazol-5-ylmethoxycarbonylamino]-3-(4-fluoro-phenyl)-propionic acid, 160, mp. 196.2–197.7° C.;

(R)-2-[2-(1H-indol-4-yl)-benzoxazol-5-ylmethoxycarbonylamino]-3-phenyl-propionic acid 161, mp. 187.0–189.0° C.; and (R)-2-[2-(3,5-difluoro-phenyl)-benzoxazol-5-ylmethoxycarbonylamino]-3-phenyl-propionic acid 162, mp. 193.8–195.0° C.

Example 11

3-Pyridin-4-yl-2-(5-pyridin-3-yl-benzofuran-2-yl-methoxcarbonylamino)-propionic acid 63

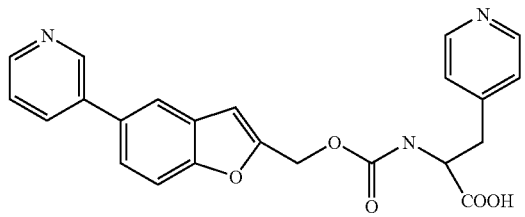

Step 1:

(5-Pyridin-3-yl-benzofuran-2-yl)-methanol 61.

A mixture of ethyl 5-bromo-benzofuran-2-carboxylate 15 (6 g, 22.3 mmole), diethyl 3-pyridylborane (3.66 g, 25 mmole), tetrakis(triphenylphosphine)palladium (0) (270 mg), and potassium phosphate (11.4 g, 53.7 mmole) in DMF (60 ml) was stirred under an argon atmosphere and heated to 100° C. for 16 hrs. The mixture was allowed to cool to room temperature, poured into ethyl acetate and washed with 10% HCl. The organic layer was washed with brine, dried, and evaporated to give 10.4 g of 5-pyridin-3-yl-benzofuran-2-carboxylic acid methyl ester. 534 mg the carboxylic ester were then dissolved in 11 ml t-butanol and stirred under nitrogen. Addition of 198 mg $NaBH_4$ followed by 1.75 ml methanol and the reaction was stirred at 55° C. overnight. After cooling, the reaction was poured into brine and extracted with ethyl acetate. The organic layer was dried and evaporated. The residue was purified by chromatography to give 330 mg of (5-pyridin-3-yl-benzofuran-2-yl)-methanol 61.

Step 2:

5-Pyridin-3-yl-benzofuran-2-ylmethyl-p-nitrophenylcarbonate 62.

A suspension of 330 mg of (5-pyridin-3-yl-benzofuran-2-yl)-methanol 61 in 5 ml $CH_2Cl_2$ was stirred under nitrogen in an ice bath. After addition of 256 mg 4-nitrophenylchloroformate in 5 ml $CH_2Cl_2$, the mixture was allowed to come to room temperature and was stirred for 2 hrs. An additional 75 mg of 4-nitrophenyl chloro-formate in 2 ml $CH_2Cl_2$ were added and the mixture was stirred overnight. After evaporation of the volatiles, the mixture was poured into water and extracted with ethyl acetate. The organic layer was dried, evaporated and purified by chromatography to give 368 mg of 5-pyridin-3-yl-benzofuran-2-ylmethyl-p-nitrophenylcarbonate 62.

Step 3:

3-Pyridin-4-yl-2-(5-pyridin-3-yl-benzofuran-2-ylmethoxycarbonylamino)-propionic acid 63.

A mixture of 300 mg (0.77 mmoles) of 5-pyridin-3-yl-benzofuran-2-ylmethyl-p-nitrophenylcarbonate 62,195 mg (0.77 mmole) of 2-amino-3-pyridin-4-yl-propionic acid methyl ester, and 290 mg DMAP (2.4 mmole) in 2 ml DMF were stirred under nitrogen at room temperature overnight. The mixture was poured into water and extracted with ethyl acetate. The organic phase was washed with saturated $NaHCO_3$, followed by water and brine, dried, and purified by chromatography to give 241 mg of 3-pyridin-4-yl-2-(5-pyridin-3-yl-benzofuran-2-ylmethoxy-carbonyl-amino)-propionic acid 63, mp. 256.6–257.3° C.

Similarly substituting (5-pyridin-3-yl-benzofuran-2-yl)-methanol in Step 1 with 2-hydroxymethyl-5-phenyl-benzofuran 17 gave 2-(5-phenyl-benzofuran-2-ylmethoxycarbonylamino)-3-pyridin-4-yl-propionic acid 163, mp. 219–220° C.; and with 2-hydroxymethyl-5-(4-fluoro-phenyl)-benzofuran gave 2-[5-(4-fluoro-phenyl)-benzofuran-2-ylmethoxycarbonylamino]-3-pyridin-4-yl-propionic acid 176, mp. 255.2–255.7° C.

Similarly substituting (5-pyridin-3-yl-benzofuran-2-yl)-methanol in Step 1 with 2-hydroxymethyl-5-phenyl-benzofuran 17, and 3-amino-3-pyridin-4-yl-propionic acid methyl ester in Step 3 with 2-amino-3-pyridin-3-yl-propionic acid methyl ester gave 2-(5-Phenyl-benzofuran-2-ylmethoxycarbonylamino)-3-pyridin-3-yl-propionic acid, 164, mp. 164–169° C.

Similarly substituting 2-amino-3-pyridin-4-yl-propionic acid methyl ester in Step 3 with appropriate propionates the following compounds were prepared:

ethyl 2-(pyrazin-2-yl)glycinate gave 2-(5-phenyl-benzofuran-2-ylmethoxycarbonylamino)-3-pyrazin-2-yl-propionic acid 165, mp. 144.9–146.0° C.;

ethyl 2-(pyrimidin-5-yl)glycinate gave 2-(5-phenyl-benzofuran-2-ylmethoxycarbonylamino)-3-pyrimidin-5-yl-propionic acid 173, mp. 181.4–184.5° C.;

ethyl 2-(pyrimidin-4-yl)glycinate gave 2-(5-phenyl-benzofuran-2-ylmethoxycarbonylamino)-3-pyrimidin-$^4$-yl-propionic acid 166, mp. 182.9–183.2° C.; and ethyl 2-(pyridazin-3-yl)glycinate gave 2-(5-phenyl-benzofuran-2-ylmethoxycarbonylamino)-3-pyridazin-3-yl-propionic acid 167, mp. 174.7–175.0° C.

Preparation of ethyl 2-(pyrazin-2-yl) glycinate:

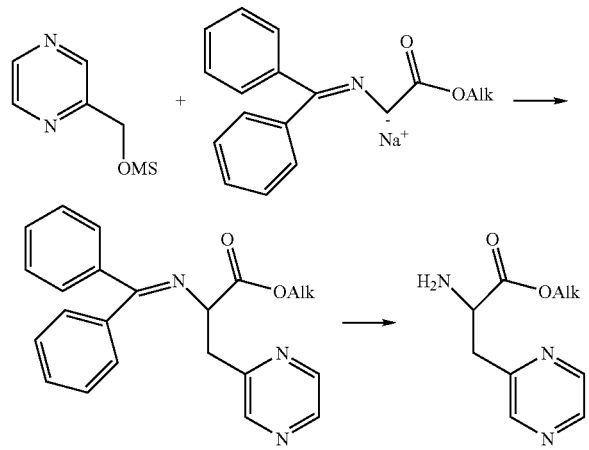

A solution of 2-(methanesulfonyloxymethyl)pyrazine (5 mmole), (prepared from 2'-(pyrazin-2-yl)styrene according to the procedure in EP 02257, followed by treatment with methanesulfonyl chloride, according to a procedure in *Can. J. Chem.* 1999, 77 (4) 463 in 20 ml THF was added dropwise to the sodium salt of ethyl N-(diphenylmethylene)glycinate (5 mmole) in 20 ml DMF cooled in an ice bath. The mixture was allowed to warm to room temperature during 4 hrs. The reaction mixture was partitioned between ether and water. The aqueous layer was separated and reextracted with ether (75 ml). The combined ethereal extracts were washed with brine and dried over MgSO$_4$. Evaporation of the solvent afforded a residue which was chromatographed on silica and eluted with acetone:hexane (1:3) to afford 1.27 g (78%) of ethyl 2-(pyrazin-2-yl)-N-(diphenylmethylene)glycinate.

Ethyl 2-(pyrazin-2-yl)-N-(diphenylmethylene)glycinate (1.64 g, 4.56 mmol) was stirred in 30 ml of (1:1:1) mixture of (HOAc:H$_2$O:THF) for 2 hrs at room temperature. The solvent was evaporated and the residue chromatographed on silica and eluted with 7.5% MeOH(containing 2% NH$_4$OH) in methylene chloride. This afforded 682 mg (77%) of ethyl 2-(pyrazin-2-yl)glycinate.

Similarly, ethyl 2-(pyrimidin-5-yl)glycinate, ethyl 2-(pyrimidin-4-yl)glycinate and ethyl 2-(pyridazin-3-yl)glycinate were prepared following this procedure.

Example 12

(R)-3-Phenyl-2-(5-phenyl-2,3-dihydro-benzofuran-2-ylmethoxycarbonylamino)-propionic acid 68

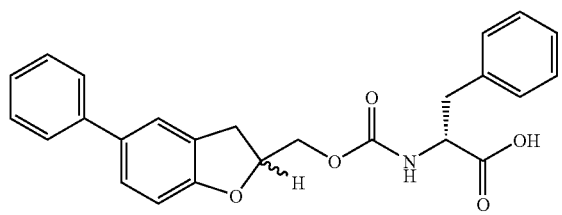

Step 1:

4-Allyloxy-biphenyl 65.

4-Phenylphenol 64 (25.5 g, 0.15 mol), allyl bromide (20.0g, 0.165mol) and K$_2$CO$_3$ (41.5 g, 0.15 mol) in 75 ml of dry DMF were stirred at room temperature overnight. The reaction mixture was diluted with 500 ml of diethyl ether and washed with water. The ether layer was washed with brine, dried and concentrated to give a lightly brown solid that was recrystallized from hexane to give 24.9 g of 4-allyloxy-biphenyl 65.

Step 2:

3-Allyl-biphenyl-4-ol 66.

A solution of 4-allyloxy-biphenyl 65 (5.03 g, 23.9 mmol) in 20 ml of dimethylaniline was heated at 170° C. for 5 hr. The mixture was diluted with 250 ml diethyl ether and washed with 1M HCl solution. The ether phase was washed with brine, dried and concentrated to give a brown solid. The crude product was recrystallized from cyclohexane to give 2.69 g 3-allyl-biphenyl-4-ol 66. The mother liquor was concentrated and chromatographed (7% ethyl acetate/hexane) to give an additional 2.13 g of 2-allyl-4-phenyl-phenol 66.

Step 3:

(5-Phenyl-2,3-dihydroobenzofuran-2-yl)-methanol 67.

A solution of 2-allyl-4-phenyl-phenol 66 (1.05 g, 5.0 mmol) in 10 ml CH$_2$Cl$_2$ was treated with a peracetic acid solution (32% in acetic acid, 2.10 ml). The reaction was allowed to stir at room temperature overnight. The mixture was diluted with diethyl ether and washed with a saturated solution of NaHCO$_3$. The aqueous phase extracted with ether and the combined ether extracts were washed with brine, dried and concentrated to give 0.78 g of a cream colored solid of (5-phenyl-2,3-dihydrobenzofuran-2-yl)-methanol 67.

Step 4:

(R)-3-Phenyl-2-(5-phenyl-2,3-dihydro-benzofuran-2-ylmethoxycarbonylamino)-propionic acid 68.

LiOH solution (1M, 0.85 ml) was added to a solution of (5-phenyl-2,3-dihydrobenzofuran-2-yl)-methanol 67 (183 mg, 0424 mmol) in 2 ml THF. After 3hr, the mixture was cooled in an ice bath and acidified with 1M HCl. The product was extracted into ether. The extracts were washed with brine, dried and concentrated to give (R)-3-phenyl-2-(5-phenyl-2,3-dihydro-benzofuran-2-ylmethoxy-carbonylamino)-propionic acid. The crude product was dissolved in 1 ml ethyl acetate and treated with 0.15 ml of dicyclohexylamine. The product was precipitated by the addition of hexane. The solvents were removed by pipette and the crystals were washed with cold ether then dried in a vacuum oven at 60° C. overnight to give 211 mg of the dicyclohexylamine salt of (R)-3-phenyl-2-(5-phenyl-2,3-dihydrobenzofuran-2-ylmethoxycarbonylamino)-propionic acid 68, mp. 176.3–182° C.

Example 13

3-Phenyl-2-[4-(3-phenyl-propyl)-benzyloxycarbonylamino]-propionic acid 168

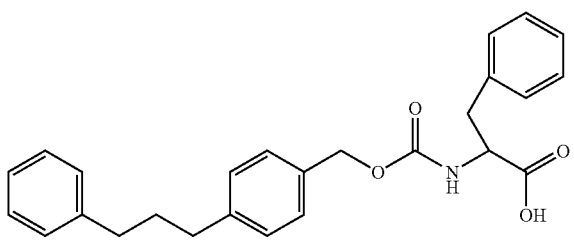

3-Phenyl-2-[4-(3-phenyl-propyl)-benzyloxycarbonylamino]-propionic acid 168, mp. 134.8–135.2° C. was prepared from 4-(3-phenyl-propyl)-benzoic acid (commercially available from Aldrich) followed by reduction to [4-(3-phenyl-propyl)-phenyl ]-methanol, condensation with (R)-2-isocyanato-3-phenyl-propionate of formula 5 and hydrolysis as described for example in Example 1.

Example 14

2-{4-[(Methyl-phenyl-amino)-methyl]-benzyloxy-loxycarbonylamino}-3-phenyl-propionic acid 169

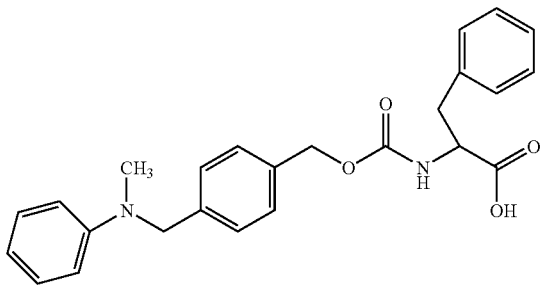

Following the procedure in *J. Org. Chem.* 1996, 61 (11), 3849–3862, methyl-4-formylbenzoate (0.821 g, 5.00 mmol) was dissolved in 1,2-dichloroethane (75 ml) at room temperature. N-methylaniline (0.542 ml, 5.00 mmol) was added followed by sodium triacetoxyborohydride (1.484 g, 7.00 mmol). The mixture was allowed to stir at room temperature overnight. The mixture was quenched with saturated sodium bicarbonate solution and extracted with diethyl ether. The organic extracts were dried over anhydrous sodium sulfate and concentrated en vacuo. The residue was purified by flash chromatography on silica eluted with 4:1 hexane/acetone to give 1.097 g (85.9%) of a slightly yellow oil of 4-[(methyl-phenyl-amino)-methyl]-benzoic acid methyl ester. Reduction to {4-[(methyl-phenyl-amino)-methyl]-phenyl }-methanol, condensation with(R)-2-isocyanato-3-phenyl-propionate of formula 5 and hydrolysis as described for example in Example 1 Steps 2–4, yielded about 1.5 g of 2-{4-[(methyl-phenyl-amino)-methyl]-benzyloxycarbonylamino}-3-phenyl-propionic 169, mp. 69.6–70.1° C.

Example 15

2-[4-(2-Phenoxy-ethyl)-benzyloxycarbonylamino]-3-phenyl-propionic acid 73

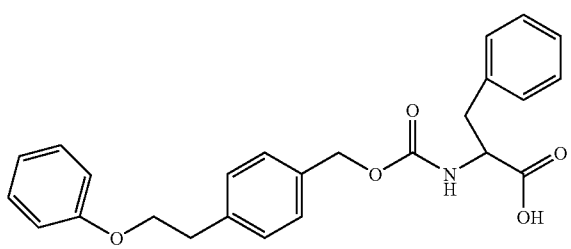

Step 1:

Methyl-4-vinylbenzoate 70.

4-Vinylbenzoic acid 69 (2.222 g, 15.00 mmol) was dissolved in 5 ml of methanol at room temperature. Thionyl chloride (1.094 ml, 15.00mmol) was added dropwise and allowed to stir for 2 hours. The mixture was then heated to reflux for 20 minutes. Upon cooling the mixture was diluted with methylene chloride. The solvent was removed under a stream of nitrogen. The residue was purified by flash chromatography on silica eluted with 95:5 methylene chloride/methanol to give 2.370 g (97.4%) of methyl-4-vinylbenzoate 70 as a yellow oil.

Step 2:

4-(2-Hydroxymethyl)benzoic acid methyl ester 71.

Methyl-4-vinylbenzoate 70 (2.270 g, 14.00 mmol) was dissolved in 50 ml of tetrahydrofuran and cooled to 0° C. 9-BBN (0.5M in THF)(28.00 ml, 14.00 mmol) was added and the mixture was stirred for 2 hours. The solution was allowed to warm to room temperature and stirred for an additional 2 hours. The reaction was cooled to 0° C. and quenched with alkaline hydrogen peroxide. The mixture was then extracted with diethyl ether. The extracts were dried over anhydrous sodium sulfate and concentrated en vacuo. The residue was purified by flash chromatography on silica eluted with 4:1 hexane/acetone to give 1.632g (64.7%) of 4-(2-hydroxyethyl)benzoic acid methyl ester 71 as a clear oil.

Step 3:

4-(2-Phenoxy-ethyl)-benzoic acid methyl ester 72.

4-(2-Hydroxyethyl)benzoic acid methyl ester 71 (1.622 g, 9.00 mmol), triphenyl phosphine (3.541g, 13.50mmol), and diethyl azodicarboxylate (2.13 ml, 13.50 mmol) were dissolved in 50 ml of tetrahydrofuran at room temperature and allowed to stir for 30 minutes. Phenol (0.847 g, 9.00 mmol) was added and the mixture was allowed to stir overnight. The mixture was diluted with water and extracted with diethyl ether. The extracts were dried over anhydrous sodium sulfate and concentrated en vacuo. The residue was purified by flash chromatography on silica eluted with 99:1 hexane/acetone to give 387 mg (16.8%) of 4-(2-phenoxy-ethyl)-benzoic acid methyl ester 72 as a clear oil.

Step 4:

2-[4-(2-phenoxy-ethyl)-benzyloxycarbonylamino]-3-phenyl-propionic acid 73.

4-(2-phenoxy-ethyl)-benzoic acid (387 mg) was further reduced with LiAlH$_4$, condensed with (R)-2-isocyanato-3-phenyl-propionate of formula 5 and hydrolyzed as described for example in Example 1, Steps 2–4, to yield about 550 mg of 2-[4-(2-phenoxy-ethyl)-benzyloxycarbonylamino]-3-phenyl-propionic acid 73 mp. 150.2–152.4° C.

Example 16

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 17

| Composition for Oral Administration | |
|---|---|
| Ingredient | % wt./wt. |
| Active ingredient | 20.0% |
| Magnesium stearate | 0.5% |
| Croscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 18

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Example 19

| Parenteral Formulation (IV) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 20

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 21

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxyanisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 22

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per a

Example 23

In vitro Human Platelet IP Receptor Radioligand Binding Assay

The in vitro Human Platelet IP Receptor Binding Assay measured the strength of a potential drug's binding affinity to its intended target.

For each drug tested, the concentration producing 50% inhibition of binding ($IC_{50}$) and hill slope was determined using iterative curve fitting techniques. If a radioligand Kd was known the inhibition dissociation constant (Ki) of each drug was determined according to the method of Cheng & Prusoff (1973). For this receptor, a typical Kd using the preceding experimental conditions was 1 E-8 M. Usually the negative logarithm of the Ki ($pK_1$) was presented.

EXPERIMENTAL DESIGN

The following buffers were prepared using the purest available water.

| | |
|---|---|
| Lysis Buffer: 10 mM Tris-HCl, 1.0 mM EDTA (di-Na) | pH 7.5 @ 4° C. |
| Assay Buffer: 20 mM Tris-HCl, 5.0 mM MgCl$_2$ | pH 7.4 @ 25° C. |
| Wash Buffer: 20 mM Tris-HCl, 5.0 mM MgCl$_2$ | pH 7.4 @ 4° C. |

1. Membrane Preparation 250 ml Platelet Rich Plasma was transferred into 250 ml centrifuge tubes and spun at 6000 g for 10 min. at 20° C. Pellets were then resuspended in IP lysis buffer and homogenized using a polytron(setting 7, 1×20 sec. burst), brought up to a final volume of 180 ml and centrifuged at 40,000 g for 15 min. at 4° C. The pellets were then resuspended in IP assay buffer, protein density determined by BCA method (Pierce) and stored in 2.0 ml vials at −80° C. for subsequent assay use.

To obtain at least 80 % specific binding, 50 μg protein/assay tube was used in a competition experiment. The final radioligand concentration was 1 to 3E-8 M.

2. Competition Assay

The membranes were thawed at room temperature and then diluted in assay buffer to the appropriate concentration.

First buffer, drug, radioligand, and lastly, membranes were added to the assay tubes.

The assay tubes were incubated at 25° C. for 60 min.

The assay tubes were filtered onto 0.3% PEI pre-treated glass fiber filtermats (GF/B) using Packard Top Count 96 well cell harvester. The tubes were rinsed three times with ice cold 20 mM Tris-HCl, 5 mM MgCl$_2$, pH=7.4 (3×0.5 ml/sample).

Bound radioactivity was determined using liquid scintillation counting.

Example 24

Carrageenan-Induced Mechanical Hyperalgesia Assay

The anti-inflammatory/analgesic activity of compounds of this invention was determined by the Carrageenan-induced Mechanical Hyperalgesia Assay by measuring the inhibition of carrageenan-induced paw hyperalgesia in the rat, using a modification of the method described in L. O. Randall and J. J. Selitto, *Archives of International Pharmacodynamics*, 1957, 11, 409–419, and Vinegar et al., *Journal of Pharmacology and Experimental Therapeutics*, 1969, 166, 96–103.

Male Sprague-Dawley rats (130–150 g) were weighed and randomly assigned to treatment groups (n=10). To induce mechanical hyperalgesia, rats were lightly anesthetized with halothane and administered 1% carrageenan or vehicle 1 (100 μl) in the plantar surface of the left hindpaw. Rats were administered vehicle (10 ml/kg, p.o. or 1 ml/kg, i.v.) or compounds of this invention (at 1, 3, 10, 30 and 100 mg/kg, p.o.) or (0.3, 1.0, 3.0 and 10 mg/kg, i.v.) one hour before testing. Mechanical hyperalgesia was measured using an Analgesy-meter (UGO BASILE, Biological Research Apparatus, Comerio, Italy). The vehicle- or carrageenan-treated hindpaw was. placed on the dome of the apparatus, plantar surface facing down. A constantly increasing force was then applied to the dorsal surface of the paw. The force at which the rat withdrew its paw, struggled, or vocalized was considered the end point.

Treatment groups were compared using a one-way analysis of variance on the paw withdrawal force (RESP). Pairwise comparisons for the drug-treated groups to the vehicle group were made using Fisher's LSD strategy and Dunn's procedure. Percent inhibition of mechanical hyperalgesia was calculated for each animal, and the average $ID_{50}$ value was estimated using the following sigmoidal model:

% inhibition=100/(1+exp (($ID_{50}$-dose)/N))

where $ID_{50}$ is the dose of the compound needed to inhibit half of the maximum response (i.e., 100% in this model) and N is a curvature parameter.

The compounds of this invention were active in this assay.

Example 25

Complete Freund's Adjuvant-Induced Mechanical Hyperalgesia Assay

The anti-inflammatory/analgesic activity of compounds of this invention may also be determined using an adjuvant-induced arthritis pain model in the rat, where pain is assessed by the animal's response to the squeezing of the inflamed foot, using a modification of the method described in J. Hylden et al., *Pain* 1989, 37, 229–243. The modification includes the assessment of hyperalgesia instead of changes in activity of spinal cord neurons.

Briefly, rats were weighed and randomly assigned to treatment groups. To induce mechanical hyperalgesia, rats were lightly anesthetized with halothane and 100 μl of Complete Freund's Adjuvant or saline was administered into the plantar surface of the left hindpaw. Twenty-four hours later, water (vehicle) or compounds of this invention were orally administered to the rats one hour before testing. Mechanical hyperalgesia was measured using an Analgesy-meter (UGO BASILE, Biological Research Apparatus, Comerio, Italy). The saline or carrageenan-treated hindpaw was placed on the dome of the apparatus, plantar surface facing down. A constantly increasing force was then applied to the dorsal surface of the paw, and the force at which the rat withdrew its paw, struggled, or vocalized was considered the end point. The treatment groups were compared using a one-way analysis of variance on the paw withdrawal force. Percent inhibition was calculated for each animal in the form:

100×((c/d-c/v)÷(s/v-c/v))

where c/d is the paw withdrawal force for the carrageenan-treated paw in an animal to which drug has been administered; c/v is the paw withdrawal force for the carrageenan-treated paw in an animal to which vehicle has been administered; and s/v is the paw withdrawal force for the saline-treated paw in an animal to which vehicle has been administered. Significance was determined using Student's t-test.

The compounds of the invention were active in this assay.

Example 26

Inhibition of Bladder Contractions Induced by Isovolumetric Bladder Distension in Rats The inhibition of bladder contractions was determined by an assay using a modification of the method described in C. A. Maggi et al., *J. Pharm. and Exper. Therapeutics*, 1984, 230, 500–513.

Briefly, male Sprague-Dawley rats (200–250 g) were weighed and randomly assigned to treatment groups. A catheter was inserted through the urethra into the bladder to induce bladder contractions, and a warm saline solution (5 mL) was infused. Rhythmic contractions were produced in about 30% of the animals. The compounds of the invention (0.1, 0.3 or 1 mg/kg) were administered intravenous at the onset of regular rhythmic contractions. The effects on rhythmic contracts were then measured.

The compounds of this invention were active in this assay.

Example 27

Inhibition of Volume-Induced Contractions in Rats

The inhibition of bladder contractions was determined by an assay using a modification of the method described in S. S. Hegde et al., *Proceedings of the 26th Annual Meeting of the International Continence Society* (Aug. 27th–30th) 1996, Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a postive control.

The compounds of this invention were active in this assay.

Example 28

Reversal of Endotoxin-Induced Hypotension in Rats

Septic shock, sometimes referred to as endotoxic shock, is caused by the presence of infectious agents, particularly bacterial endotoxins, in the bloodstream and is characterized by hypotension and organ dysfunction. Many symptoms of septic shock, in particular, hypotension, are induced in the rat by the administration of bacterial endotoxins. The ability of a compound to inhibit endotoxin-induced hypotension is therefore predictive of the utility of the compound in the treatment of septic or endotoxic shock.

The activity of the compounds of the invention in the treatment of septic or endotoxic shock was determined by measuring the reversal of endotoxin-induced hypotension in the rat, using a modification of the method described in M. Giral et al., *British Journal of Pharmacology*, 1969, 118, 1223–1231.

Briefly, adult rats (>200 g) were anesthetized with an inhalation anesthetic and femoral arteries and veins were cannulated for insertion of blood pressure transducers and drug administration lines, respectively. They were placed in Mayo restrainers while still under the influence of the anesthetic. After recovery from anesthesia and stabilization of heart rate and blood pressure (which typically required about 30 minutes), endotoxin (50 mg/kg *E. coli* and 25 mg/kg Salmonella) was administered intravenously. Changes in blood pressure and heart rate were monitored. After one hour, compounds of this invention or vehicle were also administered intravenously, and cardiovascular parameters were continuously monitored for the next three hours. Responses are represented as percentage return to initial diastolic blood pressure. Significance was determined using Student's t-test.

The compounds of this invention were active in this assay.

Example 29

Carbaprostacyclin Induced Writhing Test

The analgesic properties of these compounds was investigated with the carbaprostacyclin induced writhing test. The rats (100–130 g) are weighed and randomly assigned to treatment groups (n=8). Each animal is administered vehicle, reference substance or test substance at a dose and dose volume determined by the study director. At the appropriate time after drug dose (peak time of action for test compound), carbaprostacyclin (30 µg/kg, 2 ml/kg, i.p.) is administered. Following carbaprostacyclin administration, the rats are placed in individual plexiglas cages. Writhes are counted for 15 minutes beginning 5 minutes following carbaprostacyclin administration. A writhe consists of a dorsiflexion or strong contraction of the abdominal musculature with simultaneous stretching.

Group comparisons: The treatment groups and the negative control (vehicle+the inducing agent) are compared using a one-way analysis of variance. Pairwise comparisons between the negative control and each treatment group are made using Fisher's LSD test with Bonferroni's adjustment if the overall difference is not significant. The ranked data are applied in the analysis. The positive control group is compared to the negative control group using Wilcoxon rank-sum test for assay verification.

Estimation of $ID_{50}$: The % inhibition is calculated for each animal in the form of 100* (1-(number of writhes/mean writhes for the vehicle group)). The $ID_{50}$ is estimated using the following sigmoidal model: % inhibition=$100/(1+(ID_{50}/dose)^N)$, where $ID_{50}$ is the dose for the compound to achieve half of the maximum response (50%) in the dose response curve, N is the curvature parameter. The maximum response is assumed 100% in the model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the Formula I:

wherein:
 $R^1$ and $R^3$ each independently is optionally substituted aryl;
 $R^2$ is phenyl optionally substituted with one or more substituents selected independently from hydroxy, cyano, lower alkyl, lower alkoxy, alkythlo, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, arylcarbonylamino, alkylaminocarbonyl, arylaminocarbonyl, alkylsulfnylamino, alkylsulfnylamino and trifluoromethyl;

$R^4$ is —COOH or tetrazolyl;

A is a single bond, —O(CH$_2$)$_p$—, —S(CH$_2$)$_p$—, —NR'(CH$_2$)$_p$—, —(CH$_2$)$_p$O—, —O(CH$_2$)$_p$O—, —(CH$_2$)$_p$O(CH$_2$)$_n$CO(CH$_2$)$_n$—, —CON—, —NCO—; —(CH$_2$)$_p$—, —C=C—, or —C≡C—

B is —(CH$_2$)$_q$;

m, p, and q are each independently in each occurrence an integer from 1 to 3 inclusive;

n and r are each 0;

wherein each aryl is independently phenyl, naphthyl or indanyl, and is optionally substituted with one or more substituents selected independently from hydroxy, cyano, lower alkyl, lower alkoxy, alkythio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, alkylcarbonylamino, alkylaminocarbonyl, arylaminocarbonyl, alkylsulfonylamino, arylsulfonylamino and trifluoromethyl; and or an individual isomer, a racemic or non-racemic mixture of isomers, or a pharmaceutically acceptable salt or solvate thereof.

2. The compound of claim 1, wherein $R^4$ is —COOH.

3. The compound of claim 2, wherein $R^1$ is an aryl selected from phenyl, naphthyl or indanyl, and is optionally substituted with one or more substituents selected independently from hydroxy, cyano, lower alkyl, lower alkoxy, alkythio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, arylcarbonylamino, alkylaminocarbonyl, arylaminocarbonyl, alkylsulfonylamino, arylsulfonylamino and trifluoromethyl.

4. The compound of claim 2, wherein $R^3$ is phenyl optionally substituted with halo, lower alkyl, alkoxy, hydroxy or cyano.

5. The compound of claim 2, wherein A is a single bond; —O(CH$_2$)$_p$—, —S(CH$_2$)$_p$—, —NR'(CH$_2$)$_p$—, —(CH$_2$)$_p$O—, —O(CH$_2$)$_p$O—, —(CH$_2$)$_p$O(CH$_2$)$_p$—, or —(CH$_2$)$_n$CO(CH$_2$)$_n$.

6. The compound of claim 5, wherein q is 1.

7. The compound of claim 5, wherein $R^1$ is phenyl optionally substituted one or more times with halo, lower alkyl, alkoxy, hydroxy or cyano.

8. The compound of claim 7, wherein $R^2$ is unsubstituted phenyl.

9. The compound of claim 7, wherein $R^3$ is phenyl optionally substituted with halo, lower alkyl, alkoxy, hydroxy or cyano.

10. The compound of claim 2, wherein $R^2$ is a single bond, —O(CH$_2$)$_p$— or —(CH$_2$)$_p$O—.

11. The compound of claim 10, wherein $R^1$ is phenyl optionally substituted one or more times with fluoro, chloro, methyl, methoxy, hydroxy or cyano.

12. The compound of claim 11, wherein $R^3$ is phenyl optionally substituted one or more times with fluoro, chloro, methyl, methoxy, hydroxy or cyano.

13. The compound of claim 12, wherein $R^2$ is unsubstituted phenyl.

14. The compound of claim 13, wherein q is 1.

15. The compound of claim 2, wherein A is —(CH$_2$)$_p$—, —C=C—, or —CC—.

16. The compound of claim 15, wherein q is 1.

17. The compound of claim 15, wherein $R^1$ is phenyl optionally substituted one or more times with halo, lower alkyl, alkoxy, hydroxy or cyano.

18. The compound of claim 15, wherein $R^2$ is unsubstituted phenyl.

19. The compound of claim 1, wherein said compound is selected from 2-(Biphenyl-4-ylmethoxycarbonylamino)-3phenyl-propionic acid; 2-(4-Benzoylamino-benzyloxycarbonylamino)-3-phenyl-propionic acid; 3-Phenyl-2-(4-phenylethynyl-benzyloxycarbonylamino)-propionic acid; 2-(3-Biphenyl-4-yl-propoxycarbonylamino)-3-phenyl-propionic acid; 3-Phenyl-2-[4-((E)-styryl)-benzyloxycarbonylamino]-propionic acid; 2-[4-(4-Fluoro-benzyloxy)-benzyloxycarbonylamino]-3-phenyl-propionic acid; 2-{4-[(Methyl-phenyl-amino)-methyl]-benzyloxycarbonylamino}-3-phenyl-propionic acid; (R)-3-(1-Methyl-1H-indol-3-yl)-2-(4-phenoxymethyl-benzyloxycarbonylamino)-propionic acid; 3-Phenyl-2-(4-phenylsulfanylmethyl-benzyloxycarbonylamino)-propionic acid; 2-[4-(4-Fluoro-phenoxymethyl)-benzyloxycarbonylamino]-3-phenyl-propionic acid; 2-[4-(4-Chloro-phenoxymethyl)-benzyloxycarbonylamino]-3-phenyl-propionic acid; 2-(4-Phenethyloxy-benzyloxycarbonylamino)-3-phenyl-propionic acid; 2-(4-Benzyloxymethyl-benzyloxycarbonylamino)-3-phenyl-propionic acid; R)-2-(4-Phenoxymethyl-benzyloxycarbonylamino)-3-phenyl-propionic acid; 3-Phenyl-2-[4-(3-phenyl-propyl)-benzyloxycarbonylamino]-propionic acid; 2-[4-(2-Phenoxy-ethyl)-benzyloxycarbonylamino]-3-phenyl-propionic acid; 2-[4-(3-Methoxy-phenoxymethyl)-benzyloxycarbonylamino]-3-phenyl-propionic acid; 3-(3-Benzenesulfonylamino-phenyl)-2-(biphenyl-4-ylmethoxycarbonylamino)-propionic acid; 2-[4-(2-Methoxy-phenoxymethyl)-benzyloxycarbonylamino]-3-phenyl-propionic acid; 2-(3-Fluoro-4-phenoxymethyl-benzyloxycarbonylamino)-3-phenyl-propionic acid; 2-[4-(2-Fluoro-phenoxymethyl)-benzyloxycarbonylamino]-3-phenyl-propionic acid; 2-[4-(3-Fluoro-phenoxymethyl)-benzyloxycarbonylamino]-3-phenyl-propionic acid; 2-(4-Phenethyloxy-benzyloxycarbonylamino)-3-phenyl-propionic acid; 3-(4-Fluoro-phenyl)-2-(4'-hydroxy-biphenyl-4-ylmethoxycarbonylamino)-propionic acid; 3-(3-Benzenesulfonylamino-phenyl)-2-(4-phenoxymethyl-benzyloxycarbonylamino)-propionic acid; 3-Benzyloxy-2-(biphenyl-4ylmethoxycarbonylamino)-propionic acid; 2-(Biphenyl-4-ylmethoxycarbonylamino)-3-(4-methoxy-phenylamino)-propionic acid; 2-(Biphenyl-4-ylmethoxycarbonylamino)-3-phenylamino-propionic acid; (R)-3-Phenyl-2-[4-(3-phenyl-propoxy)-benzyloxycarbonylamino]-propionic acid; (R)-2-[4-(2-Phenoxy-ethoxy)-benzyloxycarbonylamino]-3-phenyl-propionic acid; (R)-2-[4-(3-Methanesulfonylamino-phenoxymethyl)-benzyloxycarbanylamino]-3-phenyl-propionic acid; (R)-2-[4-(3-Benzenesulfonylamino-phenoxymethyl)-benzyloxycarbonylamino]-3-phenyl-propionic acid; (R)-2-[4-(3-Acetylamino-phenoxymethyl)-benzyloxycarbonylamino]-3-phenyl-propionic acid; (R)-2-[4-(3-Nitro-phenoxymethyl)-benzyloxycarbonylamino]-3-phenyl-propionic acid; and (R)-3-Phenyl-2-(4-{3-[(1-phenyl-methanoyl)-amino]-phenoxymethyl}-benzyloxycarbonylamino)-propionic acid.

20. A pharmaceutical composition comprising a therapeutically effective amount of at least one compound of claim 1 in admixture with at least one pharmaceutically acceptable carrier.

21. The pharmaceutical composition of claim 20, wherein the compound is $PGI_2$— preferring receptor antagonist.

22. A method of treating bladder outlet obstruction or urinary incontinence condition in a subject in need of such treatment, comprising administering to the subject a therapeutically effective amount of at least one compound of claim 1.

23. The method of treatment of claim 22, wherein said condition is selected from reduced bladder capacity, frequency of micturition, urge incontinence, stress incontinence, bladder hyperreactivity, benign prostatic hypertrophy (BPH), prostatitis, detrusor hyperreflexia, nocturia, pelvic hypersensitivity, urethritis, pelvic pain syndrome, prostatodynia, cystitis, or idiophatic bladder hypersensitivity.

24. A process for preparing a compound of claim 1, said process comprising:

reacting a compound having a general formula

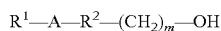

with a compound of general formula

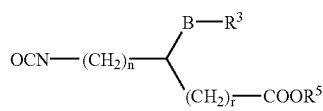

followed by hydrolysis to provide a compound of the general formula

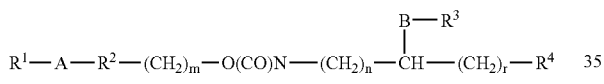

wherein $R^5$ is $C_{1-4}$-alkyl, $R^4$ is COON, and $R^1$, $R^2$, $R^3$, A, B, m, n, and r are as defined in claim 1.

25. A process for preparing a compound of claim 1, said process comprising:

reacting a compound having a general formula

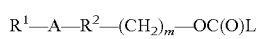

wherein L is a leaving group, with a compound of general formula

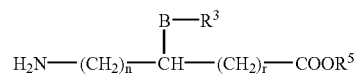

followed by hydrolysis to provide a compound of the general formula

wherein $R^5$ is $C_{1-4}$alkyl, $R^4$ is COOH, and $R^1$, $R^2$, $R^3$, A, B, m, n, and r are as defined in claim 1.

26. A process for preparing a compound of claim 1, said process comprising:

reacting a compound having a general formula

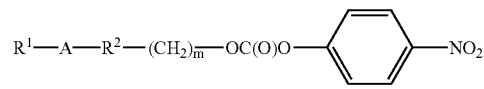

with a compound of general formula

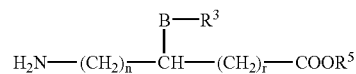

followed by hydrolysis to provide a compound of the general formula

wherein $R^5$ is $C_{1-4}$alkyl, $R^4$ is COOH, and $R^1$, $R^2$, $R^3$, $R^4$, A, B, m, n, and r are as defined in claim 1.

* * * * *